(12) United States Patent
Bishop et al.

(10) Patent No.: US 11,524,050 B2
(45) Date of Patent: Dec. 13, 2022

(54) C3B BINDING POLYPEPTIDE

(71) Applicant: COMPLEMENT THERAPEUTICS LIMITED, London (GB)

(72) Inventors: Paul Bishop, Manchester (GB); Simon Clark, Manchester (GB); Richard Unwin, Manchester (GB)

(73) Assignee: Complement Therapeutics Limited, London (GB)

( * ) Notice: Subject to any disclaimer, the term of this patent is extended or adjusted under 35 U.S.C. 154(b) by 0 days.

(21) Appl. No.: 16/962,108

(22) PCT Filed: Jan. 15, 2019

(86) PCT No.: PCT/EP2019/050949
§ 371 (c)(1),
(2) Date: Jul. 14, 2020

(87) PCT Pub. No.: WO2019/138137
PCT Pub. Date: Jul. 18, 2019

(65) Prior Publication Data
US 2021/0145933 A1   May 20, 2021

(30) Foreign Application Priority Data
Jan. 15, 2018   (GB) .................................. 1800620

(51) Int. Cl.
*A61P 27/02* (2006.01)
*A61K 38/17* (2006.01)

(52) U.S. Cl.
CPC .......... *A61K 38/1709* (2013.01); *A61P 27/02* (2018.01)

(58) Field of Classification Search
CPC ..... A61K 38/1709; A61K 38/00; A61P 27/02; C07K 14/47; C07K 14/70596
See application file for complete search history.

(56) References Cited

U.S. PATENT DOCUMENTS

| | | | |
|---|---|---|---|
| 5,679,546 A | 10/1997 | Ko et al. | |
| 5,981,481 A | 11/1999 | Fearon et al. | |
| 6,458,360 B1 | 10/2002 | Fearon et al. | |
| 6,551,595 B1 | 4/2003 | Rosengard et al. | |
| 8,664,176 B2 * | 3/2014 | Marsh ..................... | A61P 27/02 514/1.1 |
| 2003/0049831 A1 | 3/2003 | Murphy | |
| 2003/0086940 A1 | 5/2003 | Costa et al. | |
| 2004/0146938 A1 | 7/2004 | Nguyen et al. | |
| 2005/0112139 A1 | 5/2005 | Karp | |
| 2005/0169921 A1 | 8/2005 | Bell et al. | |
| 2005/0222027 A1 | 10/2005 | Chiang et al. | |
| 2005/0277158 A1 | 12/2005 | Chen | |
| 2006/0140939 A1 | 6/2006 | Fung | |
| 2007/0065433 A1 | 3/2007 | Mollnes et al. | |
| 2007/0093443 A1 | 4/2007 | Madison et al. | |
| 2007/0274989 A1 | 11/2007 | Fung et al. | |
| 2008/0075728 A1 | 3/2008 | Newman | |
| 2008/0118506 A1 | 5/2008 | An et al. | |
| 2008/0193414 A1 | 8/2008 | Proudfoot et al. | |
| 2008/0221011 A1 | 9/2008 | Gilkeson et al. | |
| 2009/0214538 A1 | 8/2009 | Fung et al. | |
| 2009/0269338 A1 | 10/2009 | Huang et al. | |
| 2009/0324585 A1 | 12/2009 | Robinson et al. | |
| 2010/0009393 A1 | 1/2010 | Morgan et al. | |
| 2010/0130413 A1 | 5/2010 | Marsh et al. | |
| 2010/0240075 A1 | 9/2010 | Granoff et al. | |
| 2011/0091450 A1 | 4/2011 | Schwaeble et al. | |
| 2011/0190221 A1 | 8/2011 | Francois et al. | |
| 2011/0229497 A1 | 9/2011 | Thurman et al. | |
| 2012/0107315 A1 | 5/2012 | Behrens et al. | |
| 2012/0225056 A1 | 9/2012 | Rother et al. | |
| 2012/0258095 A1 | 10/2012 | Demopulos et al. | |
| 2013/0029912 A1 | 1/2013 | Holers et al. | |
| 2013/0064820 A1 | 3/2013 | Magro | |
| 2013/0078245 A1 | 3/2013 | Holers et al. | |
| 2013/0190477 A1 | 7/2013 | Kovacs et al. | |
| 2013/0217616 A1 | 8/2013 | Garred et al. | |
| 2013/0225795 A1 | 8/2013 | Schmidt et al. | |
| 2015/0079084 A1 * | 3/2015 | Her ......................... | A61P 27/02 424/134.1 |
| 2015/0247143 A1 | 9/2015 | Fitzgerald et al. | |
| 2016/0083469 A1 | 3/2016 | Rohrer et al. | |
| 2016/0237125 A1 | 8/2016 | Barlow et al. | |
| 2016/0311893 A1 | 10/2016 | Patz, Jr. et al. | |
| 2016/0326231 A1 | 11/2016 | Hu et al. | |

(Continued)

FOREIGN PATENT DOCUMENTS

| | | |
|---|---|---|
| EP | 0222611 A2 | 5/1987 |
| EP | 2083841 B2 | 11/2013 |
| WO | 1989/09220 A1 | 5/1989 |
| WO | 1992/10205 A1 | 6/1992 |
| WO | 1994/00571 A1 | 1/1994 |
| WO | 1994/16719 A1 | 8/1994 |
| WO | 1995008570 A1 | 3/1995 |
| WO | 1995/09239 A2 | 4/1995 |

(Continued)

OTHER PUBLICATIONS

Akkerman et al (Blood, Nov. 12, 2009, vol. 114, No. 20, 4323-4324) (Year: 2009).*

(Continued)

*Primary Examiner* — Sudhakar Katakam

(74) *Attorney, Agent, or Firm* — Dechert LLP; Andrew T. Wilkins; Victoria E. Pedanou

(57) ABSTRACT

Polypeptides comprising a C3b binding region are disclosed, as well as nucleic acids and vectors encoding such polypeptides, and cells and compositions comprising such polypeptides. Also disclosed are uses and methods using the polypeptides for treating and preventing diseases and conditions.

23 Claims, 17 Drawing Sheets

Specification includes a Sequence Listing.

(56) References Cited

U.S. PATENT DOCUMENTS

2017/0190753 A1* 7/2017 Abache .............. A01K 67/0275
2020/0277360 A1   9/2020 Clark et al.

FOREIGN PATENT DOCUMENTS

| WO | 199944625 A1 | 9/1999 |
| WO | 2000/61752 A2 | 10/2000 |
| WO | 2007149567 A2 | 12/2007 |
| WO | 2008/048675 A2 | 4/2008 |
| WO | 2010056399 A1 | 5/2010 |
| WO | 2011057158 A1 | 5/2011 |
| WO | 2011163412 A1 | 12/2011 |
| WO | 2012/037370 A1 | 3/2012 |
| WO | 2012095519 A1 | 7/2012 |
| WO | 2013/082563 A1 | 6/2013 |
| WO | 2012095519 A1 | 12/2014 |
| WO | 2015023972 A1 | 2/2015 |
| WO | 2016022914 A1 | 2/2016 |
| WO | 2016028150 A1 | 2/2016 |
| WO | 2017/053732 A2 | 3/2017 |
| WO | 2018/002131 A1 | 1/2018 |
| WO | 2018/224663 A1 | 12/2018 |
| WO | 2019/138137 A1 | 7/2019 |

OTHER PUBLICATIONS

UK Search Report GB 1800620.5 dated Oct. 17, 2018, 2 pages.
Kirkitadze et al., Independently Melting Modules and Highly Structured Intermodular Junctions within Complement Receptor Type 1, Biochemistry, 1999, vol. 38(2), pp. 7019-7031.
International Search Report and Written Opinion for PCT/EP2019/050949 dated Sep. 10, 2018, 12 pages.
Zhang et al., Soluble CR1 Therapy Improves Complement Regulation in C3 Glomerulopathy, J Am Sco Nephrol, 2013, vol. 24, pp. 1820-1829.
Zipfel et al., The Role of Complement in AMD, 2010. Adv Excp Med Bio., vol. 285(39), pp. 30192-30202.
Clark et al., Bruch's Membrane Compartmentalizes Complement Regulation in the Eye with Implication for Therapeutic Design in Age-Related Macular Degeneration, Original Research, 2017,vol. 8, pp. 1-10.
Whitmore et al., Complement activation and chroiocapillaris loss in early AMD: Implication for pathophysiology and therapy, 2015, Prog. Retin Eye Res., pp. 1-71.
Clark et al., Impaired binding of the age-related macular degeneration-associated complement factor H 402H allotype to Brunch's membrane in human retina, The Journal of Biological Chemistry, 2010,vol. 285(39), pp. 30192-30202.
Clark et al., Identification of factor H-like protein 1 as the predominant complement regulator in Bruch's membrane: implication forge-related denegeration, J. Immunol., 2014, vol. 193(10), pp. 4962-4970.
Forest et al., Cellular models and therapies for age-related macular degeneration, Disease Models and Mechanisms, 2015, vol. 8, pp. 421-427.
Clark et al. "Role of Factor H and Related Proteins in Regulating Complement Activation in the Macula and Relevance to Age-Related Macular Degeneration." J Clin Med. 4(1): 18-31 (2015).
Fenaille et al. "Site-specific N-glycan characterization of human complement factor H." Glycobiology 17(9): 932-944 (2007).
Foley et al. "Interplay between fibrinolysis and complement: plasmin cleavage of iC3B modulates immune responses." Journal of Thrombosis and Haemostasis 13(4): 610-618 (2014).
Mathern et al. "Molecules great and small: the complement system." Clinical Journal of the American Society of Nephrology 10(9): 1636-1650 (2015).
Thomas. "Furin at the cutting edge: from protein traffic to embryogenesis and disease." Nature reviews Molecular cell biology 3(10): 753-766 (2002).
Tsiftsoglou et al. "Human complement factor I does not require cofactors for cleavage of synthetic substrates." The Journal of Immunology 173(1): 367-375 (2004).
Wang. "Association between complement factor I gene polymorphisms and the risk of age-related macular degeneration: a Meta-analysis of literature." International Journal of Ophthalmology 9(2): 298-305 (2016).
Wu et al. "Structure of complement fragment C3b-factor H and implications for host protection by complement regulators" Nature immunology 10(7): 728-733 (2009).
Zipfel et al. "The Role of Complement in AMD." In: Lambris J., Adamis A. (eds) Inflammation and Retinal Disease: Complement Biology and Pathology. Advances in Experimental Medicine and Biology, vol. 703. Springer, New York, NY: pp. 9-24 (2010).
International Search Report and Written Opinion for PCT/EP2018/065199 dated Oct. 19, 2018, 17 pages.

* cited by examiner a – C3b α chain 114 kDa (a = $a_1$+$a_2$)
b – C3b β chain 75kDa
$a_1$ – iC3b 68 kDa ($a_1$= $a_{1-1}$+$a_{1-2}$)
d – FHL-1
$a_2$ – iC3b 43kDa
$a_{1-1}$ – C3dg 41kDa
$a_{1-2}$ – 27kDa (remaining part of 68kDa iC3b fragment)
$a_{1-2}$* - 27kDa masked by HISCR1a band

|  | FH | FHL-1 | CR1a |
|---|---|---|---|
|  | ~155kDa | ~50kDa |  |
| KD (M) | 5.83E-07 | 1.17E-06 | 2.10E-08 |
| KD Error (%) | 3.0192 | 3.1325 | 0.4186 |
| Rmax | 0.1792 | 0.1495 | 0.1987 |
| Rmax Error (%) | 1.1926 | 0.6311 | 0.0483 |
| Full R^2 | 0.9770 | 0.9550 | 0.8731 |
| Data Location | 167 µgml 20180514 | 278 µgml 20180501 | 30 µgml 20180511 |

FHL-1

Steady state       no

CR1a

Steady state    Yes

Steady state a - C3b alpha chain
b - C3b beta chain
c - iC3b 68 kDa
d - FHL-1
e - iC3b 43 kDa
f - C3dg 41 kDa (part of 68 kDa iC3b)

C3B BINDING POLYPEPTIDE

CROSS-REFERENCE TO RELATED APPLICATIONS

This application is a National Phase of International Application No. PCT/EP2019/050949 filed Jan. 15, 2019, which designated the U.S. and that International Application was published under PCT Article 21(2) in English. This application also includes a claim of priority under 35 U.S.C. § 119(a) and § 365(b) to British patent application No. GB 1800620.5 filed Jan. 15, 2018, the entirety of which is hereby incorporated by reference.

REFERENCE TO A SEQUENCE LISTING

This application contains a sequence listing named "SequenceListing" in ASCII text file format, created on Jan. 20, 2021, being 148 kb in size, which is herein incorporated by reference as though fully disclosed.

FIELD OF THE INVENTION

The present invention relates to the fields of molecular biology, immunology, and medicine. More specifically, the present invention relates to a polypeptide that binds to C3b.

BACKGROUND TO THE INVENTION

Age-related macular degeneration (AMD) is the leading cause of blindness in the developed world: AMD is currently responsible for 8.7% of all global blind registrations and it is estimated that 196 million people will be affected by 2020 (Wong et al. Lancet Glob Heal (2014) 2:e106-16). AMD manifests as the progressive destruction of the macula, the central part of the retina at the back of the eye, leading to loss of central visual acuity. Early stages of the disease see morphological changes in the macula, including first the loss of blood vessels in the choriocapillaris (Whitmore et al., Prog Retin Eye Res (2015) 45:1-29) which are fenestrated blood vessels found in the choroid (a highly vascularized layer that supplies oxygen and nutrition to the outer retina).

AMD is largely a genetic disease. Mutations in genes of the complement system, part of our immune system, are highly associated with increased risk of AMD. Indeed, it has become clear that over-activation of complement is a main driver of disease pathogenesis and many examples of complement over-activation can be seen in the choriocapillaris. The role of complement in AMD is reviewed, for example, by Zipfel et al. Chapter 2, in Lambris and Adamis (eds.), Inflammation and Retinal Disease: Complement Biology and Pathology, Advances in Experimental Medicine and Biology 703, Springer Science+Business Media, LLC (2010), which is hereby incorporated by reference in its entirety. Complement is activated by the deposition onto a surface of protein C3b, a pro-inflammatory breakdown product of immune system protein C3. C3b associates with other proteins to form convertase enzyme complexes for activating and amplifying complement responses, and initiates the amplification loop of the complement cascade, ultimately leading to cell/tissue destruction and a local inflammatory response (all characteristics of AMD).

The choriocapillaris is separated from the metabolically active retinal pigment epithelium (RPE) by Bruch's membrane (BrM), a thin (2-4 µm), acellular, five-layered, extracellular matrix. The BrM serves two major functions: the substratum of the RPE and a blood vessel wall. The structure and function of BrM is reviewed e.g. in Curcio and Johnson, Structure, Function and Pathology of Bruch's Membrane, In: Ryan et al. (2013), Retina, Vol. 1, Part 2: Basic Science and Translation to Therapy. 5th ed. London: Elsevier, pp 466-481, which is hereby incorporated by reference in its entirety.

C3b activation of complement on acellular structures, such as BrM and the intercapillary septa (extracellular matrix filling the spaces between capillaries in the choriocapillaris), is regulated by proteins 'complement factor H' (FH) and 'complement factor I' (FI). FI prevents complement activation by cleaving C3b to an proteolytically-inactive form, designated iC3b, which is unable to participate in convertase assembly. However, iC3b is an opsonin and therefore a mediator of leucocyte recruitment with a subsequent inflammatory response, whereas the further breakdown products of C3b, iC3dg and C3d, are poor opsonins. In order to cleave C3b, FI requires the presence of a cofactor, examples of which include the blood borne FH protein and the membrane-bound surface co-factor 'complement factor 1' (CR1; CD35). CR1 is a membrane receptor expressed on a wide range of cells and is involved in immune complex clearance, phagocytosis, and complement regulation. As well as serving as a co-factor in the FI-mediated cleavage of C3b, CR1 acts as a regulator of complement by accelerating the decay of C3 and C5 convertases. CR1 structure and function is reviewed e.g. in Khera and Das, Mol Immunol (2009) 46(5): 761-772 and Jacquet et al., J Immunol (2013) 190(7): 3721-3731, both of which are hereby incorporated by reference in their entirety.

Hallmark lesions of early AMD, termed drusen, develop within BrM adjacent to the RPE layer (Bird et al, Surv Ophthalmol (1995) 39(5):367-374). Drusen are formed from the accumulation of lipids and cellular debris, and include a swathe of complement activation products (Anderson et al., Prog Retin Eye Res (2009) 29:95-112; Whitcup et al., Int J Inflam (2013) 1-10). The presence of drusen within BrM disrupts the flow of nutrients from the choroid across this extracellular matrix to the RPE cells, which leads to cell dysfunction and eventual death. As the RPE cell monolayer supports the rod and cone cells of the neurosensory retina by providing nutrients and removing waste, their cell death causes dysfunction of photoreceptor cells and subsequent loss of visual acuity.

This represents one of the late stages of AMD, known as 'dry' AMD and also as geographic atrophy, which represents around 90% of AMD cases. In the remaining percentage of cases of late-stage AMD, the presence of drusen promotes choroidal neovascularisation (CNV), where the increased synthesis of vascular endothelial growth factor (VEGF) by RPE cells promotes new blood vessel growth from the choroid/choriocapillaris that breaks through BrM into the retina. These new blood vessels leak and eventually form scar tissue; this is referred to as 'wet' AMD. 'Wet' AMD, while only representing 10% of cases, is the most virulent form of late-stage AMD and has different disease characteristics to 'dry' AMD. There are treatments for wet AMD, where for example the injection of anti-VEGF agents into the vitreous of the eye can slow or reverse the growth of these blood vessels, although it cannot prevent their formation in the first place. Geographic atrophy ('dry' AMD) remains untreatable.

SUMMARY OF THE INVENTION

The present invention provides polypeptides that bind to C3b which are useful for treating or preventing complement-related diseases or conditions.

In one aspect, the present invention provides a polypeptide which is capable of binding C3b, the polypeptide comprising an amino acid sequence having at least 85% identity to SEQ ID NO:4 and wherein the polypeptide has a total length of 450 amino acids or fewer, for use in a method of treating or preventing a complement-related disease or condition.

Also provided is a nucleic acid encoding a polypeptide which is capable of binding C3b, the polypeptide comprising an amino acid sequence having at least 85% identity to SEQ ID NO:4 and wherein the polypeptide has a total length of 450 amino acids or fewer, for use in a method of treating or preventing a complement-related disease or condition.

In another aspect, the present invention provides the use of a polypeptide which is capable of binding C3b, the polypeptide comprising an amino acid sequence having at least 85% identity to SEQ ID NO:4 and wherein the polypeptide has a total length of 450 amino acids or fewer, in the manufacture of a medicament for treating or preventing a complement-related disease or condition.

Also provided is the use of a nucleic acid encoding a polypeptide which is capable of binding C3b, the polypeptide comprising an amino acid sequence having at least 85% identity to SEQ ID NO:4 and wherein the polypeptide has a total length of 450 amino acids or fewer, in the manufacture of a medicament for treating or preventing a complement-related disease or condition.

In another aspect, provided is a method of treating or preventing a complement-related disease or condition, comprising administering to a subject a polypeptide which is capable of binding C3b, the polypeptide comprising an amino acid sequence having at least 85% identity to SEQ ID NO:4 and wherein the polypeptide has a total length of 450 amino acids or fewer.

In another aspect, provided is a method of treating or preventing a complement-related disease or condition in a subject, comprising modifying at least one cell of the subject to express or comprise a polypeptide capable of binding C3b, the polypeptide comprising an amino acid sequence having at least 85% identity to SEQ ID NO:4 and wherein the polypeptide has a total length of 450 amino acids or fewer.

In some embodiments the complement-related disease or condition is an ocular disease or condition.

In some embodiments the treatment or prevention of an ocular disease or condition comprises modifying at least one ocular cell of a subject to express or comprise the polypeptide. In some embodiments the treatment or prevention of an ocular disease or condition comprises modifying at least one ocular cell of a subject to express or comprise a nucleic acid encoding the polypeptide. In some embodiments the treatment or prevention of an ocular disease or condition comprises administering a vector comprising a nucleic acid encoding the polypeptide to at least one ocular cell of a subject. In some embodiments the at least one ocular cell is a retinal pigment epithelial (RPE) cell.

In some embodiments the disease or condition is a disease or condition in which C3b or a C3b-containing complex, an activity/response associated with C3b or a C3b-containing complex, or a product of an activity/response associated with C3b or a C3b-containing complex is pathologically implicated.

In some embodiments the disease or condition is macular degeneration. In some embodiments the disease or condition is selected from one or more of: age-related macular degeneration (AMD), early AMD, intermediate AMD, late AMD, geographic atrophy ('dry' AMD), 'wet' (neovascular) AMD, choroidal neovascularisation (CNV), glaucoma, autoimmune uveitis, diabetic retinopathy, and early-onset macular degeneration (EOMD).

In some embodiments the polypeptide comprises an amino acid sequence having at least 95% identity to SEQ ID NO:4. In some embodiments, $X_1$ is A or T, $X_2$ is P or L, and/or $X_3$ is G or R of SEQ ID NO:4.

In some embodiments the polypeptide has a total length of 50 to 250 amino acids. In some embodiments the polypeptide comprises, or consists of, SEQ ID NO:2 or SEQ ID NO:3.

In some embodiments the polypeptide comprises, or consists of, SEQ ID NO:13.

In some embodiments the polypeptide is capable of acting as a co-factor for Complement Factor I. In some embodiments the polypeptide is capable of diffusing across Bruch's membrane (BrM). In some embodiments the polypeptide binds to C3b in the region bound by a co-factor for Complement Factor I. In some embodiments the polypeptide binds to C3b in the region bound by Complement Receptor 1 (CR1).

In some embodiments the polypeptide comprises a secretory pathway sequence. In some embodiments the secretory pathway sequence comprises, or consists of, SEQ ID NO:7. In some embodiments the polypeptide comprises, or consists of, SEQ ID NO:47, 49, or 51. In some embodiments the polypeptide comprises a cleavage site for removing the secretory pathway sequence.

In one aspect, the present invention provides a polypeptide having at least 80% sequence identity to SEQ ID NO:4, wherein the polypeptide has a length of 700 amino acids or fewer.

In some embodiments, the polypeptide has a length of 50 to 700 amino acids. In some embodiments, the polypeptide has at least 80% sequence identity to SEQ ID NO:4 wherein $X_1$ is A or T, $X_2$ is P or L, and/or $X_3$ is G or R.

Also provided is a polypeptide which is capable of binding to C3b, the polypeptide comprising an amino acid sequence having at least 85% sequence identity to SEQ ID NO:4 and wherein the polypeptide has a total length of 450 amino acids or fewer.

In some embodiments the polypeptide comprises an amino acid sequence having at least 95% identity to SEQ ID NO:4. In some embodiments $X_1$ is A or T, $X_2$ is P or L, and/or $X_3$ is G or R.

In some embodiments the polypeptide has a total length of 50 to 250 amino acids.

In some embodiments, the polypeptide comprises, or consists of, an amino acid sequence according to SEQ ID NO:2. In some embodiments, the polypeptide comprises, or consists of, an amino acid sequence according to SEQ ID NO:3. In some embodiments, the polypeptide comprises, or consists of, an amino acid sequence according to SEQ ID NO:13.

In some embodiments, the polypeptide is capable of binding to C3b. In some embodiments, the polypeptide binds to C3b in the region bound by a co-factor for Complement Factor I. In some embodiments, the polypeptide binds to C3b in the region bound by Complement Receptor 1 (CR1).

In some embodiments, the polypeptide acts as a co-factor for Complement Factor I.

In some embodiments, the polypeptide is capable of diffusing across Bruch's membrane (BrM). In some embodiments, the polypeptide is not glycosylated or is partially glycosylated. In some embodiments, the polypeptide comprises at least one amino acid substitution, e.g. one, two, three or four substitutions, at position 509, 578, 959 and/or 1028 (numbered according to Uniprot: P17927 (SEQ ID NO:1)). In some embodiments, the at least one amino acid substitution is one or more of N509Q, N578Q, N959Q and/or N1028Q (numbered according to Uniprot: P17927 (SEQ ID NO:1)). In some embodiments, the polypeptide comprises, or consists of, SEQ ID NO:5, SEQ ID NO:6, and/or SEQ ID NO:15.

In some embodiments, the polypeptide additionally comprises a secretory pathway sequence. In some embodiments, the secretory pathway sequence comprises, or consists of, SEQ ID NO:7. In some embodiments, the polypeptide additionally comprises a cleavage site for removing the secretory pathway sequence. In some embodiments the polypeptide comprises, or consists of, SEQ ID NO:47, 49 or 51.

In another aspect, the present invention provides a nucleic acid encoding a polypeptide according to the present invention.

In another aspect, the present invention provides a vector comprising a nucleic acid of the present invention.

In another aspect, the present invention provides a cell comprising a polypeptide, nucleic acid, or vector according to the present invention.

In another aspect, the present invention provides a method for producing a polypeptide, comprising introducing into a cell a nucleic acid or a vector according to the present invention, and culturing the cell under conditions suitable for expression of the polypeptide.

In another aspect, the present invention provides a cell, which is obtained or obtainable by the method for producing a polypeptide according to the present invention.

In another aspect, the present invention provides a pharmaceutical composition comprising a polypeptide, nucleic acid, vector or cell according to the present invention. In some embodiments, the pharmaceutical composition comprises a pharmaceutically acceptable carrier, adjuvant, excipient, or diluent.

In another aspect, the present invention provides a polypeptide, nucleic acid, vector, cell or pharmaceutical composition according to the present invention, for use in a method of treating or preventing a disease or condition.

In another aspect, the present invention provides the use of a polypeptide, nucleic acid, vector, cell or pharmaceutical composition according to the present invention, in the manufacture of a medicament for treating or preventing a disease or condition.

In another aspect, the present invention provides a method of treating or preventing a disease or condition, comprising administering to a subject a polypeptide, nucleic acid, vector, cell or pharmaceutical composition according to the present invention.

In another aspect, the present invention provides a method of treating or preventing a disease or condition in a subject, comprising modifying at least one cell of the subject to express or comprise a nucleic acid, vector or polypeptide according to the present invention.

In some embodiments in accordance with various aspects of the present invention, the disease or condition is a disease or condition in which C3b or a C3b-containing complex, an activity/response associated with C3b or a C3b-containing complex, or a product of an activity/response associated with C3b or a C3b-containing complex is pathologically implicated. In some embodiments, the disease or condition is macular degeneration. In some embodiments, the disease or condition is age-related macular degeneration (AMD). In some embodiments, the method for treating or preventing a disease or condition comprises modifying at least one retinal pigment epithelial (RPE) cell of the subject to express or comprise a nucleic acid, vector, or polypeptide according to the present invention.

In another aspect, the present invention provides a kit of parts comprising a predetermined quantity of a polypeptide, nucleic acid, vector, cell, or pharmaceutical composition according to the present invention.

DESCRIPTION

Complement-based therapies for AMD have thus far concentrated upon injecting complement regulating antibodies into the eye. Such therapies have provided little to no therapeutic benefit as these proteins cannot reach the target area, i.e. the BrM and its underlying vasculature, the choriocapillaris at all, or in effective concentrations.

Complement Factor I (FI)-mediated regulation of complement, i.e. the cleavage of C3b to iC3b (proteolytically-inactive C3b), requires cofactors such as membrane-anchored CR1. However, the present inventors have discovered that it is not necessary to provide full-length membrane-bound CR1, nor even a soluble version of CR1 merely lacking the transmembrane domain, for successful cofactor activity. Instead, the inventors have discovered that short CR1 fragments comprising the CR1 C3b-binding domains are sufficient to enable efficient FI-mediated C3b cleavage.

Thus, the present invention relates to soluble, truncated polypeptides derived from the FI cofactor CR1. The polypeptides comprise domains that are capable of binding to C3b, such that they can act as essential FI cofactors for the regulation of complement activation. A key advantage of the soluble, truncated polypeptides is their ability to pass through BrM, and thus they are able to reach all regions associated with AMD, i.e. the RPE/BrM interface, BrM and the choroid, including the intercapillary septa (the extracellular matrix between the blood vessels of the choriocapillaris). The present invention also provides non-glycosylated polypeptides derived from CR1, which may aid polypeptide passage through BrM. The polypeptides are expressed and secreted easily, enabling in situ expression by cells local to the affected sites and targeting of the polypeptides to areas affected by complement over-activation. In situ expression of the polypeptides may be achieved using gene therapy techniques. In situ expression provides targeted therapy to areas of need without disrupting functioning complement regulation elsewhere in the body.

The present invention enables supplementation of a deteriorating complement regulation system without replacing the endogenous complement regulation currently in place, or interfering in the rest of the complement cascade.

Polypeptides

A polypeptide according to the present invention may comprise, or consist of, one or more C3b binding regions.

A polypeptide according to the present invention has at least 80% sequence identity to SEQ ID NO:4, wherein the polypeptide has a length of 700 amino acids or fewer. In some embodiments, the polypeptide comprises, or consists of, an amino acid sequence having at least 80% sequence identity to SEQ ID NO:4, wherein the polypeptide has a length of 700 amino acids or fewer.

A polypeptide according to the present invention may comprise, or consist of, an amino acid sequence of 700 amino acids or fewer having at least 80% sequence identity to SEQ ID NO:4.

In some embodiments, the polypeptide comprises, or consists of, an amino acid sequence of 650, 600, 550, 500, 450, 400, 350, 300, 250, or 200 amino acids or fewer. In some embodiments, the polypeptide comprises, or consists of, an amino acid sequence having 1 to 200 amino acids, 1 to 250 amino acids, 1 to 300 amino acids, 1 to 350 amino acids, 1 to 400 amino acids, 1 to 450 amino acids, 1 to 500 amino acids, 1 to 550 amino acids, 1 to 600 amino acids, 1 to 650 amino acids, or 1 to 700 amino acids. In some embodiments, the polypeptide has a length of 50 to 700 amino acids. In some embodiments, the polypeptide has a length of 100 to 650 amino acids. In some embodiments, the polypeptide has a length of 100 to 550 amino acids. In some embodiments, the polypeptide has a length of 150 to 450 amino acids. In some embodiments, the polypeptide has a length of 400 to 700 amino acids. In some embodiments, the polypeptide has a length of 700 to 1000 or greater than 1000 amino acids.

"Length" as used herein refers to the total length of the polypeptide; that is, "length" refers to the measurement or extent of the entire polypeptide from end to end, i.e. from the N-terminus to the C-terminus. "Length" as used herein is measured by the number of amino acid residues within the polypeptide.

In some embodiments the polypeptide is a detached/discrete/separate/individual molecule. In some embodiments, the polypeptide is a single contiguous amino acid sequence that is unconnected, i.e. not joined, fused or attached, to another amino acid sequence. In some embodiments the polypeptide is not attached by an amino acid linker or a non-amino acid linker to another polypeptide or amino acid sequence. In some embodiments the polypeptide is not a section, part or region of a longer amino acid sequence, i.e. it is not part of an amino acid sequence that exceeds the maximum, specified, polypeptide length. In some embodiments the polypeptide is not part of, or does not form a section of, a fusion protein. In some embodiments the polypeptide may comprise a sequence provided herein and one or more additional amino acids, as long as the maximum length of the polypeptide is not exceeded. The short length of the polypeptides described herein enables the polypeptides to pass through the BrM and reach sites of complement activation.

In some embodiments the polypeptide has a total length of 700, 650, 600, 550, 500, 450, 400, 350, 300, 250, or 200 amino acids or fewer. In some embodiments the polypeptide has a total length of 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, or 70 amino acids or fewer. In some embodiments the polypeptide has a total length of 1 to 70 amino acids, 1 to 80 amino acids, 1 to 90 amino acids, 1 to 100 amino acids, 1 to 110 amino acids, 1 to 120 amino acids, 1 to 130 amino acids, 1 to 140 amino acids, 1 to 150 amino acids, 1 to 160 amino acids, 1 to 170 amino acids, 1 to 180 amino acids, 1 to 190 amino acids, 1 to 200 amino acids, 1 to 210 amino acids, 1 to 220 amino acids, 1 to 230 amino acids, 1 to 240 amino acids, 1 to 250 amino acids, 1 to 260 amino acids, 1 to 270 amino acids, 1 to 280 amino acids, 1 to 290 amino acids, 1 to 300 amino acids, 1 to 310 amino acids, 1 to 320 amino acids, 1 to 330 amino acids, 1 to 340 amino acids, 1 to 350 amino acids, 1 to 360 amino acids, 1 to 370 amino acids, 1 to 380 amino acids, 1 to 390 amino acids, 1 to 400 amino acids, 1 to 410 amino acids, 1 to 420 amino acids, 1 to 430 amino acids, 1 to 440 amino acids, or 1 to 450 amino acids. In some embodiments the polypeptide has a total length of 50 to 450 amino acids, 50 to 400 amino acids, 50 to 350 amino acids, 50 to 300 amino acids, 50 to 250 amino acids, 50 to 200 amino acids, 100 to 250 amino acids, 100 to 200 amino acids, 150 to 250 amino acids, or 150 to 200 amino acids. In some embodiments the polypeptide has a total length of one of 61, 72, 194, 212, 231, 388, 406, or 644 amino acids.

In some embodiments a polypeptide of the present invention has a maximum molecular weight of 80 kDa, whether the polypeptide is covalently/non-covalently bonded to a larger complex, part of a larger complex, or is not part of a larger complex. In some embodiments a polypeptide of the present invention has a molecular weight of 75 kDa or less, 70 kDa or less, 65 kDa or less, 60 kDa or less, 55 kDa or less, 50 kDa or less, 45 kDa or less, 40 kDa or less, 35 kDa or less, 30 kDa or less, 29 kDa or less, 28 kDa or less, 27 kDa or less, 26 kDa or less, 25 kDa or less, 24 kDa or less, 23 kDa or less, 22 kDa or less, 21 kDa or less, 20 kDa or less, 19 kDa or less, 18 kDa or less, 17 kDa or less, 16 kDa or less, 15 kDa or less, 14 kDa or less, 13 kDa or less, 12 kDa or less, 11 kDa or less, or 10 kDa or less. In some embodiments the polypeptide has a maximum molecular weight of 50 kDa, i.e. 50 kDa or less. In some embodiments the polypeptide has a maximum molecular weight of 26 kDa, i.e. 26 kDa or less. In some embodiments the polypeptide has a maximum molecular weight of 24 kDa, i.e. 24 kDa or less. In some embodiments the polypeptide has a maximum molecular weight of 22 kDa, i.e. 22 kDa or less. In some embodiments the polypeptide has a maximum molecular weight of 20 kDa, i.e. 20 kDa or less.

In some embodiments, a polypeptide of the present invention comprises, or consists of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:4. In some embodiments, $X_1$ is A or T, $X_2$ is P or L, and/or $X_3$ is G or R. In some embodiments, $X_1$ is A, $X_2$ is P, and/or $X_3$ is G. In some embodiments, $X_1$ is A, $X_2$ is L, and/or $X_3$ is R. In some embodiments, $X_1$ is A, $X_2$ is P, and/or $X_3$ is R. In some embodiments, $X_1$ is A, $X_2$ is L, and/or $X_3$ is G. In some embodiments, $X_1$ is T, $X_2$ is L, and/or $X_3$ is R. In some embodiments, $X_1$ is T, $X_2$ is P, and/or $X_3$ is G. In some embodiments, $X_1$ is T, $X_2$ is L, and/or $X_3$ is G. In some embodiments, $X_1$ is T, $X_2$ is P, and/or $X_3$ is R.

In some embodiments the polypeptide comprises, or consists of, an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:4, wherein the polypeptide has a length provided herein. For example, in some embodiments the polypeptide comprises, or consists of, an amino acid sequence having 85% sequence identity to SEQ ID NO:4, wherein the polypeptide has a total length of 450, 440, 430, 420, 410, 400, 390, 380, 370, 360, 350, 340, 330, 320, 310, 300, 290, 280, 270, 260, 250, 240, 230, 220, 210, 200, 190, 180, 170, or 160 amino acids or fewer; in some embodiments the polypeptide comprises, or consists of, an amino acid sequence having 90% sequence identity to SEQ ID NO:4, wherein the polypeptide has a total length of 450, 440, 430, 420, 410, 400, 390, 380, 370, 360, 350, 340, 330, 320, 310, 300, 290, 280, 270, 260, 250, 240, 230, 220, 210, 200, 190, or 180 amino acids or fewer; in some embodiments the polypeptide comprises, or consists of, an amino acid sequence having 95% sequence identity to SEQ ID NO:4, wherein the polypeptide has a total length of 450, 440, 430, 420, 410, 400, 390, 380, 370, 360, 350, 340, 330, 320, 310, 300, 290, 280, 270, 260, 250, 240, 230, 220, 210, 200, 190, or 180 amino acids or fewer; in some embodiments the polypeptide comprises, or consists of, an amino acid sequence having 98% sequence identity to SEQ ID NO:4, wherein the polypeptide has a total length of 450, 440, 430, 420, 410, 400, 390, 380, 370, 360, 350, 340, 330, 320, 310, 300, 290, 280, 270, 260, 250, 240, 230, 220, 210, or 200 amino acids or fewer.

In some embodiments the polypeptide comprises, or consists of, an amino acid sequence having at least 85% sequence identity to SEQ ID NO:4, wherein the polypeptide has a total length of 450 amino acids or fewer. In some embodiments the polypeptide comprises, or consists of, an amino acid sequence having at least 85% sequence identity to SEQ ID NO:4, wherein the polypeptide has a total length of 50 to 450 amino acids. In some embodiments the polypeptide comprises, or consists of, an amino acid sequence having at least 85% sequence identity to SEQ ID NO:4, wherein the polypeptide has a total length of 250 amino acids or fewer. In some embodiments the polypeptide comprises, or consists of, an amino acid sequence having at least 85% sequence identity to SEQ ID NO:4, wherein the polypeptide has a total length of 50 to 250 amino acids. In some embodiments the polypeptide comprises, or consists of, an amino acid sequence having at least 95% sequence identity to SEQ ID NO:4, wherein the polypeptide has a total length of 450 amino acids or fewer. In some embodiments the polypeptide comprises, or consists of, an amino acid sequence having at least 95% sequence identity to SEQ ID NO:4, wherein the polypeptide has a total length of 50 to 450 amino acids. In some embodiments the polypeptide comprises, or consists of, an amino acid sequence having at least 95% sequence identity to SEQ ID NO:4, wherein the polypeptide has a total length of 250 amino acids or fewer. In some embodiments the polypeptide comprises, or consists of, an amino acid sequence having at least 95% sequence identity to SEQ ID NO:4, wherein the polypeptide has a total length of 50 to 250 amino acids.

Human CR1 (UniProt: P17927 (Entry version 181 (25 Oct. 2017), Sequence version 3 (2 Mar. 2010)); SEQ ID NO:1) has a 2,039 amino acid sequence (including an N-terminal, 41 amino acid signal peptide), and comprises 30 complement control protein (CCP) domains (also known as sushi domains or short consensus repeats (SCRs)), with the N-terminal 28 CCPs organised into four long homologous repeat (LHR) domains each comprising 7 CCPs: LHR-A, LHR-B, LHR-C and LHR-D. The C3b binding region of CR1 is found in CCPs 8-10 in LHR-B (UniProt: P17927 positions 491 to 684; SEQ ID NO:2), and CCPs 15-17 in LHR-C (UniProt: P17927 positions 941 to 1134; SEQ ID NO:3). CCPs 8-10 and 15-17 differ in sequence by three amino acid residues, as shown in consensus sequence SEQ ID NO:4.

A polypeptide according to the present invention may comprise, or consist of, an amino acid sequence corresponding to CCPs 8-10 (SEQ ID NO:2) and/or CCPs 15-17 (SEQ ID NO:3). In some embodiments, a polypeptide of the present invention comprises, or consists of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:2 and/or SEQ ID NO:3. Such polypeptides may have any length provided herein.

A polypeptide according to the present invention may comprise, or consist of, an amino acid sequence corresponding to CCPs 8-10 and 15-17. The polypeptide may comprise or consist of CCPs 8-10 and 15-17 in their native CR1 sequence (SEQ ID NO:30). The polypeptide may comprise or consist of CCPs 8-10 joined to CCPs 15-17. This may be in a contiguous sequence (SEQ ID NO:13), or achieved by a linker between CCPs 8-10 and 15-17 (e.g. SEQ ID NO:14). In some embodiments, a polypeptide of the present invention comprises, or consists of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:13, SEQ ID NO:14 and/or SEQ ID NO:30. Such polypeptides may have any length provided herein.

A polypeptide according to the present invention may comprise, or consist of, an amino acid sequence corresponding to one or more of sequence 'A' (SEQ ID NO:8), sequence 'B' (SEQ ID NO:16) and/or 'Sequence C' (SEQ ID NO:17). In some embodiments, the polypeptide consists of a sequence selected from sequence 'A' (SEQ ID NO:8), sequence 'B' (SEQ ID NO:16) and 'Sequence C' (SEQ ID NO:17). In some embodiments, a polypeptide of the present invention comprises, or consists of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to one or more of sequences 'A' (SEQ ID NO:8), 'B' (SEQ ID NO:16) and/or 'C' (SEQ ID NO:17).

In some embodiments, where a polypeptide according to the present invention comprises, or consists of, sequence 'B' (SEQ ID NO:16) or an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to sequence 'B' (SEQ ID NO:16), $X_1$ is A or T. In some embodiments, $X_1$ is A. In some embodiments, $X_1$ is T.

In some embodiments, where a polypeptide according to the present invention comprises, or consists of, sequence 'C' (SEQ ID NO:17) or an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to sequence 'C' (SEQ ID NO:17), $X_2$ is P or L and/or $X_3$ is G or R. In some embodiments, $X_2$ is P and/or $X_3$ is G. In some embodiments, $X_2$ is P and/or $X_3$ is R. In some embodiments, $X_2$ is L and/or $X_3$ is G. In some embodiments, $X_2$ is L and/or $X_3$ is R.

In some embodiments sequence 'B' corresponds to SEQ ID NO:9 or SEQ ID NO:11. In some embodiments sequence 'C' corresponds to SEQ ID NO:10 or SEQ ID NO:12.

The present invention includes polypeptides comprising sequences 'A', 'B', and/or 'C' as described herein, and combinations thereof, including at least the following combinations (organised from N-terminus to C-terminus):

A+B
B+C
A+C
C+A
A+B+C
B+C+A
C+A+B
A+B+C+A
B+C+A+B
C+A+B+C
A+B+C+A+B
B+C+A+B+C
A+B+C+A+B+C
A+B+C+A+B+C+Y (where Y=one or more of A, B and/or C).

In some embodiments, the polypeptide comprises, or consists of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any combination of CCP domains or any combination of sequences 'A', 'B' and/or 'C' described herein.

In some embodiments, the combination of CCP domains is a combination found in native CR1. In some embodiments, the combination of CCP domains is not a combination found in native CR1.

In some embodiments, the polypeptide comprises, or consists of, an amino acid sequence having multiple copies of sequence 'A', multiple copies of sequence 'B', and/or multiple copies of sequence 'C'. In some embodiments, the polypeptide comprises 1, 2, 3, 4, 5, 6, 7, 8 or more copies of one or more of sequences 'A', 'B' and/or 'C'. In some embodiments, the polypeptide comprises 1, 2, 3, 4, 5, 6, 7, 8 or more copies of sequence 'A'; 1, 2, 3, 4, 5, 6, 7, 8 or more copies of sequence 'B'; and/or 1, 2, 3, 4, 5, 6, 7, 8 or more copies of sequence 'C'. In some embodiments, the polypeptide comprises 9, 10, or more copies of one or more of sequences 'A', 'B' and/or 'C'.

In some embodiments, a polypeptide according to the present invention lacks substantial sequence identity to one or more of amino acid sequences 1-490, 685-940 and/or 1135-2039 of human CR1 (SEQ ID NO:1). A polypeptide that lacks substantial sequence identity as described herein may have less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% sequence identity to one or more of amino acid sequences 1-490, 685-940 and/or 1135-2039 of human CR1 (SEQ ID NO:1). In some embodiments a polypeptide according to the present invention lacks amino acid sequence having substantial sequence identity to CR1 long homologous repeat (LHR) domains LHR-A and/or LHR-D. In some embodiments a polypeptide according to the present invention lacks amino acid sequence having substantial sequence identity to CR1 CCP domains 1-7, 11-14 and/or 18-30. Amino acid residues of SEQ ID NO:1 are numbered according to Uniprot P17927; Entry version 181 (25 Oct. 2017), Sequence version 3 (2 Mar. 2010).

A polypeptide according to the present invention, and/or described herein, may be isolated and/or substantially purified.

Further Features of the Polypeptide

Polypeptides according to the present invention may comprise modifications and/or additional amino acid sequences. The modifications and/or additional amino acid sequences may be included in the length limitation of a polypeptide provided herein such that the length limitation of that polypeptide is not exceeded.

In some embodiments, an additional amino acid sequence comprises, or consists of, no more than 25, 50, 100, 150, or 200 amino acids, i.e. an additional amino acid sequence comprises, or consists of, 1-25, 1-50, 1-100, 1-150, or 1-200 amino acids. In some embodiments, an additional amino acid sequence comprises more than 200 amino acids. In some embodiments, an additional amino acid sequence comprises no more than 100 amino acids at the C-terminus of a polypeptide according to the present invention, and/or no more than 100 amino acids at the N-terminus of a polypeptide according to the present invention.

In some embodiments, an additional amino acid sequence results in a polypeptide longer than 700 amino acids. In some embodiments, a polypeptide according to the present invention comprises, or consists of, 700 or more amino acids. For example, the polypeptide may comprise, or consist of, 700-750, 750-800, 800-850, 850-900, 900-950, 950-100, or more than 1000 amino acids.

In some embodiments, an additional amino acid sequence described herein lacks substantial sequence identity to one or more of amino acid sequences 1-490, 685-940 and/or 1135-2039 of human CR1 (SEQ ID NO:1, numbered according to Uniprot P17927; Entry version 181 (25 Oct. 2017), Sequence version 3 (2 Mar. 2010)). In some embodiments, the additional amino acid sequence lacks substantial sequence identity to CR1 CCP domains 1-7, 11-14 and/or 18-30. In some embodiments, the additional amino acid sequence has less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% sequence identity to one or more of amino acid sequences 1-490, 685-940 and/or 1135-2039 of human CR1 (SEQ ID NO:1). In some embodiments the additional amino acid sequence lacks substantial sequence identity to CR1 long homologous repeat (LHR) domains LHR-A and/or LHR-D.

In some embodiments, a polypeptide may lack amino acid sequence having substantial sequence identity to a region of a co-factor for Complement Factor I (e.g. CR1) other than in the C3b binding region. For example, the polypeptide may lack amino acid sequence having substantial sequence identity to CR1 other than in CR1 CCP domains 8-10 and/or 15-17 (residues 491 to 684 and/or 941 to 1134, respectively, of SEQ ID NO:1). In some embodiments, the polypeptide may lack amino acid sequence having substantial sequence identity to CR1 CCP domains 1-7, 11-14 and/or 18-30. A polypeptide lacking amino acid sequence having substantial sequence identity as described herein may have less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% sequence identity to one or more of amino acid sequences 1-490, 685-940 and/or 1135-2039 of human CR1 (SEQ ID NO:1).

In some embodiments, a polypeptide according to the present invention may comprise a secretory pathway sequence. As used herein, a secretory pathway sequence is an amino acid sequence which directs secretion of polypeptide. The secretory pathway sequence may be cleaved from the mature protein once export of the polypeptide chain across the rough endoplasmic reticulum is initiated. Polypeptides secreted by mammalian cells generally have a signal peptide fused to the N-terminus of the polypeptide, which is cleaved from the translated polypeptide to produce a "mature" form of the polypeptide.

In some embodiments, the secretory pathway sequence may comprise or consist of a leader sequence (also known as a signal peptide or signal sequence). Leader sequences normally consist of a sequence of 5-30 hydrophobic amino acids, which form a single alpha helix. Secreted proteins and proteins expressed at the cell surface often comprise leader sequences. The leader sequence may be present in the newly-translated polypeptide (e.g. prior to processing to remove the leader sequence). Leader sequences are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

In some embodiments, the secretory pathway sequence is derived from Complement Factor H (FH). In some embodiments, the secretory pathway sequence comprises or consists of SEQ ID NO:7. In some embodiments, the secretory pathway sequence of the polypeptide of the present invention comprises, or consists of, an amino acid sequence having at least 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO:7.

In some embodiments a polypeptide according to the present invention comprises, or consists of, an amino acid sequence corresponding to SEQ ID NO:47, 49, and/or 51. In some embodiments the polypeptide comprises, or consists of, an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:47, 49 and/or 51. Such polypeptides may have any length provided herein.

In some embodiments, a polypeptide according to the present invention may additionally comprise a cleavage site for removing the secretory pathway sequence from the polypeptide. In some embodiments, the cleavage site for removing the secretory pathway sequence from the polypeptide is a cleavage site for an endoprotease. In some embodiments, the cleavage site is for an endoprotease expressed by the cell in which the polypeptide is expressed. In some embodiments, the cleavage site is a signal peptidase cleavage site. In some embodiments, the cleavage site is a protease cleavage site, e.g. a cleavage site for an endoprotease expressed by cells expressing the polypeptide. In some embodiments, the cleavage site is a cleavage site for an endoprotease expressed by RPE cells.

A polypeptide according to the present invention may comprise one or more linker sequences between amino acid sequences. A linker sequence may be provided between any two or more of sequences 'A', 'B' and/or 'C'. In some embodiments, a polypeptide according to the present invention comprises, or consists of, an amino acid sequence A+B+C-[LINKER]-A+B+C. In some embodiments, a polypeptide comprises, or consists of, SEQ ID NO:14.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5, 1-10, 1-15, 1-20, 1-25, 1-30 or 1-35 amino acids.

In some embodiments, a polypeptide according to the present invention comprises a non-amino acid linker. In some embodiments, a polypeptide according to the present invention may comprise two or more polypeptides linked by conjugation, e.g. by nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

In some embodiments, a polypeptide according to the present invention comprises a cleavable linker.

It may be desirable for a polypeptide according to the present invention to lack certain properties of CR1. For example, it may be desirable for the polypeptide to lack regions that would otherwise inhibit diffusion through Bruch's membrane (BrM) or that would interfere with the action of native co-factor family proteins.

A polypeptide according to the present invention lacks the CR1 transmembrane domain (SEQ ID NO:32). A polypeptide according to the present invention may lack the CR1 cytoplasmic tail (SEQ ID NO:33). In a preferred embodiment, a polypeptide according to the present invention is soluble.

A polypeptide according to the present invention may lack regions which could otherwise be exploited by pathogenic bacteria to subvert the host immune system. Bacteria have developed molecules on their surface that can bind and recruit soluble complement factor H from the blood. This enables the bacteria to effectively coat themselves in a complement regulator and evade a host immune response. Polypeptides according to the present invention may lack bacterial binding sites such that they cannot be used by invading pathogens to evade an immune response.

In some embodiments a polypeptide according to the present invention comprises one or more sites for glycosylation. In some embodiments a polypeptide according to the present invention is glycosylated.

In some embodiments, a polypeptide according to the present invention is not glycosylated. In some embodiments, a polypeptide according to the present invention lacks one or more sites for glycosylation. In some embodiments, the polypeptide of the present invention lacks one or more sites for N-linked glycosylation. In some embodiments, a polypeptide according to the present invention lacks N-linked glycans. In some embodiments, a polypeptide according to the present invention is expressed and/or secreted by cells that are unable to glycosylate or fully glycosylate polypeptides. For example, cells may lack functional glycosyl transferase enzymes. In some embodiments, the polypeptide is aglycosyl (i.e. is not glycosylated). In some embodiments, the polypeptide has been deglycosylated, e.g. by treatment with a glycosidase (e.g. Peptide N-Glycosidase). Deglycosylation is preferably non-denaturing. In some embodiments a polypeptide according to the present invention is partially glycosylated, non-glycosylated or de-glycosylated.

In some embodiments, a polypeptide according to the present invention lacks sequence conforming to the consensus sequence of SEQ ID NO:27. In some embodiments, the polypeptide according to the present invention comprises one or more sequences conforming to the consensus sequence of SEQ ID NO:27 that have been mutated to remove sites for N-glycosylation. In some embodiments, the Asn (N) residue in one or more consensus sequences according to SEQ ID NO:27 is substituted with another amino acid residue, e.g. a residue selected from: Ala (A), Cys (C), Asp (D), Glu (E), Phe (F), Gly (G), His (H), Ile (I), Lys (K), Leu (L), Met (M), Pro (P), Gln (Q), Arg (R), Ser (S), Thr (T), Val (V), Trp (W) or Tyr (Y). In some embodiments, the Asn (N) residue in one or more consensus sequences according to SEQ ID NO:27 is substituted with a Gln (Q) residue. In some embodiments, residue $X_2$ of SEQ ID NO:27 is, or is mutated to be, an amino acid that is not Ser (S) or Thr (T).

In some embodiments, a polypeptide comprising, or consisting of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:2 or SEQ ID NO:4 comprises one or more amino acid substitutions at position 509 and/or position 578 (numbered according to Uniprot: P17927). In some embodiments, the one or more amino acid substitutions are selected from N509Q and/or N578Q. In some embodiments, a polypeptide comprising, or consisting of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:3 comprises one or more amino acid substitutions at position 959 and/or position 1028 (numbered according to Uniprot: P17927). In some embodiments, the one or more amino acid substitutions are selected from N959Q and/or N1028Q. In some embodiments, a polypeptide comprising, or consisting of, an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:13 comprises one or more amino acid substitutions at position 509, 578, 959 and/or position 1028 (numbered according to Uniprot: P17927). In some embodiments, the one or more amino acid substitutions are selected from N509Q, N578Q, N959Q and/or N1028Q. Such polypeptides may have any length provided herein.

In some embodiments, the polypeptide comprises, or consists, of an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:5, SEQ ID NO:6, SEQ ID NO:15, and/or SEQ ID NO:31. Such polypeptides may have any length provided herein.

In some embodiments a polypeptide according to the present invention comprises a secretory pathway sequence and one or more sequences conforming to the consensus sequence of SEQ ID NO:27 that have been mutated to remove sites for N-glycosylation. In some embodiments a polypeptide according to the present invention comprises, or consists of, an amino acid sequence corresponding to SEQ ID NO:48, 50, 52, 53, and/or 54. In some embodiments the polypeptide comprises, or consists, of an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:48, 50, 52, 53, and/or 54. Such polypeptides may have any length provided herein.

In some embodiments, a polypeptide according to the present invention may comprise amino acid sequence(s) to facilitate expression, folding, trafficking, processing, purification or detection of the polypeptide. For example, the polypeptide may comprise a sequence encoding a protein tag, e.g. a His, (e.g. 6×His), FLAG, Myc, GST, MBP, HA, E, or Biotin tag, optionally: at the N- or C-terminus of the polypeptide; in a linker; or at the N- or C-terminus of a linker. In some embodiments the polypeptide comprises a detectable moiety, e.g. a fluorescent, luminescent, immuno-detectable, radio, chemical, nucleic acid or enzymatic label. In some embodiments, the detectable moiety facilitates detection of the polypeptide in a sample obtained from a subject, e.g. following administration to the subject of the polypeptide, nucleic acid, vector, cell or pharmaceutical composition according to the present invention. The sample may be any biological sample obtained from a subject. In some embodiments the sample is a liquid biopsy, such as ocular fluid (tear fluid, aqueous humour, or vitreous), blood, plasma, etc. In some embodiments the sample is a cytological sample or a tissue sample such as a surgical sample, e.g. of ocular cells/tissue.

In some embodiments, the polypeptide according to the present invention may be detected and/or distinguished from endogenous CR1 by Western blotting, mass spectrometry and/or enzyme digestion, e.g. by a specific peptidase. In some embodiments, the polypeptide may comprise a point mutation to generate peptides by enzyme digestion that are distinct from post-digestion peptides from endogenous CR1.

In some embodiments, a polypeptide according to the present invention may additionally comprise a cleavage site for removing a protein tag. For example, it may be desired to remove a tag used for purification of the polypeptide following purification. In some embodiments the cleavage site may e.g. be a Tobacco Etch Virus (TEV) protease cleavage site, for example as shown in SEQ ID NO:34.

In some embodiments a polypeptide according to the present invention comprises, or consists of, an amino acid sequence corresponding to SEQ ID NO:40, 42, 44, and/or 46. In some embodiments the polypeptide comprises, or consists of, an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:40, 42, 44, and/or 46. Such polypeptides may have any length provided herein.

As used herein, a "polypeptide" includes molecules comprising more than one polypeptide chain, which may be associated (e.g. covalently or non-covalently) into a complex. That is, a "polypeptide" within the meaning of the present invention encompasses molecules comprising one or more polypeptide chains. The polypeptide of the invention may in various different embodiments and at different stages of expression/production in vitro or in vivo comprise e.g. a signal peptide, protein tag, cleavage sites for removal thereof, etc. The polypeptide of the invention may comprise any CR1 CCP sequence described herein, or any combination of CR1 CCP domains 8 (SEQ ID NO:8), 9 (SEQ ID NO:9), 10 (SEQ ID NO:10), 15 (SEQ ID NO:8), 16 (SEQ ID NO:11), and/or 17 (SEQ ID NO:12), or any combination of sequences 'A', 'B' and/or 'C' described herein, optionally in combination with one or more of any of the further features of the polypeptide of the invention described herein (e.g. signal peptide, linker, detection sequence, lack of glycosylation site, substituted amino acid residue, protein tag, cleavage site for removing a protein tag, secretory pathway sequence, cleavage site for removing a secretory pathway sequence).

Sequence Identity

As used herein, an amino acid sequence which corresponds to a reference amino acid sequence may comprise at least 60%, e.g. one of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the reference sequence.

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | Description | Sequence |
|---|---|---|
| 1 | Human Complement Receptor 1 (UniProt: P17927; Entry version 181 (25 Oct. 2017), Sequence version 3 (02 Mar. 2010)); residues 1-2039 Including signal sequence [CCP domains '8-10' and 15-17 indicated by single underline, individual CCP domains 8, 9, 10, 15, 16, 17 indicated by double underline; amino acid differences between CCPs 8-10 and 15-17 indicated with wavy underline] | MGASSPRSPEPVGPPAPGLPFCCGGSLLAVVVLLALPVAWGQCNAPEW LPFARPTNLTDEFEFPIGTYLNYECRPGYSGRPFSIICLKNSVWTGAK DRCRRKSCRNPPDPVNGMVHVIKGIQFGSQIKYSCTKGYRLIGSSSAT CIISGDTVIWDNETPICDRIPCGLPPTITNGDFISTNRENFHYGSVVT YRCNPGSGGRKVFELVGEPSIYCTSNDDQVGIWSGPAPQCIIPNKCTP PNVENGILVSDNRSLFSLNEVVEFRCQPGFVMKGPRRVKCQALNKWEP ELPSCSRVCQPPPDVLHAERTQRDKDNFSPGQEVFYSCEPGYDLRGAA SMRCTPQGDWSPAAPTCEVKSCDDFMGQLLNGRVLFPVNLQLGAKVDF VCDEGFQLKGSSASYCVLAGMESLWNSSVPVCEQIFCPSPPVIPNGRH TGKPLEVFPPFGKTVNYTCDPHPDRGTSFDLIGESTIRCTSDPQGNGVW SSPAPRCGIL<u>GHCQAPDHFLFAKLKTQTNASDFPIGTSLKYECRPEYY GRPFSITCLDNLVWSSPKDVCKRKSCKTPPDPVNGMVHVITDIQVGSR INYSCTTGHRLIGHSSAECILSGNA</u>AHWSTKPPICQRIPCGLPPTIAN GDFISTNRENFHYGSVVTYRCNP<u>GS</u>GGRKVFELVGEPSIYCTSNDDQV GIWSGPAPQCIIPNKCTPPNVENGILVSDNRSLFSLNEVVEFRCQPGF VMKGPRRVKCQALNKWEPELPSCSRVCQPPPDVLHAERTQRDKDNFSP GQEVFYSCEPGYDLRGAASMRCTPQGDWSPAAPTCEVKSCDDFMGQLL NGRVLFPVNLQLGAKVDFVCDEGFQLKGSSASYCVLAGMESLWNSSVP VCEQIFCPSPPVIPNGRHTGKPLEVFPPFGKAVNYTCDPHPDRGTSFDL IGESTIRCTSDPQGNGVWSSPAPRCGIL<u>GHCQAPDHFLFAKLKTQTNA SDFPIGTSLKYECRPEYYGRPFSITCLDNLVWSSPKDVCKRKSCKTPP DPVNGMVHVITDIQVGSRINYSCTTGHRLIGHSSAECILSGNT</u>AHWST KPPICQRIPCGLPPTIANGDFISTNRENFHYGSVVTYRCN<u>L</u>GS<u>R</u>GRKV FELVGEPSIYCTSNDDQVGIWSGPAPQCIIPNKCTPPNVENGILVSDN RSLFSLNEVVEFRCQPGFVMKGPRRVKCQALNKWEPELPSCSRVCQPP PEILHGEHTPSHQDNFSPGQEVFYSCEPGYDLRGAASLHCTPQGDWSP EAPRCAVKSCDDFLGQLPHGRVLFPLNLQLGAKVSFVCDEGFRLKGSS VSHCVLVGMRSLWNNSVPVCEHIFCPNPPAILNGRHTGTPSGDIPYGK EISYTCDPHPDRGMTFNLIGESTIRCTSDPHGNGVWSSPAPRCELSVR AGHCKTPEQFPFASPTIPINDFEFPVGTSLNYECRPGYFGKMFSISCL ENLVWSSVEDNCRRKSCGPPPEPFNGMVHINTDTQFGSTVNYSCNEGF RLIGSPSTTCLVSGNNVTWDKKAPICEIISCEPPPTISNGDFYSNNRT SFHNGTVVTYQCHTGPDGEQLFELVGERSIYCTSKDDQVGVWSSPPPR CISTNKCTAPEVENAIRVPGNRSFFSLTEIIRFRCQPGFVMVGSHTVQ CQTNGRWGPKLPHCSRVCQPPPEILHGEHTLSHQDNFSPGQEVFYSCE PSYDLRGAASLHCTPQGDWSPEAPRCTVKSCDDFLGQLPHGRVLLPLN LQLGAKVSFVCDEGFRLKGRSASHCVLAGMKALWNSSVPVCEQIFCPN PPAILNGRHTGTPFGDIPYGKEISYACDTHPDRGMTFNLIGESSIRCT SDPQGNGVWSSPAPRCELSVPAACPHPPKIQNGHYIGGHVSLYLPGMT ISYICDPGYLLVGKGFIFCTDQGIWSQLDHYCKEVNCSFPLFMNGISK ELEMKKVYHYGDYVTLKCEDGYTLEGSPWSQCQADDRWDPPLAKCTSR THDALIVGTLSGTIFFILLIIFLSWIILKHRKGNNAHENPKEVAIHLH SQGGSSVHPRTLQTNEENSRVLP |
| 2 | Human Complement Receptor 1 CCPs 8-10 (UniProt: P17927 residues 491 to 684) Without leader sequence | GHCQAPDHFLFAKLKTQTNASDFPIGTSLKYECRPEYYGRPFSITCLD NLVWSSPKDVCKRKSCKTPPDPVNGMVHVITDIQVGSRINYSCTTGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC II |
| 3 | Human Complement Receptor 1 CCPs 15-17 (UniProt: P17927 residues 941 to 1134) Without leader sequence | GHCQAPDHFLFAKLKTQTNASDFPIGTSLKYECRPEYYGRPFSITCLD NLVWSSPKDVCKRKSCKTPPDPVNGMVHVITDIQVGSRINYSCTTGHR LIGHSSAECILSGNTAHWSTKPPICQRIPCGLPPTIANGDFISTNREN FHYGSVVTYRCNLGSRGRKVFELVGEPSIYCTSNDDQVGIWSGPAPQC II |

-continued

| SEQ ID NO: | Description | Sequence |
|---|---|---|
| 4 | Human Complement Receptor 1; consensus sequence for CCPs 8-10, 15-17 (UniProt: P17927 residues 491 to 684; residues 941 to 1134) Without leader sequence | GHCQAPDHFLFAKLKTQTNASDFPIGTSLKYECRPEYYGRPFSITCLD NLVWSSPKDVCKRKSCKTPPDPVNGMVHVITDIQVGSRINYSCTIGHR LIGHSSAECILSGNX₁AHWSTKPPICQRIPCGLPPTIANGDFISTNRE NFHYGSVVTYRCNX₂GSX₃GRKVFELVGEPSIYCTSNDDQVGIWSGPAP QCII |
| 5 | Human Complement Receptor 1 CCPs 8-10 (UniProt: P17927 residues 491 to 684) Non-glycosylated; Without leader sequence [mutated glycosylation sites underlined; substitutions in bold correspond to positions 509 and 578 of UniProt: P17927] | GHCQAPDHFLFAKLKTQT<u>QAS</u>DFPIGTSLKYECRPEYYGRPFSITCLD NLVWSSPKDVCKRKSCKTPPDPVNGMVHVITDIQVGSRI<u>QYS</u>CTIGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC II |
| 6 | Human Complement Receptor 1 CCPs 15-17 (UniProt: P17927 residues 941 to 1134) Non-glycosylated; Without leader sequence [mutated glycosylation sites underlined; substitutions in bold correspond to positions 959 and 1028 of UniProt: P17927] | GHCQAPDHFLFAKLKTQT<u>QAS</u>DFPIGTSLKYECRPEYYGRPFSITCLD NLVWSSPKDVCKRKSCKTPPDPVNGMVHVITDIQVGSRI<u>QYS</u>CTIGHR LIGHSSAECILSGNTAHWSTKPPICQRIPCGLPPTIANGDFISTNREN FHYGSVVTYRCNLGSRGRKVFELVGEPSIYCTSNDDQVGIWSGPAPQC II |
| 7 | Native signal/leader sequence from Factor H | MRLLAKIICLMLWAICVA |
| 8 | Human Complement Receptor 1 CCP8/CCP15 (UniProt: P17927 residues 491-550/941-1000) 'Sequence A' | GHCQAPDHFLFAKLKTQTNASDFPIGTSLKYECRPEYYGRPFSITCLD NLVWSSPKDVCKR |
| 9 | Human Complement Receptor 1 CCP9 (UniProt: P17927 residues 552-612) | KSCKTPPDPVNGMVHVITDIQVGSRINYSCTIGHRLIGHSSAECILSG NAAHWSTKPPICQ |
| 10 | Human Complement Receptor 1 CCP10 (UniProt: P17927 residues 613-684 | RIPCGLPPTIANGDFISTNRENFHYGSVVTYRCNPGSGGRKVFELVGE PSIYCTSNDDQVGIWSGPAPQCII |
| 11 | Human Complement Receptor 1 CCP16 (UniProt: P17927 residues 1002-1062) | KSCKTPPDPVNGMVHVITDIQVGSRINYSCTIGHRLIGHSSAECILSG NTAHWSTKPPICQ |
| 12 | Human Complement Receptor 1 CCP17 (UniProt: P17927 residues 1063-1134 | RIPCGLPPTIANGDFISTNRENFHYGSVVTYRCNLGSRGRKVFELVGE PSIYCTSNDDQVGIWSGPAPQCII |

-continued

| SEQ ID NO: | Description | Sequence |
|---|---|---|
| 13 | Human Complement Receptor 1 CCPs 8-10 and 15-17 (contiguous; without leader sequence) [amino acid differences between CCPs 8-10 and 15-17 indicated with wavy underline] | GHCQAPDHFLFAKLKTQTNASDFPIGTSLKYECRPEYYGRPFSITCLD NLVWSSPKDVCKRKSCKIPPDPVNGMVHVITDIQVGSRINYSCTIGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC IIGHCQAPDHFLFAKLKTQTNASDFPIGTSLKYECRPEYYGRPFSITC LDNLVWSSPKDVCKRKSCKTPPDPVNGMVHVITDIQVGSRINYSCITG HRLIGHSSAECILSGNTAHWSTKPPICQRIPCGLPPTIANGDFISTNR ENFHYGSVVTYRCNLGSRGRKVFELVGEPSIYCTSNDDQVGIWSGPAP QCII |
| 14 | Human Complement Receptor 1 CCPs 8-10 (linker) 15-17 | GHCQAPDHFLFAKLKTQTNASDFPIGTSLKYECRPEYYGRPFSITCLD NLVWSSPKDVCKRKSCKIPPDPVNGMVHVITDIQVGSRINYSCTIGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC II-[linker]- GHCQAPDHFLFAKLKTQTNASDFPIGTSLKYECRPEYYGRPFSITCLD NLVWSSPKDVCKRKSCKIPPDPVNGMVHVITDIQVGSRINYSCTIGHR LIGHSSAECILSGNTAHWSTKPPICQRIPCGLPPTIANGDFISTNREN FHYGSVVTYRCNLGSRGRKVFELVGEPSIYCTSNDDQVGIWSGPAPQC II |
| 15 | Human Complement Receptor 1 CCPs 8-10 and 15-17 (contiguous) Non-glycosylated; Without leader sequence [Mutated glycosylation sites underlined; substitutions in bold correspond to positions 509, 578, 959 and 1028 of UniProt: P17927] | GHCQAPDHELFAKLKTQTQASDEPIGTSLKYECRPEYYGRPFSITCLD NLVWSSPKDVCKRKSCKIPPDPVNGMVHVITDIQVGSRIQYSCTIGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC IIGHCQAPDHFLFAKLKTQTQASDFPIGTSLKYECRPEYYGRPFSITC LDNLVWSSPKDVCKRKSCKIPPDPVNGMVHVITDIQVGSRIQYSCITG HRLIGHSSAECILSGNTAHWSTKPPICQRIPCGLPPTIANGDFISTNR ENFHYGSVVTYRCNLGSRGRKVFELVGEPSIYCTSNDDQVGIWSGPAP QCII |
| 16 | Human Complement Receptor 1; Consensus sequence for CCPs 9, 16 (corresponding to UniProt: P17927 residues 552-612 and 1002-1062) 'Sequence B' | KSCKIPPDPVNGMVHVITDIQVGSRINYSCTIGHRLIGHSSAECILSG NX$_1$AHWSTKPPICQ |
| 17 | Human Complement Receptor 1; Consensus sequence for CCPs 10, 17 (corresponding to (UniProt: P17927 residues 613-684 and 1063-1134) 'Sequence C' | RIPCGLPPTIANGDFISTNRENFHYGSVVTYRCNX$_2$GSX$_3$GRKVFELVG EPSIYCTSNDDQVGIWSGPAPQCII |
| 18 | Human C3 (UniProt: P01024; Entry version 221 (20 Dec. 2017); Sequence version 2 (12 Dec. 2006)) including signal peptide | MGPTSGPSLLLLLLTHLPLALGSPMYSIITPNILRLESEETMVLEAHD AQGDVPVIVIVHDFPGKKLVLSSEKTVLIPAINHMGNVIFTIPANREF KSEKGRNKFVTVQATFGTQVVEKVVLVSLQSGYLFIQTDKTIYIPGST VLYRIFTVNHKLLPVGRIVMVNIENPEGIPVKQDSLSSQNQLGVLPLS WDIPELVNMGQWKIRAYYENSPQQVFSTEFEVKEYVLPSFEVIVEPTE KFYYIYNEKGLEVTITARFLYGKKVEGTAFVIFGIQDGEQRISLPESL KRIPIEDGSGEVVLSRKVLLDGVQNPRAEDLVGKSLYVSATVILHSGS DMVQAERSGIPIVISPYQIHFIKTPKYFKPGMPFDLMVFVINPDGSPA YRVPVAVQGEDTVQSLIQGDGVAKLSINTHPSQKPLSITVRIKKQELS EAEQATRTMQALPYSTVGNSNNYLHLSVLRTELRPGETLNVNFLLRMD RAHEAKIRYYTYLIMNKGRLLKAGRQVREPGQDLVVLPLSITTDFIPS FRLVAYYTLIGASGQREVVADSVWVDVKDSCVGSLVVKSGQSEDRQPV PGQQMTLKIEGDHGARVVLVAVDKGVFVLNKKNKLTQSKIWDVVEKAD IGCTPGSGKDYAGVFSDAGLTFTSSSGQQTAQRAELQCPQPAARRRRS VQLTEKRMDKVGKYPKELRKCCEDGMRENPMRFSCQRRTRFISLGEAC KKVFLDCCNYITELRRQHARASHLGLARSNLDEDIIAEENIVSRSEFP ESWLWNVEDLKEPPKNGISTKLMNIFLKDSITTWEILAVSMSDKKGIC VADPFEVTVMQDFFIDLRLPYSVVRNEQVEIRAVLYNYRQNQELKVRV ELLHNPAFCSLATTKRRHQQTVTIPPKSSLSVPYVIVPLKTGLQEVEV KAAVYHHFISDGVRKSLKVVPEGIRMNKTVAVRTLDPERLGREGVQKE DIPPADLSDQVPDTESETRILLQGTPVAQMTEDAVDAERLKHLIVTPS |

| SEQ ID NO: | Description | Sequence |
|---|---|---|
|  |  | GCGEQNMIGMTPTVIAVHYLDETEQWEKFGLEKRQGALELIKKGYTQQ LAFRQPSSAFAAFVKRAPSTWLTAYVVKVFSLAVNLIAIDSQVLCGAV KWLILEKQKPDGVFQEDAPVIHQEMIGGLRNNNEKDMALTAFVLISLQ EAKDICEEQVNSLPGSITKAGDFLEANYMNLQRSYTVAIAGYALAQMG RLKGPLLNKFLTTAKDKNRWEDPGKQLYNVEATSYALLALLQLKDFDF VPPVVRWLNEQRYYGGGYGSTQATFMVFQALAQYQKDAPDHQELNLDV SLQLPSRSSKITHRIHWESASLLRSEETKENEGFTVTAEGKGQGTLSV VTMYHAKAKDQLTCNKFDLKVTIKPAPETEKRPQDAKNTMILEICTRY RGDQDATMSILDISMMTGFAPDTDDLKQLANGVDRYISKYELDKAFSD RNTLIIYLDKVSHSEDDCLAFKVHQYFNVELIQPGAVKVYAYYNLEES CTRFYHPEKEDGKLNKLCRDELCRCAEENCFIQKSDDKVTLEERLDKA CEPGVDYVYKTRLVKVQLSNDFDEYIMAIEQTIKSGSDEVQVGQQRTF ISPIKCREALKLEEKKHYLMWGLSSDFWGEKPNLSYIIGKDTWVEHWP EEDECQDEENQKQCQDLGAFTESMVVFGCPN |
| 19 | Human C3 β chain (UniProt: P01024; Entry version 221 (20 Dec. 2017); Sequence version 2 (12 Dec. 2006); residues 23-667) | SPMYSIITPNILRLESEETMVLEAHDAQGDVPVTVTVHDFPGKKLVLS SEKTVLTPATNHMGNVTFTIPANREFKSEKGRNKFVTVQATFGTQVVE KVVLVSLQSGYLFIQTDKTIYTPGSTVLYRIFTVNHKLLPVGRTVMVN IENPEGIPVKQDSLSSQNQLGVLPLSWDIPELVNMGQWKIRAYYENSP QQVFSTEFEVKEYVLPSFEVIVEPTEKFYYIYNEKGLEVTITARFLYG KKVEGTAFVIFGIQDGEQRISLPESLKRIPIEDGSGEVVLSRKVLLDG VQNPRAEDLVGKSLYVSATVILHSGSDMVQAERSGIPIVTSPYQIHFT KTPKYFKPGMPFDLMVFVTNPDGSPAYRVPVAVQGEDTVQSLTQGDGV AKLSINTHPSQKPLSITVRTKKQELSEAEQATRTMQALPYSTVGNSNN YLHLSVLRTELRPGETLNVNFLLRMDRAHEAKIRYYTYLIMNKGRLLK AGRQVREPGQDLVVLPLSITTDFIPSFRLVAYYTLIGASGQREVVADS VWVDVKDSCVGSLVVKSGQSEDRQPVPGQQMTLKIEGDHGARVVLVAV DKGVFVLNKKNKLTQSKIWDVVEKADIGCTPGSGKDYAGVFSDAGLTF TSSSGQQTAQRAELQCPQPAA |
| 20 | Human C3 α' chain (UniProt: P01024; Entry version 221 (20 Dec. 2017); Sequence version 2 (12 Dec. 2006); residues 749-1663) | SNLDEDIIAEENIVSRSEFPESWLWNVEDLKEPPKNGISTKLMNIFLK DSITTWEILAVSMSDKKGICVADPFEVTVMQDFFIDLRLPYSVVRNEQ VEIRAVLYNYRQNQELKVRVELLHNPAFCSLATTKRRHQQTVTIPPKS SLSVPYVIVPLKTGLQEVEVKAAVYHHFISDGVRKSLKVVPEGIRMNK TVAVRTLDPERLGREGVQKEDIPPADLSDQVPDTESETRILLQGTPVA QMTEDAVDAERLKHLIVTPSGCGEQNMIGMTPTVIAVHYLDETEQWEK FGLEKRQGALELIKKGYTQQLAFRQPSSAFAAFVKRAPSTWLTAYVVK VFSLAVNLIAIDSQVLCGAVKWLILEKQKPDGVFQEDAPVIHQEMIGG LRNNNEKDMALTAFVLISLQEAKDICEEQVNSLPGSITKAGDFLEANY MNLQRSYTVAIAGYALAQMGRLKGPLLNKFLTTAKDKNRWEDPGKQLY NVEATSYALLALLQLKDFDFVPPVVRWLNEQRYYGGGYGSTQATFMVF QALAQYQKDAPDHQELNLDVSLQLPSRSSKITHRIHWESASLLRSEET KENEGFTVTAEGKGQGTLSVVTMYHAKAKDQLTCNKFDLKVTIKPAPE TEKRPQDAKNTMILEICTRYRGDQDATMSILDISMMTGFAPDTDDLKQ LANGVDRYISKYELDKAFSDRNTLIIYLDKVSHSEDDCLAFKVHQYFN VELIQPGAVKVYAYYNLEESCTRFYHPEKEDGKLNKLCRDELCRCAEE NCFIQKSDDKVTLEERLDKACEPGVDYVYKTRLVKVQLSNDFDEYIMA IEQTIKSGSDEVQVGQQRTFISPIKCREALKLEEKKHYLMWGLSSDFW GEKPNLSYIIGKDTWVEHWPEEDECQDEENQKQCQDLGAFTESMVVFG CPN |
| 21 | Human C3a (UniProt: P01024; Entry version 221 (20 Dec. 2017); Sequence version 2 (12 Dec. 2006); residues 672-748) | SVQLTEKRMDKVGKYPKELRKCCEDGMRENPMRFSCQRRTRFISLGEA CKKVFLDCCNYITELRRQHARASHLGLAR |
| 22 | Human C3 α' chain fragment 1 (UniProt: P01024; Entry version 221 (20 Dec. 2017); Sequence version 2 (12 Dec. 2006); residues 749-1303) | SNLDEDIIAEENIVSRSEFPESWLWNVEDLKEPPKNGISTKLMNIFLK DSITTWEILAVSMSDKKGICVADPFEVTVMQDFFIDLRLPYSVVRNEQ VEIRAVLYNYRQNQELKVRVELLHNPAFCSLATTKRRHQQTVTIPPKS SLSVPYVIVPLKTGLQEVEVKAAVYHHFISDGVRKSLKVVPEGIRMNK TVAVRTLDPERLGREGVQKEDIPPADLSDQVPDTESETRILLQGTPVA QMTEDAVDAERLKHLIVTPSGCGEQNMIGMTPTVIAVHYLDETEQWEK FGLEKRQGALELIKKGYTQQLAFRQPSSAFAAFVKRAPSTWLTAYVVK VFSLAVNLIAIDSQVLCGAVKWLILEKQKPDGVFQEDAPVIHQEMIGG LRNNNEKDMALTAFVLISLQEAKDICEEQVNSLPGSITKAGDFLEANY MNLQRSYTVAIAGYALAQMGRLKGPLLNKFLTTAKDKNRWEDPGKQLY NVEATSYALLALLQLKDFDFVPPVVRWLNEQRYYGGGYGSTQATFMVF QALAQYQKDAPDHQELNLDVSLQLPSR |

-continued

| SEQ ID NO: | Description | Sequence |
|---|---|---|
| 23 | Human C3 α' chain fragment 2 (UniProt: P01024;; Entry version 221 (20 Dec. 2017); Sequence version 2 (12 Dec. 2006); residues 1321-1663) Also known as C3c fragment 2 | SEETKENEGFTVTAEGKGQGTLSVVTMYHAKAKDQLTCNKFDLKVTIK PAPETEKRPQDAKNTMILEICTRYRGDQDATMSILDISMMTGFAPDTD DLKQLANGVDRYISKYELDKAFSDRNTLIIYLDKVSHSEDDCLAFKVH QYFNVELIQPGAVKVYAYYNLEESCTRFYHPEKEDGKLNKLCRDELCR CAEENCFIQKSDDKVTLEERLDKACEPGVDYVYKTRLVKVQLSNDFDE YIMAIEQTIKSGSDEVQVGQQRTFISPIKCREALKLEEKKHYLMWGLS SDFWGEKPNLSYIIGKDTWVEHWPEEDECQDEENQKQCQDLGAFTESM VVFGCPN |
| 24 | Human C3f (UniProt: P01024;; Entry version 221 (20 Dec. 2017); Sequence version 2 (12 Dec. 2006); residues 1304-1320) | SSKITHRIHWESASLLR |
| 25 | Human Complement Factor I (UniProt: P05156; Entry version 192 (20 Dec. 2017) Sequence version 2 (11 Jan. 2011)) | MKLLHVFLLFLCFHLRFCKVTYTSQEDLVEKKCLAKKYTHLSCDKVFC QPWQRCIEGTCVCKLPYQCPKNGTAVCATNRRSFPTYCQQKSLECLHP GTKFLNNGTCTAEGKFSVSLKHGNTDSEGIVEVKLVDQDKTMFICKSS WSMREANVACLDLGFQQGADTQRRFKLSDLSINSTECLHVHCRGLETS LAECTFTKRRTMGYQDFADVVCYTQKADSPMDDFFQCVNGKYISQMKA CDGINDCGDQSDELCCKACQGKGFHCKSGVCIPSQYQCNGEVDCITGE DEVGCAGFASVTQEETEILTADMDAERRRIKSLLPKLSCGVKNRMHIR RKRIVGGKRAQLGDLPWQVAIKDASGITCGGIYIGGCWILTAAHCLRA SKTHRYQIWTTVVDWIHPDLKRIVIEYVDRIIFHENYNAGTYQNDIAL IEMKKDGNKKDCELPRSIPACVPWSPYLFQPNDTCIVSGWGREKDNER VFSLQWGEVKLISNCSKFYGNRFYEKEMECAGTYDGSIDACKGDSGGP LVCMDANNVTYVWGVVSWGENCGKPEFPGVYTKVANYFDWISYHVGRP FISQYNV |
| 26 | Human Complement Factor I proteolytic domain (UniProt: P05156; Entry version 192 (20 Dec. 2017) Sequence version 2 (11 Jan. 2011); residues 340-574) | IVGGKRAQLGDLPWQVAIKDASGITCGGIYIGGCWILTAAHCLRASKT HRYQIWTTVVDWIHPDLKRIVIEYVDRIIFHENYNAGTYQNDIALIEM KKDGNKKDCELPRSIPACVPWSPYLFQPNDTCIVSGWGREKDNERVFS LQWGEVKLISNCSKFYGNRFYEKEMECAGTYDGSIDACKGDSGGPLVC MDANNVTYVWGVVSWGENCGKPEFPGVYTKVANYFDWISYHVG |
| 27 | Consensus sequence for N-linked glycosylation | $NX_1X_2$<br>wherein<br>$X_1$ = any amino acid except for P<br>$X_2$ = S or T |
| 28 | Complement Factor H isoform FHL-1 (UniProt: P08603-2) Including leader sequence (underlined) SEQ ID No. 7 | <u>MRLLAKIICLMLWAIC</u>VAEDCNELPPRRNTEILTGSWSDQTYPEGTQA IYKCRPGYRSLGNVIMVCRKGEWVALNPLRKCQKRPCGHPGDTPFGTF TLTGGNVFEYGVKAVYTCNEGYQLLGEINYRECDTDGWTNDIPICEVV KCLPVTAPENGKIVSSAMEPDREYHFGQAVRFVCNSGYKIEGDEEMHC SDDGFWSKEKPKCVEISCKSPDVINGSPISQKIIYKENERFQYKCNMG YEYSERGDAVCTESGWRPLPSCEEKSCDNPYIPNGDYSPLRIKHRTGD EITYQCRNGFYPATRGNTAKCTSTGWIPAPRCTLKPCDYPDIKHGGLY HENMRRPYFPVAVGKYYSYYCDEHFETPSGSYWDHIHCTQDGWSPAVP CLRKCYFPYLENGYNQNYGRKFVQGKSIDVACHPGYALPKAQTTVTCM ENGWSPTPRCIRVSFTL |
| 29 | Human Complement Factor H (UniProt: P08603; Entry version 214 (25 Oct. 2017) Sequence version 4 (11 Sep. 2007)) Including leader sequence (underlined) SEQ ID No. 7 | <u>MRLLAKIICLMLWAIC</u>VAEDCNELPPRRNTEILTGSWSDQTYPEGTQA TYKCRPGYRSLGNVIMVCRKGEWVALNPLRKCQKRPCGHPGDTPFGTF TLTGGNVFEYGVKAVYTCNEGYQLLGEINYRECDTDGWTNDIPICEVV KCLPVTAPENGKIVSSAMEPDREYHFGQAVREVCNSGYKIEGDEEMHC SDDGEWSKEKPKCVEISCKSPDVINGSPISQKITYKENERFQYKCNMG YEYSERGDAVCTESGWRPLPSCEEKSCDNPYIPNGDYSPLRIKHRTGD EITYQCRNGFYPATRGNTAKCTSTGWIPAPRCTLKPCDYPDIKHGGLY HENMRRPYFPVAVGKYYSYYCDEHFETPSGSYWDHIHCTQDGWSPAVP CLRKCYFPYLENGYNQNYGRKFVQGKSIDVACHPGYALPKAQTTVTCM ENGWSPTPRCIRVKTCSKSSIDIENGFISESQYTYALKEKAKYQCKLG YVTADGETSGSITCGKDGWSAQPTCIKSCDIPVFMNARTKNDFTWFKL NDTLDYECHDGYESNTGSTTGSIVCGYNGWSDLPICYERECELPKIDV HLVPDRKKDQYKVGEVLKFSCKPGFTIVGPNSVQCYHFGLSPDLPICK EQVQSCGPPPELLNGNVKEKTKEEYGHSEVVEYYCNPRFLMKGPNKIQ CVDGEWTTLPVCIVEESTCGDIPELEHGWAQLSSPPYYYGDSVEFNCS ESFTMIGHRSITCIHGVWTQLPQCVAIDKLKKCKSSNLIILEEHLKNK KEEDHNSNIRYRCRGKEGWIHTVCINGRWDPEVNCSMAQIQLCPPPPQ |

-continued

| SEQ ID NO: | Description | Sequence |
|---|---|---|
| | | IPNSHNMTTTLNYRDGEKVSVLCQENYLIQEGEEITCKDGRWQSIPLC VEKIPCSQPPQIEHGTINSSRSSQESYAHGTKLSYTCEGGFRISEENE TTCYMGKWSSPPQCEGLPCKSPPEISHGVVAHMSDSYQYGEEVTYKCF EGEGIDGPAIAKCLGEKWSHPPSCIKTDCLSLPSFENAIPMGEKKDVY KAGEQVTYTCATYYKMDGASNVTCINSRWTGRPTCRDTSCVNPPTVQN AYIVSRQMSKYPSGERVRYQCRSPYEMFGDEEVMCLNGNWTEPPQCKD STGKCGPPPPIDNGDITSFPLSVYAPASSVEYQCQNLYQLEGNKRITC RNGQWSEPPKCLHPCVISREIMENYNIALRWTAKQKLYSRTGESVEFV CKRGYRLSSRSHTLRTTCWDGKLEYPTCAKR |
| 30 | Human Complement Receptor 1 (UniProt: P17927 residues 491 to 1134, from CCP8 to CCP17) [CCP domains '8-10' and '15-17' indicated by single underline, individual CCP domains 8, 9, 10, 15, 16, 17 indicated by double underline; amino acid differences between CCPs 8-10 and 15-17 indicated in bold/wavy underline] | GHCQAPDHELFAKLKTQTNASDEPIGTSLKYECRPEYYGRPFSITCLD NLVWSSPKDVCKRKSCKTPPDPVNGMVHVITDIQVGSRINYSCTTGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC IIPNKCTPPNVENGILVSDNRSLFSLNEVVEFRCQPGFVMKGPRRVKC QALNKWEPELPSCSRVCQPPPDVLHAERTQRDKDNESPGQEVEYSCEP GYDLRGAASMRCTPQGDWSPAAPTCEVKSCDDFMGQLLNGRVLFPVNL QLGAKVDFVCDEGFQLKGSSASYCVLAGMESLWNSSVPVCEQIFCPSP PVIPNGRHTKPLEVPFGKAVNYTCDPHPDRGTSFDLIGESTIRCTS DPQGNGVWSSPAPRCGILGHCQAPDHELFAKLKTQTNASDEPIGTSLK YECRPEYYGRPFSITCLDNLVWSSPKDVCKRKSCKTPPDPVNGMVHVI TDIQVGSRINYSCTTGHRLIGHSSAECILSGNTAHWSTKPPICQRIPC GLPPTIANGDFISTNRENFHYGSVVTYRCNLGSRGRKVFELVGEPSIY CTSNDDQVGIWSGPAPQCII |
| 31 | Human Complement Receptor 1 (UniProt: P17927 residues 491 to 1134, CCP8 to CCP17) Non-glycosylated [CCP domains '8-10' and '15-17' indicated by single underline, individual CCP domains 8, 9, 10, 15, 16, 17 indicated by double underline; amino acid differences between CCPs 8-10 and 15-17 indicated in bold/wavy underline; substitutions in bold/dotted underline correspond to positions 509, 578, 959 and 1028 of UniProt: P17927]] | GHCQAPDHELFAKLKTQTQASDEPIGTSLKYECRPEYYGRPFSITCLD NLVWSSPKDVCKRKSCKTPPDPVNGMVHVITDIQVGSRIQYSCTTGHR LIGHSSAECILSGNAAHWSTKPPICQRIPCGLPPTIANGDFISTNREN FHYGSVVTYRCNPGSGGRKVFELVGEPSIYCTSNDDQVGIWSGPAPQC IIPNKCTPPNVENGILVSDNRSLFSLNEVVEFRCQPGFVMKGPRRVKC QALNKWEPELPSCSRVCQPPPDVLHAERTQRDKDNESPGQEVEYSCEP GYDLRGAASMRCTPQGDWSPAAPTCEVKSCDDFMGQLLNGRVLFPVNL QLGAKVDFVCDEGFQLKGSSASYCVLAGMESLWNSSVPVCEQIFCPSP PVIPNGRHTKPLEVPFGKAVNYTCDPHPDRGTSFDLIGESTIRCTS DPQGNGVWSSPAPRCGILGHCQAPDHELFAKLKTQTQASDEPIGTSLK YECRPEYYGRPFSITCLDNLVWSSPKDVCKRKSCKTPPDPVNGMVHVI TDIQVGSRIQYSCTTGHRLIGHSSAECILSGNTAHWSTKPPICQRIPC GLPPTIANGDFISTNRENFHYGSVVTYRCNLGSRGRKVFELVGEPSIY CTSNDDQVGIWSGPAPQCII |
| 32 | Human Complement Receptor 1 (UniProt: P17927; Entry version 181 (25 Oct. 2017), Sequence version 3 (02 Mar. 2010)) Transmembrane domain (residues 1972-1996 | ALIVGTLSGTIFFILLIIFLSWITL |
| 33 | Human Complement Receptor 1 (UniProt: P17927; Entry version 181 (25 Oct. 2017), Sequence version 3 (02 Mar. 2010)) Cytoplasmic tail (residues 1997-2039) | KHRKGNNAHENPKEVAIHLHSQGGSSVHPRTLQTNEENSRVLP |
| 34 | Tobacco Etch Virus (TEV) cleavage site | ENLYFQGS |
| 35 | Human Complement Receptor 1 CCPs 8-10 protein coding sequence Including leader sequence (double underlined) | AAGCTTGCCACCATGAGACTGCTGGCCAAGATCATCTGCCTGATGCTG TGGGCCATCTGCGTGGCCGGACATTGTCAGGCCCCTGACCACTTCCTG TTCGCCAAGCTGAAAACCCAGACCAACGCCAGCGACTTCCCTATCGGC ACCAGCCTGAAGTACGAGTGCAGACCCGAGTACTACGGCAGACCCTTC AGCATCACCTGTCTGGACAACCTCGTGTGGTCTAGCCCCAAGGACGTG TGCAAGAGAAAGAGCTGCAAGACCCCTCCTGATCCTGTGAACGGCATG |

| SEQ ID NO: | Description | Sequence |
|---|---|---|
|  | Including HindIII restriction enzyme cleavage site (AAGCTT), Kozak consensus sequence (GCCACC), stop codon (TAA) and EcoRV restriction enzyme cleavage site (GATATC) | GTGCACGTGATCACCGACATCCAAGTGGGCAGCAGAATCAACTACAGC TGCACCACCGGCCACAGACTGATCGGACACTCTAGCGCCGAGTGTATC CTGAGCGGCAATGCCGCACACTGGTCCACCAAGCCTCCAATCTGCCAG AGAATCCCTTGCGGCCTGCCTCCTACAATCGCCAACGGCGATTTCATC AGCACCAACAGAGAGAACTTCCACTACGGCTCCGTGGTCACCTACAGA TGCAATCCTGGCAGCGGCGGCAGAAAGGTGTTCGAACTTGTGGGCGAG CCCAGCATCTACTGCACCAGCAACGATGACCAAGTCGGCATTTGGAGC GGCCCTGCTCCTCAGTGCATCATCTAAGATATC |
| 36 | Human Complement Receptor 1 CCPs 8-10 protein coding sequence (underlined) Non-glycosylated Including leader sequence (double underlined) Including HindIII restriction enzyme cleavage site (AAGCTT), Kozak consensus sequence (GCCACC), stop codon (TAA) and EcoRV restriction enzyme cleavage site (GATATC) | AAGCTTGCCACCATGAGACTGCTGGCCAAGATCATCTGCCTGATGCTG TGGGCCATCTGCGTGGCCGGACATTGTCAGGCCCCTGACCACTTCCTG TTCGCCAAGCTGAAAACCCAGACACAGGCCAGCGACTTCCCTATCGGC ACCAGCCTGAAGTACGAGTGCAGACCCGAGTACTACGGCAGACCCTTC AGCATCACCTGTCTGGACAACCTCGTGTGGTCTAGCCCCAAGGACGTG TGCAAGAGAAAGAGCTGCAAGACCCCTCCTGATCCTGTGAACGGCATG GTGCACGTGATCACCGACATCCAAGTGGGCAGCAGAATCCAGTACAGC TGCACCACAGGCCACAGACTGATCGGCCACTCTAGCGCCGAGTGTATC CTGTCTGGCAATGCCGCTCACTGGTCCACCAAGCCTCCAATCTGCCAG AGAATCCCTTGCGGCCTGCCTCCTACAATCGCCAACGGCGATTTCATC AGCACCAACAGAGAGAACTTCCACTACGGCTCCGTGGTCACCTACAGA TGCAATCCTGGCAGCGGCGGCAGAAAGGTGTTCGAACTTGTGGGCGAG CCCAGCATCTACTGCACCAGCAACGATGACCAAGTCGGCATTTGGAGC GGCCCTGCTCCTCAGTGCATCATCTAAGATATC |
| 37 | Human Complement Receptor 1 CCPs 15-17 protein coding sequence (underlined) Including leader sequence (double underlined) Including HindIII restriction enzyme cleavage site (AAGCTT), Kozak consensus sequence (GCCACC), stop codon (TAA) and EcoRV restriction enzyme cleavage site (GATATC) | AAGCTTGCCACCATGAGACTGCTGGCCAAGATCATCTGCCTGATGCTG TGGGCCATCTGCGTGGCCGGCCACTGTCAGGCCCCTGATCACTTCCTG TTCGCCAAGCTGAAAACCCAGACCAACGCCAGCGACTTCCCTATCGGC ACCAGCCTGAAGTACGAGTGCAGACCCGAGTACTACGGCAGACCCTTC AGCATCACCTGTCTGGACAACCTCGTGTGGTCTAGCCCCAAGGACGTG TGCAAGAGAAAGAGCTGCAAGACCCCTCCTGATCCTGTGAACGGCATG GTGCACGTGATCACCGACATCCAAGTGGGCAGCAGAATCAACTACAGC TGCACCACCGGCCACAGACTGATCGGACACTCTAGCGCCGAGTGTATC CTGAGCGGCAATGCCGCACACTGGTCCACCAAGCCTCCAATCTGCCAG AGAATCCCTTGCGGCCTGCCTCCTACAATCGCCAACGGCGATTTCATC AGCACCAACAGAGAGAACTTCCACTACGGCTCCGTGGTCACCTACAGA TGCAATCCTGGCAGCGGCGGCAGAAAGGTGTTCGAACTTGTGGGCGAG CCCAGCATCTACTGCACCAGCAACGATGACCAAGTCGGCATTTGGAGC GGCCCTGCTCCTCAGTGCATCATCCCTAAGATATC |
| 38 | Human Complement Receptor 1 CCPs 15-17 protein coding sequence (underlined) Non-glycosylated Including leader sequence (double underlined) Including HindIII restriction enzyme cleavage site (AAGCTT), Kozak consensus sequence (GCCACC), stop codon (TAA) and EcoRV restriction enzyme cleavage site (GATATC) | AAGCTTGCCACCATGAGACTGCTGGCCAAGATCATCTGCCTGATGCTG TGGGCCATCTGCGTGGCCGGCCACTGTCAGGCCCCTGATCACTTCCTG TTCGCCAAGCTGAAAACCCAGACACAGGCCAGCGACTTCCCTATCGGC ACCAGCCTGAAGTACGAGTGCAGACCCGAGTACTACGGCAGACCCTTC AGCATCACCTGTCTGGACAACCTCGTGTGGTCTAGCCCCAAGGACGTG TGCAAGAGAAAGAGCTGCAAGACCCCTCCTGATCCTGTGAACGGCATG GTGCACGTGATCACCGACATCCAAGTGGGCAGCAGAATCCAGTACAGC TGCACCACAGGCCACAGACTGATCGGCCACTCTAGCGCCGAGTGTATC CTGAGCGGAAACACAGCCCACTGGTCCACCAAGCCTCCAATCTGCCAG AGAATCCCTTGCGGCCTGCCTCCTACAATCGCCAACGGCGATTTCATC AGCACCAACAGAGAGAACTTCCACTACGGCTCCGTGGTCACCTACAGA TGCAACCTGGGCTCCAGAGGCCGAAGGTGTTCGAACTTGTGGGCGAG CCTAGCATCTACTGCACCAGCAACGACGACCAAGTCGGCATTTGGAGC GGACCTGCTCCTCAGTGCATCATCCCTAAGATATC |

| SEQ ID NO: | Description | Sequence |
|---|---|---|
| 39 | Human Complement Receptor 1 CCPs 8-10 protein coding sequence (underlined) Including leader sequence (doubled underlined); His tag (dotted line); TEV cleavage site (dashed line) Including HindIII restriction enzyme cleavage site (AAGCTT), Kozak consensus sequence (GCCACC), stop codon (TAA) and EcoRV restriction enzyme cleavage site (GATATC) | AAGCTTGCCACC<u>ATGAGACTGCTGGCCAAGATCATCTGCCTGATGCTG TGGGCCATCTGCGTGGCC</u>CACCACCATCACCATCAC<u>GGCAGCAGC</u><span style="border-bottom: 1px dashed">GAG AACCTGTACTTCCAAGGATCTT</span>CTGGC<u>GGCCACTGTCAGGCCCCTGAT CACTTCCTGTTCGCCAAGCTGAAAACCCAGACCAACGCCAGCGACTTC CCTATCGGCACCAGCCTGAAGTACGAGTGCAGACCCGAGTACTACGGC AGACCCTTCAGCATCACCTGTCTGGACAACCTCGTGTGGTCTAGCCCC AAGGACGTGTGCAAGAGAAAGAGCTGCAAGACCCCTCCTGATCCTGTG AACGGCATGGTGCACGTGATCACCGACATCCAAGTGGGCAGCAGAATC AACTACAGCTGCACCACCGGCCACAGACTGATCGGACACTCTAGCGCC GAGTGTATCCTGAGCGGCAATGCCGCACACTGGTCCACCAAGCCTCCA ATCTGCCAGAGAATCCCTTGCGGCCTGCCTCCTACAATCGCCAACGGC GATTTCATCAGCACCAACAGAGAGAACTTCCACTACGGCTCCGTGGTC ACCTACAGATGCAATCCTGGCAGCGGCGGCAGAAAGGTGTTCGAACTT GTGGGCGAGCCCAGCATCTACTGCACCAGCAACGATGACCAAGTCGGC ATTTGGAGCGGCCCTGCTCCTCAGTGCATCATCTAAGATATC</u> |
| 40 | Human Complement Receptor 1 CCPs 8-10 Including leader sequence (doubled underlined); His tag (dotted line); TEV cleavage site (dashed line) | <u>MRLLAKIICLMLWAICVA</u><span style="border-bottom: 1px dotted">HHHHHH</span>GSS<span style="border-bottom: 1px dashed">ENLYFQGS</span>SGGHCQAPDHFLF AKLKTQTNASDFPIGTSLKYECRPEYYGRPFSITCLDNLVWSSPKDVC KRKSCKTPPDPVNGMVHVITDIQVGSRINYSCTTGHRLIGHSSAECIL SGNAAHWSTKPPICQRIPCGLPPTIANGDFISTNRENFHYGSVVTYRC NPGSGGRKVFELVGEPSIYCTSNDDQVGIWSGPAPQCII |
| 41 | Human Complement Receptor 1 CCPs 8-10 protein coding sequence (underlined) Non-glycosylated Including leader sequence (doubled underlined); His tag (dotted line); TEV cleavage site (dashed line) Including HindIII restriction enzyme cleavage site (AAGCTT), Kozak consensus sequence (GCCACC), stop codon (TAA) and EcoRV restriction enzyme cleavage site (GATATC) | AAGCTTGCCACC<u>ATGAGACTGCTGGCCAAGATCATCTGCCTGATGCTG TGGGCCATCTGCGTGGCC</u>CACCACCATCACCATCAC<u>GGCAGCAGC</u><span style="border-bottom: 1px dashed">GAG AACCTGTACTTCCAAGGATC</span>TTCTGGC<u>GGCCACTGTCAGGCCCCTGAT CACTTCCTGTTCGCCAAGCTGAAAACCCAGACACAGGCCAGCGACTTC CCTATCGGCACCAGCCTGAAGTACGAGTGCAGACCCGAGTACTACGGC AGACCCTTCAGCATCACCTGTCTGGACAACCTCGTGTGGTCTAGCCCC AAGGACGTGTGCAAGAGAAAGAGCTGCAAGACCCCTCCTGATCCTGTG AACGGCATGGTGCACGTGATCACCGACATCCAAGTGGGCAGCAGAATC CAGTACAGCTGCACCACAGGCCACAGACTGATCGGCCACTCTAGCGCC GAGTGTATCCTGTCTGGCAATGCCGCTCACTGGTCCACCAAGCCTCCA ATCTGCCAGAGAATCCCTTGCGGCCTGCCTCCTACAATCGCCAACGGC GATTTCATCAGCACCAACAGAGAGAACTTCCACTACGGCTCCGTGGTC ACCTACAGATGCAATCCTGGCAGCGGCGGCAGAAAGGTGTTCGAACTT GTGGGCGAGCCCAGCATCTACTGCACCAGCAACGATGACCAAGTCGGC ATTTGGAGCGGCCCTGCTCCTCAGTGCATCATCTAAGATATC</u> |
| 42 | Human Complement Receptor 1 CCPs 8-10 Non-glycosylated Including leader sequence (doubled underlined); His tag (dotted line); TEV cleavage site (dashed line) | <u>MRLLAKIICLMLWAICVA</u><span style="border-bottom: 1px dotted">HHHHHH</span>GSS<span style="border-bottom: 1px dashed">ENLYFQGS</span>SGGHCQAPDHFLF AKLKTQTQASDFPIGTSLKYECRPEYYGRPFSITCLDNLVWSSPKDVC KRKSCKTPPDPVNGMVHVITDIQVGSRIQYSCTTGHRLIGHSSAECIL SGNAAHWSTKPPICQRIPCGLPPTIANGDFISTNRENFHYGSVVTYRC NPGSGGRKVFELVGEPSIYCTSNDDQVGIWSGPAPQCII |

| SEQ ID NO: | Description | Sequence |
|---|---|---|
| 43 | Human Complement Receptor 1 CCPs 15-17 protein coding sequence (underlined) Including leader sequence (doubled underlined); His tag (dotted line); TEV cleavage site (dashed line) Including HindIII restriction enzyme cleavage site (AAGCTT), Kozak consensus sequence (GCCACC), stop codon (TAA) and EcoRV restriction enzyme cleavage site (GATATC) | AAGCTTGCCACC<u>ATGAGACTGCTGGCCAAGATCATCTGCCTGATGCTG<br>TGGGCCATCTGCGTGGCC</u>CACCACCATCACCATCAC<u>GGCAGCAGC</u>GAG<br>AACCTGTACTTCCAAGGATCT<u>TCTGGCGGCCACTGTCAGGCCCCTGAT<br>CACTTCCTGTTCGCCAAGCTGAAAACCCAGACCAACGCCAGCGACTTC<br>CCTATCGGCACCAGCCTGAAGTACGAGTGCAGACCCGAGTACTACGGC<br>AGACCCTTCAGCATCACCTGTCTGGACAACCTCGTGTGGTCTAGCCCC<br>AAGGACGTGTGCAAGAGAAAGAGCTGCAAGACCCCTCCTGATCCTGTG<br>AACGGCATGGTGCACGTGATCACCGACATCCAAGTGGGCAGCAGAATC<br>AACTACAGCTGCACCACCGGCCACAGACTGATCGGACACTCTAGCGCC<br>GAGTGTATCCTGAGCGGCAATGCCGCACACTGGTCCACCAAGCCTCCA<br>ATCTGCCAGAGAATCCCTTGCGGCCTGCCTCCTACAATCGCCAACGGC<br>GATTTCATCAGCACCAACAGAGAGAACTTCCACTACGGCTCCGTGGTC<br>ACCTACAGATGCAATCCTGGCAGCGGCGGCAGAAAGGTGTTCGAACTT<br>GTGGGCGAGCCCAGCATCTACTGCACCAGCAACGATGACCAAGTCGGC<br>ATTTGGAGCGGCCCTGCTCCTCAGTGCATCATCCCTAAGATATC |
| 44 | Human Complement Receptor 1 CCPs 15-17 Including leader sequence (doubled underlined); His tag (dotted line); TEV cleavage site (dashed line) | <u>MRLLAKIICLMLWAICVA</u>HHHHHHGSS<u>ENLYFQGS</u>SGGHCQAPDHFLF<br>AKLKTQTNASDFPIGTSLKYECRPEYYGRPFSITCLDNLVWSSPKDVC<br>KRKSCKTPPDPVNGMVHVITDIQVGSRINYSCTTGHRLIGHSSAECIL<br>SGNTAHWSTKPPICQRIPCGLPPTIANGDFISTNRENFHYGSVVTYRC<br>NLGSRGRKVFELVGEPSIYCTSNDDQVGIWSGPAPQCII |
| 45 | Human Complement Receptor 1 CCPs 15-17 protein coding sequence (underlined) Non-glycosylated Including leader sequence (doubled underlined); His tag (dotted line); TEV cleavage site (dashed line) Including HindIII restriction enzyme cleavage site (AAGCTT), Kozak consensus sequence (GCCACC), stop codon (TAA) and EcoRV restriction enzyme cleavage site (GATATC) | AAGCTTGCCACC<u>ATGAGACTGCTGGCCAAGATCATCTGCCTGATGCTG<br>TGGGCCATCTGCGTGGCC</u>CACCACCATCACCATCAC<u>GGCAGCAGC</u>GAG<br>AACCTGTACTTCCAAGGATCT<u>TCTGGCGGCCACTGTCAGGCCCCTGAT<br>CACTTCCTGTTCGCCAAGCTGAAAACCCAGACACAGGCCAGCGACTTC<br>CCTATCGGCACCAGCCTGAAGTACGAGTGCAGACCCGAGTACTACGGC<br>AGACCCTTCAGCATCACCTGTCTGGACAACCTCGTGTGGTCTAGCCCC<br>AAGGACGTGTGCAAGAGAAAGAGCTGCAAGACCCCTCCTGATCCTGTG<br>AACGGCATGGTGCACGTGATCACCGACATCCAAGTGGGCAGCAGAATC<br>CAGTACAGCTGCACCACAGGCCACAGACTGATCGGCCACTCTAGCGCC<br>GAGTGTATCCTGAGCGGAAACACAGCCCACTGGTCCACCAAGCCTCCA<br>ATCTGCCAGAGAATCCCTTGCGGCCTGCCTCCTACAATCGCCAACGGC<br>GATTTCATCAGCACCAACAGAGAGAACTTCCACTACGGCTCCGTGGTC<br>ACCTACAGATGCAACCTGGGCTCCAGAGGCCGGAAGGTGTTCGAACTT<br>GTGGGCGAGCCTAGCATCTACTGCACCAGCAACGACGACCAAGTCGGC<br>ATTTGGAGCGGACCTGCTCCTCAGTGCATCATCCCTAAGATATC |
| 46 | Human Complement Receptor 1 CCPs 15-17 Non-glycosylated Including leader sequence (doubled underlined); His tag (dotted line); TEV cleavage site (dashed line) | <u>MRLLAKIICLMLWAICVA</u>HHHHHHGSS<u>ENLYFQGS</u>SGGHCQAPDHFLF<br>AKLKTQTQASDFPIGTSLKYECRPEYYGRPFSITCLDNLVWSSPKDVC<br>KRKSCKTPPDPVNGMVHVITDIQVGSRIQYSCTTGHRLIGHSSAECIL<br>SGNAAHWSTKPPICQRIPCGLPPTIANGDFISTNRENFHYGSVVTYRC<br>NPGSGGRKVFELVGEPSIYCTSNDDQVGIWSGPAPQCII |
| 47 | CR1a Including leader sequence (double underline); CCPs 8-10 | <u>MRLLAKIICLMLWAICVA</u>GHCQAPDHFLFAKLKTQTNASDFPIGTSLK<br>YECRPEYYGRPFSITCLDNLVWSSPKDVCKRKSCKTPPDPVNGMVHVI<br>TDIQVGSRINYSCTTGHRLIGHSSAECILSGNAAHWSTKPPICQRIPC<br>GLPPTIANGDFISTNRENFHYGSVVTYRCNPGSGGRKVFELVGEPSIY<br>CTSNDDQVGIWSGPAPQCII |
| 48 | nCR1a Including leader sequence (double underline); CCPs 8-10; N509Q and N578Q (numbered according to UniProt: P17927) | <u>MRLLAKIICLMLWAICVA</u>GHCQAPDHFLFAKLKTQTQASDFPIGTSLK<br>YECRPEYYGRPFSITCLDNLVWSSPKDVCKRKSCKTPPDPVNGMVHVI<br>TDIQVGSRIQYSCTTGHRLIGHSSAECILSGNAAHWSTKPPICQRIPC<br>GLPPTIANGDFISTNRENFHYGSVVTYRCNPGSGGRKVFELVGEPSIY<br>CTSNDDQVGIWSGPAPQCII |

Sequences

| SEQ ID NO: | Description | Sequence |
|---|---|---|
| 49 | CR1b Including leader sequence (double underline); CCPs 15-17 | MRLLAKIICLMLWAICVAGHCQAPDHFLFAKLKTQTNASDFPIGTSLK YECRPEYYGRPFSITCLDNLVWSSPKDVCKRKSCKTPPDPVNGMVHVI TDIQVGSRINYSCTTGHRLIGHSSAECILSGNTAHWSTKPPICQRIPC GLPPTIANGDFISTNRENFHYGSVVTYRCNLGSRGRKVFELVGEPSIY CTSNDDQVGIWSGPAPQCII |
| 50 | nCR1b Including leader sequence (double underline); CCPs 15-17; N959Q and N1028Q (numbered according to UniProt: P17927) | MRLLAKIICLMLWAICVAGHCQAPDHFLFAKLKTQTQASDFPIGTSLK YECRPEYYGRPFSITCLDNLVWSSPKDVCKRKSCKTPPDPVNGMVHVI TDIQVGSRIQYSCTTGHRLIGHSSAECILSGNTAHWSTKPPICQRIPC GLPPTIANGDFISTNRENFHYGSVVTYRCNLGSRGRKVFELVGEPSIY CTSNDDQVGIWSGPAPQCII |
| 51 | CR1a + CR1b Including leader sequence (double underline); CCPs 8-10 + 15-17 | MRLLAKIICLMLWAICVAGHCQAPDHFLFAKLKTQTNASDFPIGTSLK YECRPEYYGRPFSITCLDNLVWSSPKDVCKRKSCKTPPDPVNGMVHVI TDIQVGSRINYSCTTGHRLIGHSSAECILSGNAAHWSTKPPICQRIPC GLPPTIANGDFISTNRENFHYGSVVTYRCNPGSGGRKVFELVGEPSIY CTSNDDQVGIWSGPAPQCIIGHCQAPDHFLFAKLKTQTNASDFPIGTS LKYECRPEYYGRPFSITCLDNLVWSSPKDVCKRKSCKTPPDPVNGMVH VITDIQVGSRINYSCTIGHRLIGHSSAECILSGNTAHWSTKPPICQRI PCGLPPTIANGDFISTNRENFHYGSVVTYRCNLGSRGRKVFELVGEPS IYCTSNDDQVGIWSGPAPQCII |
| 52 | nCR1a + nCR1b Including leader sequence (double underline); CCPs 8-10 + 15-17; N509Q and N578Q, N959Q and N1028Q (numbered according to UniProt: P17927) | MRLLAKIICLMLWAICVAGHCQAPDHFLFAKLKTQTQASDFPIGTSLK YECRPEYYGRPFSITCLDNLVWSSPKDVCKRKSCKTPPDPVNGMVHVI TDIQVGSRIQYSCTIGHRLIGHSSAECILSGNAAHWSTKPPICQRIPC GLPPTIANGDFISTNRENFHYGSVVTYRCNPGSGGRKVFELVGEPSIY CTSNDDQVGIWSGPAPQCIIGHCQAPDHFLFAKLKTQTQASDFPIGTS LKYECRPEYYGRPFSITCLDNLVWSSPKDVCKRKSCKTPPDPVNGMVH VITDIQVGSRIQYSCTIGHRLIGHSSAECILSGNTAHWSTKPPICQRI PCGLPPTIANGDFISTNRENFHYGSVVTYRCNLGSRGRKVFELVGEPS IYCTSNDDQVGIWSGPAPQCII |
| 53 | CR1a + nCR1b Including leader sequence (double underline); CCPs 8-10 + 15-17; N959Q and N1028Q (numbered according to UniProt: P17927) | MRLLAKIICLMLWAICVAGHCQAPDHFLFAKLKTQTNASDFPIGTSLK YECRPEYYGRPFSITCLDNLVWSSPKDVCKRKSCKTPPDPVNGMVHVI TDIQVGSRINYSCTIGHRLIGHSSAECILSGNAAHWSTKPPICQRIPC GLPPTIANGDFISTNRENFHYGSVVTYRCNPGSGGRKVFELVGEPSIY CTSNDDQVGIWSGPAPQCIIGHCQAPDHFLFAKLKTQTQASDFPIGTS LKYECRPEYYGRPFSITCLDNLVWSSPKDVCKRKSCKTPPDPVNGMVH VITDIQVGSRIQYSCTIGHRLIGHSSAECILSGNTAHWSTKPPICQRI PCGLPPTIANGDFISTNRENFHYGSVVTYRCNLGSRGRKVFELVGEPS IYCTSNDDQVGIWSGPAPQCII |
| 54 | nCR1a + CR1b Including leader sequence (double underline); CCPs 8-10 + 15-17; N509Q and N578Q (numbered according to UniProt: P17927) | MRLLAKIICLMLWAICVAGHCQAPDHFLFAKLKTQTQASDFPIGTSLK YECRPEYYGRPFSITCLDNLVWSSPKDVCKRKSCKTPPDPVNGMVHVI TDIQVGSRIQYSCTIGHRLIGHSSAECILSGNAAHWSTKPPICQRIPC GLPPTIANGDFISTNRENFHYGSVVTYRCNPGSGGRKVFELVGEPSIY CTSNDDQVGIWSGPAPQCIIGHCQAPDHFLFAKLKTQTNASDFPIGTS LKYECRPEYYGRPFSITCLDNLVWSSPKDVCKRKSCKTPPDPVNGMVH VITDIQVGSRINYSCTIGHRLIGHSSAECILSGNTAHWSTKPPICQRI PCGLPPTIANGDFISTNRENFHYGSVVTYRCNLGSRGRKVFELVGEPS IYCTSNDDQVGIWSGPAPQCII |

Functional Properties of the Polypeptide

The polypeptide according to the present invention may be characterised by reference to one or more functional properties.

In particular, a polypeptide according to the present invention may possess one or more of the following properties (as determined by analysis in an appropriate assay for said property):

Binds to C3b;
Binds to C3b with an affinity of binding which is similar to the affinity of binding to C3b displayed by a co-factor for Complement Factor I (or a fragment thereof;
Binds to C3b with an affinity of binding which is higher than the affinity of binding to C3b displayed by a co-factor for Complement Factor I (or a fragment thereof;
Binds to C3b with an affinity of binding which is similar to the affinity of binding to C3b displayed by Complement Receptor 1 (or a fragment thereof;
Binds to C3b in the region of C3b bound by a co-factor for Complement Factor I (or a fragment thereof);
Binds to C3b in the region of C3b bound by Complement Receptor 1 (or a fragment thereof);
Binds to C3b in the region of C3b bound by Complement Receptor 1 CCP domains 8-10 and/or 15-17 (or a fragment thereof);
Acts as a co-factor to enable Complement Factor I-mediated inactivation of C3b;
Acts as a co-factor to enable Complement Factor I-mediated reduction/prevention of the formation of a functional C3bBb-type C3 convertase;

Acts as a co-factor to enable Complement Factor I-mediated reduction/prevention of the formation of a functional C3bBb3b-type C5 convertase;

Acts as a co-factor to enable Complement Factor I-mediated reduction/prevention of the formation of a functional C4b2a3b-type C5 convertase;

Acts as a co-factor to enable Complement Factor I-mediated reduction of C3bBb-type C3 convertase activity;

Acts as a co-factor to enable Complement Factor I-mediated reduction of C3bBb3b-type C5 convertase activity;

Acts as a co-factor to enable Complement Factor I-mediated reduction of C4b2a3b-type C5 convertase activity;

Acts as a co-factor to enable Complement Factor I-mediated reduction of the amount of C3bBb-type C3 convertase;

Acts as a co-factor to enable Complement Factor I-mediated reduction of the amount of C3bBb3b-type C5 convertase;

Acts as a co-factor to enable Complement Factor I-mediated reduction of the amount of C4b2a3b-type C5 convertase;

Reduces the amount of C3b via Complement Factor I;
Increases the amount of iC3b via Complement Factor I;
Increases the amount of C3dg via Complement Factor I;
Increases the amount of C3d via Complement Factor I;
Increases the amount of C3f via Complement Factor I;
Reduces the amount of C5b via Complement Factor I;
Reduces the amount of C5a via Complement Factor I;
Decreases the amount of iC3b via Complement Factor I compared to the amount of iC3b produced by FH and/or FHL-1 via Complement Factor I;

Increases the ratio of C3dg to iC3b via Complement Factor I;

Is capable of inhibiting complement activation;
Diffuses through Bruch's membrane (BrM);
Displays superior ability to diffuse through BrM compared to Complement Factor I;
Displays superior ability to diffuse through BrM compared to a co-factor for Complement Factor I (or a fragment thereof);
Displays similar ability to diffuse through BrM compared to a co-factor for Complement Factor I (or a fragment thereof);
Displays superior ability to diffuse through BrM compared to Complement Factor H;
Displays similar ability to diffuse through BrM compared to Complement Factor H isoform FHL-1;
Displays superior ability to diffuse through BrM compared to Complement Factor H isoform FHL-1;
Displays similar ability to diffuse through BrM compared to soluble Complement Receptor 1;
Displays superior ability to diffuse through BrM compared to soluble Complement Receptor 1.

Whether a given polypeptide possesses the functional properties referred to in the previous paragraph can be analysed, for example, as described herein.

A polypeptide according to the present invention may be capable of binding to C3b. In some embodiments, a polypeptide according to the present invention may comprise or consist of a C3b binding region. In some embodiments, the C3b binding region of the polypeptide according to the present invention comprises or consists of a C3b binding region of CR1, e.g. CCP domains 8-10 and/or 15-17.

As used herein, a "C3b binding region" refers to a region capable of binding to C3b. In some embodiments, the C3b binding region is capable of specific binding to C3b. Binding to C3b may be mediated by non-covalent interactions such as Van der Waals forces, electrostatic interactions, hydrogen bonding, and hydrophobic interactions formed between the C3b binding region and C3b. In some embodiments, the C3b binding region binds to C3b with greater affinity, and/or with greater duration than it binds to molecules other than C3b.

The ability of a polypeptide according to the present invention or a putative C3b binding region to bind to C3b can be analysed using techniques well known to the person skilled in the art, including ELISA, Surface Plasmon Resonance (SPR; see e.g. Hearty et al., Methods Mol Biol (2012) 907:411-442; or Rich et al., Anal Biochem. 2008 Feb. 1; 373(1):112-20), Bio-Layer Interferometry (see e.g. Lad et al., (2015) J Biomol Screen 20(4): 498-507; or Concepcion et al., Comb Chem High Throughput Screen. 2009 September; 12(8):791-800), MicroScale Thermophoresis (MST) analysis (see e.g. Jerabek-Willemsen et al., Assay Drug Dev Technol. 2011 August; 9(4): 342-353), or by a radiolabelled antigen binding assay (RIA). Through such analysis binding to a given target can be determined and quantified. In some embodiments, the binding may be the response detected in a given assay.

In some embodiments, a polypeptide according to the present invention displays binding to C3b in such an assay which is greater than 1 times, e.g. one of >1.01, >1.02, >1.03, >1.04, >1.05, >1.06, >1.07, >1.08, >1.09, >1.1, >1.2, >1.3, >1.4, >1.5, >1.6, >1.7, >1.8, >1.9, >2, >3, >4, >5, >6, >7, >8, >9, >10, >15, >20, >25, >30, >35, >40, >45, >50, >60, >70, >80, >90, or >100 times the level of binding signal detected in such an assay to a negative control molecule to which the C3b binding region does not bind.

In some embodiments, a polypeptide according to the present invention is capable of binding to C3b with an affinity of binding which is similar to the affinity of binding to C3b displayed by CR1 or another co-factor for Complement Factor I (or a fragment thereof) in a given assay. An affinity of binding which is similar to a reference affinity of binding can be e.g. ±40% of the level of binding, e.g. one of ±35%, ±30%, ±25%, ±20%, ±15%, ±10% or ±5% of the level of binding to C3b displayed by reference CR1 or the reference co-factor for Complement Factor I in a comparable assay.

In some embodiments a polypeptide according to the present invention is capable of binding to C3b with an affinity of binding which is higher than the affinity of binding to C3b displayed by a co-factor for Complement Factor I (or a fragment thereof) in a given assay. In some embodiments a polypeptide according to the present invention is capable of binding to C3b with an affinity of binding which is 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 35 times, 40 times, 45 times, 50 times, 75 times, 100 times, 150 times, 200 times, 250 times, 300 times, 350 times, 400 times, 450 times, 500 times, 550 times, 600 times, 650 times, 700 times, 750 times, 800 times, 850 times, 900 times, 950 times, or 1000 times the affinity of binding to C3b displayed by a co-factor for Complement Factor I (or a fragment thereof) in a given assay. In some embodiments a polypeptide according to the present invention is capable of binding to C3b with an affinity of binding which is 10000 times, 100000 times, or 1000000 times the affinity of binding to C3b displayed by a co-factor for Complement Factor I (or a fragment thereof) in a given assay. In some embodiments a polypeptide according to the present invention is capable of binding to C3b with an affinity of binding which is 2, 3, 4, 5, 6, 7, 8, 9 or 10 order(s) of magnitude greater than the affinity of binding to C3b displayed by a co-factor for Complement Factor I (or a fragment thereof) in a given assay. In some embodiments the co-factor for Complement Factor I is Complement Factor H or truncated FH isoform FHL-1. The co-factor for Complement Factor I may be CR1.

In some embodiments, a polypeptide according to the present invention is capable of binding to C3b in the region of C3b that is bound by a co-factor for Complement Factor I (i.e. binds to the same region or an overlapping region). In some embodiments, the polypeptide is capable of binding to C3b in the region bound by CR1 (or a fragment thereof). In some embodiments, the polypeptide is capable of binding to C3b in the region bound by CR1 CCP domains 8-10 and/or 15-17. In some embodiments, the polypeptide is capable of binding to C3b in the region bound by one or more of Complement Factor I co-factors Complement Factor H, CD46, CD55, C4BP, SPICE, VCP, or MOPICE (or fragments thereof).

Whether a polypeptide according to the present invention binds to C3b in the region of C3b bound by a given co-factor for Complement Factor I (or a fragment thereof) can be determined by various methods known to the skilled person, including ELISA, and surface plasmon resonance (SPR) analysis. An example of a suitable assay to determine whether a C3b binding region binds to C3b in the region bound by a given co-factor for Complement Factor I (or a fragment thereof is a competition ELISA assay.

For example, whether a polypeptide according to the present invention binds to C3b in the region of C3b bound by a given co-factor for Complement Factor I (or a fragment thereof can be determined by analysis of interaction of the co-factor/fragment with C3b in the presence of, or following incubation of one or both of the co-factor/fragment and C3b with the polypeptide according to the present invention. A C3b binding region which binds to C3b in the region of C3b bound by a given co-factor/fragment is identified by the observation of a reduction/decrease in the level of interaction between the co-factor/fragment and C3b in the presence of—or following incubation of one or both of the interaction partners with—the polypeptide according to the present invention, as compared to the level of interaction in the absence of the polypeptide according to the present invention (or in the presence of an appropriate control peptide/polypeptide). Suitable analysis can be performed in vitro, e.g. using recombinant interaction partners. For the purposes of such assays, one or both of the interaction partners and/or the polypeptide according to the present invention may be labelled, or used in conjunction with a detectable entity for the purposes of detecting and/or measuring the level of interaction.

In some embodiments, the polypeptide according to the present invention acts as a co-factor for Complement Factor I. For example, the polypeptide may potentiate cleavage of C3b by Complement Factor I, and/or present C3b in a favourable orientation for proteolytic cleavage by Complement Factor I. The polypeptide preferably does not inhibit proteolytic cleavage of C3b by Complement Factor I. In some embodiments, the Complement Factor I is endogenous. In some embodiments, the Complement Factor I is exogenous.

As used herein, an 'endogenous' protein/peptide refers to a protein/peptide which is encoded/expressed by the relevant cell type, tissue, or subject (prior to treatment with a polypeptide, nucleic acid, vector, cell or pharmaceutical composition according to the present invention). A 'non-endogenous' or 'exogenous' protein/peptide refers to a protein/peptide which is not encoded/expressed by, the relevant cell type, tissue, or subject (prior to treatment with a polypeptide, nucleic acid, vector, cell or pharmaceutical composition according to the present invention).

A polypeptide according to the present invention that acts as a co-factor for Complement Factor I can be determined by e.g. by analysis of the level or rate of proteolytic cleavage of C3b by Complement Factor I in a suitable assay in the presence of (or after incubation with) a polypeptide according to the present invention as compared to the level or rate of proteolytic cleavage of C3b by Complement Factor I in the absence of the polypeptide according to the present invention (or in the presence of an appropriate control peptide/polypeptide). A C3b binding region which acts as a co-factor for Complement Factor I is identified by the detection of an increased level or rate of proteolytic cleavage of C3b by Complement Factor I in the presence of (or after incubation with) a polypeptide according to the present invention as compared to the level or rate of proteolytic cleavage of C3b by Complement Factor I in the absence of the polypeptide according to the present invention (or in the presence of an appropriate control peptide/polypeptide). The level or rate of proteolytic cleavage of C3b by Complement Factor I can be determined e.g. by detection of one or more products of cleavage of C3b by Complement Factor I, e.g. iC3b, C3dg, C3d or C3f. The level or rate of proteolytic cleavage of C3b by Complement Factor I can be determined e.g. by detection of a reduction in the presence of C3b. In some embodiments a polypeptide according to the present invention that acts as a co-factor for Complement Factor I produces a smaller amount of iC3b overall compared to an amount of iC3b produced by FH/FHL-1 via Complement Factor I. In some embodiments a polypeptide according to the present invention that acts as a co-factor for Complement Factor I increases the ratio of C3dg to iC3b via Complement Factor I compared to the ratio of C3dg to iC3b produced by FH/FHL-1 via Complement Factor I. For example, the polypeptide may not increase the overall amount of iC3b, but may instead increase the amount of C3dg, C3f and/or C3d via Complement Factor I.

In some embodiments a polypeptide according to the present invention is capable of inhibiting or reducing complement activation. A polypeptide may inhibit or reduce complement over-activation. The level of complement activation/over-activation may be determined by the assays described herein, e.g. abnormal levels of complement components, or by tests/assays that are known by one skilled in the art, e.g. as described in Shih and Murali Am. J. Hematol. 2015, 90: 1180-1186; Kirschfink and Mollnes, Clin Diagn Lab Immunol. 2003, 10(6): 982-989; Nilsson and Ekdahl, Clinical and Developmental Immunology, 2012, Article ID 962702; which are hereby incorporated by reference in their entirety.

In some embodiments, the polypeptide according to the present invention possesses the ability to diffuse through, i.e. pass through, Bruch's Membrane (BrM), as determined by analysis in an appropriate assay for said property.

The ability of a given polypeptide to diffuse through BrM can be analysed e.g. in vitro, e.g. as described in Clark et al J. Immunol (2014) 193, 4962-4970. Briefly, BrM can be isolated from donor eyes as described in McHarg et al., J Vis Exp (2015) 1-7, and the macular area can be mounted in an Ussing chamber. Once mounted, the 5 mm diameter macular area is the only barrier between two identical compartments. Both sides of BrM can be washed with PBS, and human serum can be diluted 1:1 with PBS and added to the Ussing compartment on one side of the BrM (the sample chamber). The polypeptide to be analysed can be added to the sample chamber in PBS, and PBS alone can be added to the compartment on the other side of the BrM (the diffusate chamber), and the Ussing chamber can be incubated at room temperature for 24 hours with gentle stirring in both the sample and diffusate chambers. Samples from each chamber can subsequently be analysed for the presence of the polypeptide, e.g. using antibody based detection methods such as ELISA analysis or western blot. Detection of the polypeptide in the diffusate chamber indicates that the polypeptide is capable of diffusing through BrM. Suitable positive and negative control proteins known to be able to/not to be able to diffuse through BrM can be included in such experiments.

In some embodiments, a polypeptide according to the present invention displays superior ability to diffuse through BrM than Complement Factor I. In some embodiments, a polypeptide according to the present invention displays superior ability to diffuse through BrM than Complement Factor H. FH, consisting of 20 CCP domains, is a large molecule and does not pass through BrM. In some embodiments, a polypeptide according to the present invention displays similar ability to diffuse through BrM as compared to the truncated Complement Factor H isoform FHL-1 (UniProt: P08603-2; SEQ ID NO:28). In some embodiments, a polypeptide according to the present invention displays superior ability to diffuse through BrM as compared to Complement Factor H isoform FHL-1. In some embodiments, a polypeptide according to the present invention displays similar ability to diffuse through BrM as compared to full length soluble CR1 (30 CCP domains; SEQ ID NO:1 lacking SEQ ID NO:32 and 33). In some embodiments, a polypeptide according to the present invention displays superior ability to diffuse through BrM as compared to full length soluble CR1. A polypeptide according to the present invention that is able to diffuse though BrM preferably remains functionally active, i.e. acts as a cofactor for Complement Factor I, after diffusing though BrM.

A polypeptide of the present invention displaying superior ability to diffuse through BrM as compared to a given reference polypeptide can be identified by analysing diffusion through BrM as described above. The diffusion through BrM may be detected by measuring the rate of diffusion through to the diffusate chamber and/or detecting the proportion of polypeptide present in the diffusate chamber at the end of the experiment. A polypeptide of the present invention displaying similar ability to diffuse through BrM as compared to a given reference polypeptide can be identified by analysing diffusion through BrM as described above. A similar ability to diffuse through BrM may be indicated by detecting a rate of diffusion through to the diffusate chamber which is within 30%, e.g. within one of 25%, 20%, 15%, or 10% of the rate of diffusion for a reference polypeptide, and/or by detecting a proportion of the polypeptide of the present invention present in the diffusate chamber at the end of the experiment that is within 30%, e.g. within one of 25%, 20%, 15%, or 10% of the proportion of a reference polypeptide present in the diffusate chamber.

As a result of the ability of the polypeptides to diffuse through the BrM, the polypeptides of the present invention are also able to diffuse away from the site of C3b inactivation if/once they have performed their cofactor role with FI. In other words, the polypeptides of the present invention may be capable of being present transiently at areas of complement activation. This is advantageous because accumulation of complement-related debris is undesirable, particularly in the context of macular degeneration where cellular debris accumulation can lead to the formation of drusen.

A polypeptide of the present invention may be capable of being expressed in a cell, e.g. a cell as described herein. A polypeptide of the present invention may be capable of being secreted by a cell, e.g. a cell as described herein. In some embodiments the cell is an ocular cell, e.g. an RPE cell, as described herein.

Nucleic Acids, Cells, Compositions and Kits

The present invention provides a nucleic acid encoding a polypeptide according to the present invention. In some embodiments, the nucleic acid is purified or isolated, e.g. from other nucleic acid, or naturally-occurring biological material. In some embodiments the nucleic acid(s) comprise or consist of DNA and/or RNA.

Provided herein are nucleic acid sequences that encode a polypeptide comprising or consisting of SEQ ID NO:2, 3, 5, 6, 13, 14, 15, 30, 31, 40, 42, 44, 46, 47, 48, 49, 50, 51, 52, 53 or 54. The encoded polypeptide may be produced with or without a leader sequence e.g. a secretory pathway sequence. The encoded polypeptide may be produced together with a leader sequence which is then subsequently removed from said polypeptide.

In some embodiments, a nucleic acid according to the present invention comprises, or consists of, one or more of SEQ ID NO:35, 36, 37, 38, 39, 41, 43, and/or 45, or equivalent nucleic acid sequences thereof which would be translated into the same respective polypeptides due to codon degeneracy.

The present invention also provides a vector comprising nucleic acid encoding a polypeptide according to the present invention.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. A vector may include regulatory elements, such as a polyadenylation site. Any suitable vectors, promoters, enhancers and termination codons known in the art may be used to express a peptide or polypeptide from a vector according to the invention. Nucleic acid sequences described herein may be codon optimised for optimised expression in a desired cell or organism.

The term "operably linked" may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

The nucleic acid and/or vector according to the present invention is preferably provided for introduction into a cell, e.g. a human cell. Suitable vectors include plasmids, binary vectors, DNA vectors, mRNA vectors, viral vectors (e.g. gammaretroviral vectors (e.g. murine Leukemia virus (MLV)-derived vectors), lentiviral vectors, retroviral vectors, adenovirus vectors, adeno-associated virus (AAV) vectors, vaccinia virus vectors and herpesvirus vectors, e.g.

Herpes Simplex Virus vectors), transposon-based vectors, and artificial chromosomes (e.g. yeast artificial chromosomes), e.g. as described in Maus et al., Annu Rev Immunol (2014) 32:189-225 or Morgan and Boyerinas, Biomedicines 2016 4, 9, which are both hereby incorporated by reference in its entirety. In some embodiments, the lentiviral vector may be pELNS, or may be derived from pELNS. In some embodiments, the vector may be a vector encoding CRISPR/Cas9. In some embodiments, the adeno-associated virus (AAV) vector is selected from AAV serotype 1, 2, 3, 4, 5, 6, 7, 8, 9, 10 or 11, or hybrids and/or mutants thereof. In some embodiments, the AAV vector is an AAV serotype 2 (AAV-2) vector, or a hybrid and/or mutant thereof. Viral and non-viral delivery systems for introducing genetic material into cells are reviewed, for example, in Nayerossadat et al., Adv Biomed Res. 2012; 1: 27; MacLaren et al. Ophthalmology. 2016, 123(10 Suppl): S98-S106; Petit and Punzo, Discov Med. 2016, 22(121): 221-229; Aguirre, Invest Ophthalmol Vis Sci. 2017, 58(12): 5399-5411; Lundstrom, Diseases. 2018, 6(2): 42; which are hereby incorporated by reference in their entirety. Any suitable nucleotide or vector delivery method can be used in the context of the present invention.

In some embodiments the expression of a nucleic acid or a nucleic acid contained in a vector, according to the present invention, is driven by a promoter that drives expression in a specific retinal cell type, e.g. rods, cones, RPE, or ganglion cells, as described for example in Beltran W A, et al. Gene Ther. 2010; 17:1162-74 and Boye S E, et al. Hum Gene Ther. 2012; 23:1101-15, which are hereby incorporated by reference in their entirety.

In some embodiments, the expression of a nucleic acid or a nucleic acid contained in a vector, according to the present invention, is driven by a promoter that drives expression of that nucleic acid in retinal pigment epithelial (RPE) cells. In some embodiments, the promoter is an RPE65 or VMD2 promoter, or modified version thereof. In some embodiments the promoter is a chicken β actin promoter.

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

In some embodiments the vector comprises an inducible promoter, i.e. gene expression is activated by the promoter only in the presence or absence of a particular molecule. Suitable inducible promoters will be known to the skilled person. Examples of inducible promoters are described in e.g. Le at al. Invest Ophthalmol Vis Sci. 2008, 49(3): 1248-1253 and McGee Sanftner et al. Mol Ther. 2001. 3(5): 688-696; which are hereby incorporated by reference in their entirety.

In some embodiments, the nucleic acid comprises, or consists of, a nucleic acid sequence encoding a polypeptide having an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:2, 3, 4, 5, 6, 8, 9, 10, 11, 12, 13, 14, 15, 16, 17, 30, 31, 40, 42, 44, 46, 47, 48, 49, 50, 51, 52, 53, or 54, or any combination of sequences A, B, and/or C as described hereinabove.

The present invention also provides a cell comprising or expressing a polypeptide according to the present invention. Also provided is a cell comprising or expressing a nucleic acid or vector according to the invention. The cell comprising or expressing polypeptide, nucleic acid or vector according to the present invention may secrete a polypeptide according to the present invention. That is, expression of the polypeptide, nucleic acid or vector by the cell may result in the soluble production of a polypeptide according of the present invention from the cell.

The cell may be a eukaryotic cell, e.g. a mammalian cell. The mammal may be a human, or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate). In some embodiments, the cell may be from, or may have been obtained from, a human subject.

In some embodiments, the cell is a cell of the eye. In some embodiments, the cell is a cell of the neurosensory retina, retinal pigment epithelium (RPE), choroid or macula. In some embodiments, the cell is a retinal cell. In some embodiments, the cell is a retinal pigment epithelial cell. In some embodiments, the cell is a human retinal pigment epithelial cell (RPE). In some embodiments the cell is a photoreceptor cell.

The present invention also provides a method for producing a cell comprising a nucleic acid or vector according to the present invention, comprising introducing a nucleic acid or vector according to the present invention into a cell. In some embodiments, introducing an isolated nucleic acid(s) or vector(s) according to the invention into a cell comprises transformation, transfection, electroporation or transduction (e.g. retroviral transduction). Methods for producing a cell according to the present invention may be performed according to methods known to the skilled person for the production of cells comprising nucleic acid/vectors.

The present invention also provides a method for producing a cell comprising or expressing a polypeptide according to the present invention, comprising introducing a nucleic acid or vector according to the present invention into a cell. In some embodiments, the methods additionally comprise culturing the cell under conditions suitable for expression of the nucleic acid or vector by the cell. In some embodiments, the methods are performed in vitro or ex vivo. In some embodiments, the methods are performed in vivo.

The present invention also provides cells obtained or obtainable by the methods according to the present invention.

The present invention also provides compositions comprising a polypeptide, nucleic acid, vector, or cell according to the present invention.

Polypeptides, nucleic acids, vectors and cells according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating a polypeptide, cell, nucleic acid or vector as described herein; and/or mixing a polypeptide, cell, nucleic acid or vector as described herein with a pharmaceutically acceptable carrier, adjuvant, excipient or diluent.

A kit of parts is also provided. In some embodiments the kit may have at least one container having a predetermined quantity of a polypeptide, nucleic acid, vector, cell, and/or composition according to the present invention.

The kit may provide the polypeptide, nucleic acid, vector, cell or composition together with instructions for administration to a subject in order to treat a specified disease/ condition. The polypeptide, nucleic acid, vector, cell or composition may be formulated so as to be suitable for injection or infusion. In some embodiments, the polypeptide, nucleic acid, vector, cell or composition may be formulated so as to be suitable for intravenous, intraocular, sub-retinal, suprachoroidal or intraconjunctival injection, administration as an eye drop (i.e. ophthalmic administration), or oral administration.

In some embodiments the kit may comprise materials for producing a cell according to the present invention. For example, the kit may comprise materials for modifying a cell to express or comprise a polypeptide, nucleic acid or vector according to the present invention, or materials for introducing into a cell the nucleic acid or vector according to the present invention.

In some embodiments the kit may further comprise at least one container having a predetermined quantity of another therapeutic agent (e.g. a therapeutic agent for the treatment of AMD). In such embodiments, the kit may also comprise a second medicament or pharmaceutical composition such that the two medicaments or pharmaceutical compositions may be administered simultaneously or separately such that they provide a combined treatment for the specific disease or condition. In some embodiments, the second medicament or pharmaceutical composition comprises Complement Factor I.

Producing Polypeptides

The present invention also provides a method for producing a polypeptide according to the present invention, the method comprising introducing into a cell a nucleic acid or vector according to the present invention, and culturing the cell under conditions suitable for expression of the polypeptide. The polypeptide may be a fusion protein. The polypeptide may be subsequently isolated and/or substantially purified.

Polypeptides according to the present invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according to using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonication, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. The polypeptide may also be affinity-purified using an appropriate binding partner for a molecular tag on the polypeptide (e.g. a His, FLAG, Myc, GST, MBP, HA, E, or Biotin tag). These may be used as an alternative to precipitation, or may be performed subsequently to precipitation.

In some cases it may further be desired to process the polypeptide, e.g. to remove a sequence of amino acids, molecular tag, moiety, etc.

In some embodiments, treatment is with an appropriate endopeptidase for the cleavage and removal of an amino acid sequence.

In some embodiments, treatment is with an enzyme to remove the moiety of interest. In some embodiments, the polypeptide is treated to remove glycans (i.e. the polypeptide is degylcosylated), e.g. by treatment with a glycosidase such as with a Peptide:N-glycosidase (PNGase).

Once the polypeptide(s) of interest have been isolated from culture it may be desired or necessary to concentrate the polypeptide(s). A number of methods for concentrating proteins are known in the art, such as ultrafiltration or lyophilisation.

In some embodiments, the production of the polypeptide occurs in vivo, e.g. after introduction to the host of a cell comprising a nucleic acid or vector encoding a polypeptide of the present invention, or following introduction into a cell of the host of a nucleic acid or vector encoding a polypeptide of the present invention. In such embodiments, the polypeptide is transcribed, translated and post-translationally processed to the mature polypeptide. In some embodiments, the polypeptide is produced in situ at the desired location in the host. In some embodiments, the desired location is the eye, e.g. in a cell of the retina, choroid, retinal pigment epithelium (RPE) or macula. In some embodiments, the desired location is at or in a retinal cell. In some embodiments, the desired location is at or in a RPE cell.

Therapeutic Applications

Any of the polypeptides, nucleic acids, vectors, cells and pharmaceutical compositions according to the present invention find use in therapeutic and prophylactic methods.

The present invention provides a polypeptide, nucleic acid, vector, cell, or pharmaceutical composition according to the present invention, for use in a method of medical treatment or prophylaxis. The present invention also provides the use of a polypeptide, nucleic acid, vector, cell or pharmaceutical composition according to the present invention in the manufacture of a medicament for treating or preventing a disease or condition. The present invention also provides a method of treating or preventing a disease or condition, comprising administering to a subject a therapeutically or prophylactically effective amount of a polypeptide, nucleic acid, vector, cell or pharmaceutical composition according to the present invention.

In particular, the polypeptides, nucleic acids, vectors, cells and pharmaceutical compositions according to the present invention find use to treat or prevent diseases/conditions associated with complement dysregulation, in particular overactive complement response. In some embodiments, the overactive complement response is linked to the presence of C3b. In some embodiments the disease/condition to be treated or prevented is a complement-related disease. In some embodiments the disease/condition to be treated or prevented is pathologically associated with complement activation. In some embodiments the disease/condition to be treated or prevented is pathologically associated with complement over-activation. In some embodiments the disease/condition to be treated or prevented is driven by complement activation or over-activation. In some embodiments the disease/condition is complement activation or over-activation.

The polypeptides, nucleic acids, vectors, cells and pharmaceutical compositions find use to treat or prevent diseases/conditions which would benefit from one or more of: a reduction in the level or activity of C3bBb-type C3 convertase, C3bBb3b-type C5 convertase or C4b2a3b-type C5 convertase; a reduction in the level of C3b, C5b or C5a; an increase in the level of iC3b, C3f, C3dg or C3d; or a reduction in the level or activity of iC3b and an increase in the level of C3f, C3dg or C3d.

'Treatment' may, for example, be reduction in the development or progression of a disease/condition, alleviation of the symptoms of a disease/condition or reduction in the pathology of a disease/condition. Treatment or alleviation of a disease/condition may be effective to prevent progression of the disease/condition, e.g. to prevent worsening of the condition or to slow the rate of development. In some embodiments treatment or alleviation may lead to an improvement in the disease/condition, e.g. a reduction in the symptoms of the disease/condition or reduction in some other correlate of the severity/activity of the disease/condition. Prevention/prophylaxis of a disease/condition may refer to prevention of a worsening of the condition or prevention of the development of the disease/condition, e.g. preventing an early stage disease/condition developing to a later, chronic, stage.

In some embodiments, the disease or condition to be treated or prevented may be a disease/condition associated with C3b or a C3b-containing complex, an activity/response associated with C3b or a C3b-containing complex, or a product of an activity/response associated with C3b or a C3b-containing complex. That is, in some embodiments, the disease or condition to be treated or prevented is a disease/condition in which C3b, a C3b-containing complex, an activity/response associated with C3b or a C3b-containing complex, or the product of said activity/response is pathologically implicated. In some embodiments, the disease/condition may be associated with an increased level of C3b or a C3b-containing complex, an increased level of an activity/response associated with C3b or a C3b-containing complex, or increased level of a product of an activity/response associated with C3b or a C3b-containing complex as compared to the control state.

The treatment may be aimed at reducing the level of C3b or a C3b-containing complex, an activity/response associated with C3b or a C3b-containing complex, or a product of an activity/response associated with C3b or a C3b-containing complex. In some embodiments, the treatment is aimed at: reducing the level or activity of C3bBb-type C3 convertase, C3bBb3b-type C5 convertase or C4b2a3b-type C5 convertase; reducing the level of C3b, C5b or C5a; increasing the level of iC3b, C3f, C3dg or C3d, or reducing the level of iC3b and increasing the level of C3f, C3dg or C3d.

Administration of the polypeptides, nucleic acids, vectors, cells and compositions of the present invention may cause a reduction in the level of C3b or a C3b-containing complex, an activity/response associated with C3b or a C3b-containing complex, or a product of an activity/response associated with C3b or a C3b-containing complex through cleavage of C3b.

In some embodiments, the treatment may be aimed at reducing the level of C3b or a C3b-containing complex, an activity/response associated with C3b or a C3b-containing complex, or a product of an activity/response associated with C3b or a C3b-containing complex in a subject, e.g. at a particular location, in a particular organ, tissue, structure or cell type. In some embodiments, the treatment may be aimed at reducing the level of C3b or a C3b-containing complex, an activity/response associated with C3b or a C3b-containing complex, or a product of an activity/response associated with C3b or a C3b-containing complex in the eye, e.g. in the retina, choroid, RPE, macula and/or at the BrM/RPE interface.

In some embodiments, the treatment may comprise modifying a cell or population of cells to comprise/express a polypeptide, nucleic acid or vector of the present invention. In some embodiments, the treatment may comprise modification of the cell/population in vivo, for in situ production of the polypeptide of the invention. In some embodiments the cell/population of cells is/are an ocular cell/cells. In some embodiments, the cell/population of cells is a RPE cell and/or population of RPE cells. In some embodiments the cell/population of cells is a photoreceptor cell and/or population of photoreceptor cells.

In some embodiments, the present invention provides a nucleic acid or vector of the present invention for use in gene therapy. In some embodiments, the treatment comprises administering the nucleic acid and/or vector to a subject. In some embodiments, the treatment comprises introducing the nucleic acid and/or vector into a cell of a subject, using techniques described herein or well known in the art, see e.g. MacLaren et al. Ophthalmology. 2016, 123(10 Suppl): S98-S106; Aguirre, Invest Ophthalmol Vis Sci. 2017, 58(12): 5399-5411; Lundstrom, Diseases. 2018, 6(2): 42; which are hereby incorporated by reference in their entirety. In some embodiments the cell is an ocular cell or cells. In some embodiments, the cell is an RPE cell or cells. In some embodiments the cell is a photoreceptor cell or cells.

In some embodiments, the treatment may comprise administering to a subject a cell or population of cells modified to comprise/express a polypeptide, nucleic acid or vector of the present invention. In some embodiments, the treatment may comprise modification of the cell/population ex vivo or in vitro.

In some embodiments, the treatment is aimed at providing the subject with a cell or population of cells which produce and/or will produce the polypeptide of the invention, e.g. by administering a cell according to the present invention, or by generating a cell according to the present invention.

In some embodiments, the cell referred to herein is a cell of the eye i.e. an ocular cell. In some embodiments, the cell is a cell of the retina, choroid, retinal pigment epithelium (RPE) or macula. In some embodiments, the cell is a retinal cell. In some embodiments, the cell is an RPE cell. In some embodiments the cell is a photoreceptor cell.

The present invention provides a method of treating or preventing a disease or condition in a subject, the method comprising modifying at least one cell to express or comprise a polypeptide, nucleic acid or vector according to the present invention. In some embodiments the at least one cell is an ocular cell. In some embodiments, the at least one cell is an RPE cell.

The at least one cell modified according to the present invention can be modified according to methods well known to the skilled person. The modification may comprise nucleic acid transfer for permanent or transient expression of the transferred nucleic acid. Any suitable genetic engineering platform may be used to modify a cell according to the present invention. Suitable methods for modifying a cell include the use of genetic engineering platforms such as gammaretroviral vectors, lentiviral vectors, adenovirus vectors, adeno-associated virus (AAV) vectors, DNA transfection, transposon-based gene delivery and RNA transfection, for example as described in Maus et al., Annu Rev Immunol (2014) 32:189-225, incorporated by reference hereinabove.

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

The subject to be treated may display an elevated level of C3b or a C3b-containing complex, an activity/response associated with C3b or a C3b-containing complex, or a product of an activity/response associated with C3b or a C3b-containing complex, e.g. as determined by analysis of the subject, or a sample (e.g. a cell, tissue, blood sample) obtained from the subject, using an appropriate assay.

The subject may have an increased level of expression or activity of a positive regulator/effector of C3b or a C3b-containing complex or of an activity/response associated with C3b or a C3b-containing complex, or may have an increased level of expression or activity of a product of an activity/response associated with C3b or a C3b-containing complex. The subject may have an increased level of an activity upregulated by C3b or a C3b-containing complex.

The subject may have a reduced level of expression or activity of a negative regulator of C3b or a C3b-containing complex or of an activity/response associated with C3b or a C3b-containing complex, or may have a reduced level of expression or activity a factor downregulated by C3b or a C3b-containing complex. The subject may have a reduced level of an activity downregulated by C3b or a C3b-containing complex.

The increase/reduction may be relative to the level of expression/activity in the absence of the relevant disease/condition, e.g. the level of expression/activity in a healthy control subject or sample obtained from a healthy control subject.

In some embodiments, the subject may be at risk of developing/contracting a disease or condition. In some embodiments, the subject may possess one or more predisposing factors increasing risk of developing/contracting a disease or condition.

In some embodiments, the subject may possess one or more risk factors for Age-related Macular Degeneration (AMD). In some embodiments, the subject may possess one or more of AMD-associated genetic variants. AMD-associated genetic variants are described e.g. in Clark et al., J Clin Med (2015) 4(1):18-31, which is hereby incorporated by reference in its entirety. In some embodiments, the subject may possess one or more of the following AMD-associated genetic variants (or a variant having LD=$r^2 \geq 0.8$ with such variant): Y402H in CFH (i.e. rs1061170$^C$), rs1410996c$^·$ 162V in CFH, R53C in CFH, D90G in CFH, R1210C in CFH, or rs6685931$^T$ in CFHR4.

In some embodiments the subject may possess one or more risk factors for early-onset macular degeneration (EOMD). EOMD is thought to be caused by monogenic inheritance of rare variants of the CFH gene (see e.g. Boon C J et al. Am J Hum Genet 2008; 82(2):516-23; van de Ven J P, et al. Arch Ophthalmol 2012; 130(8):1038-47; Yu Y et al. Hum Mol Genet 2014; 23(19):5283-93; Duvvari M R, et al. Mol Vis 2015; 21:285-92; Hughes A E, et al. Acta Ophthalmol 2016; 94(3):e247-8; Wagner et al. Sci Rep 2016; 6:31531). In some embodiments, the subject may possess one or more of EOMD-associated genetic variants. EOMD-associated genetic variants are described in e.g. Servais A et al. Kidney Int, 2012; 82(4):454-64 and Dragon-Durey M A, et al. J Am Soc Nephrol 2004; 15(3):787-95; which are hereby incorporated by reference in their entirety. In some embodiments, the subject may possess one or more of the following EOMD-associated genetic variants: CFH c.1243del, p.(Ala415Profs*39) het; CFH c.350+1G>T het;

CFH c.619+1G>A het; CFH c.380G>A, p.(Arg127His); CFH c.694C>T, p.(Arg232Ter); or CFH c.1291T>A, p.(Cys431Ser).

In some embodiments, the subject is selected for therapeutic or prophylactic treatment with the polypeptide, nucleic acid, vector, cell or composition of the present invention based on their being determined to possess one or more risk factors for AMD and/or EOMD, e.g. one or more AMD/EOMD-associated genetic variants. In some embodiments, the subject has been determined to have one or more such risk factors. In some embodiments, the methods of the present invention involving determining whether a subject possesses one or more such risk factors.

In some embodiments, the disease or condition to be treated or prevented may be an ocular disease/condition. In some embodiments, the disease or condition to be treated or prevented is a complement-related ocular disease. In some embodiments, the disease or condition to be treated or prevented is macular degeneration. In some embodiments, the disease or condition to be treated or prevented is age-related macular degeneration (AMD). AMD is commonly-defined as causing vision loss in subjects age 50 and older.

In some embodiments, the disease or condition to be treated or prevented is selected from age-related macular degeneration (AMD), early AMD, intermediate AMD, late AMD, geographic atrophy ('dry' (i.e. non-exudative) AMD), 'wet' (neovascular or exudative) AMD, choroidal neovascularisation (CNV), glaucoma, autoimmune uveitis, and diabetic retinopathy. In some embodiments, the disease or condition to be treated or prevented is AMD. In some embodiments, the disease or condition to be treated or prevented is geographic atrophy ('dry' AMD). In some embodiments, the disease or condition to be treated or prevented is 'wet' AMD. In some embodiments the disease or condition to be treated or prevented is a combination of the diseases/conditions above, e.g. 'dry' and 'wet' AMD. In some embodiments the disease or condition to be treated or prevented is not 'wet' AMD or choroidal neovascularisation. In some embodiments a subject to be treated is age 50 or older, i.e. is at least 50 years old.

As used herein "early AMD" refers to a stage of AMD characterised by the presence of medium-sized drusen, commonly having a width of up to ~200 μm, within the Bruch's membrane adjacent to the RPE layer. Subjects with early AMD typically do not present significant vision loss. As used herein "intermediate AMD" refers to a stage of AMD characterised by large drusen and/or pigment changes in the retina. Intermediate AMD may be accompanied by some vision loss. As used herein "late AMD" refers to a stage of AMD characterised by the presence of drusen and vision loss due to damage to the macula. In all stages of AMD, 'reticular pseudodrusen' (RPD) or 'reticular drusen' may be present, referring to the accumulation of extracellular material in the subretinal space between the neurosensory retina and RPE. "Late AMD" encompasses 'dry' and 'wet' AMD. In 'dry' AMD (also known as geographic atrophy), there is a gradual breakdown of the light-sensitive cells in the macula that convey visual information to the brain and of the supporting tissue beneath the macula. In 'wet' AMD (also known as choroidal neovascularization and exudative AMD), abnormal blood vessels grow underneath and into the retina. These vessels can leak fluid and blood which can lead to swelling and damage of the macula and subsequent scar formation. The damage may be rapid and severe.

In some embodiments the disease or condition to be treated or prevented is early-onset macular degeneration (EOMD). As used herein "EOMD" refers to a phenotypically severe sub-type of macular degeneration that demonstrates a much earlier age of onset than classical AMD and results in many more years of substantial visual loss. The EOMD subset is described in e.g. Boon C J et al. Am J Hum Genet 2008; 82(2):516-23 and van de Ven J P, et al. Arch Ophthalmol 2012; 130(8):1038-47. In some embodiments a subject to be treated is age 49 or younger. In some embodiments a subject to be treated is between ages 15 and 49, i.e. is between 15 and 49 years old.

In some embodiments, the disease or condition to be treated or prevented is a disease/condition driven by complement over-activation. In some embodiments, the disease or condition to be treated or prevented may be selected from atypical Haemolytic Uremic Syndrome (aHUS), Membranoproliferative Glomerulonephritis Type II (MPGN II), sepsis, and Paroxysmal nocturnal hemoglobinuria (PNH).

Methods of medical treatment may also involve in vivo, ex vivo, and adoptive immunotherapies, including those using autologous and/or heterologous cells or immortalized cell lines.

Administration of a polypeptide described herein is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the condition to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Polypeptides, nucleic acids, vectors and cells according to the present invention may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, subretinal, suprachoroidal, subcutaneous, intradermal, intrathecal, oral or transdermal routes of administration which may include injection or infusion, or administration as an eye drop (i.e. ophthalmic administration). Suitable formulations may comprise the polypeptide, nucleic acid, vector, or cell in a sterile or isotonic medium. Medicaments and pharmaceutical compositions may be formulated in fluid, including gel, form. Fluid formulations may be formulated for administration by injection or infusion (e.g. via catheter) to a selected organ or region of the human or animal body. In some embodiments the polypeptides, nucleic acids, vector, cells and compositions of the invention are formulated for intravitreal routes of administration e.g. by intravitreal injection. In some embodiments polypeptides, nucleic acids, vector, cells and compositions of the invention are formulated for submacular delivery i.e. placing the therapeutic molecules in direct contact with the target cell layers.

The particular mode and/or site of administration may be selected in accordance with the location where the C3b inactivation is desired. In some embodiments, the polypeptides, nucleic acids, vectors, or pharmaceutical compositions of the present invention are formulated for administration and/or administered into the subretinal space between the photoreceptor cells and the retinal pigment epithelium (RPE) in the eye. In some embodiments, the polypeptides, nucleic acids, vectors, or pharmaceutical compositions of the present invention are formulated for administration and/or administered into the retinal pigment epithelium (RPE).

In accordance with the present invention methods are also provided for the production of pharmaceutically useful compositions, such methods of production may comprise one or more steps selected from: isolating a polypeptide, nucleic acid, vector, or cell as described herein; and/or mixing a polypeptide, nucleic acid, vector, or cell as described herein with a pharmaceutically acceptable carrier, adjuvant, excipient or diluent.

For example, a further aspect of the present invention relates to a method of formulating or producing a medicament or pharmaceutical composition for use in a method of medical treatment, the method comprising formulating a pharmaceutical composition or medicament by mixing polypeptide, nucleic acid, vector, or cell as described herein with a pharmaceutically acceptable carrier, adjuvant, excipient or diluent.

Administration may be alone or in combination with other treatments (e.g. other therapeutic or prophylactic intervention), either simultaneously or sequentially dependent upon the condition to be treated. The polypeptide, nucleic acid, vector, cell or composition according to the present invention and a therapeutic agent may be administered simultaneously or sequentially.

Simultaneous administration refers to administration of the polypeptide, nucleic acid, vector, cell or composition and therapeutic agent together, for example as a pharmaceutical composition containing both agents (combined preparation), or immediately after each other and optionally via the same route of administration, e.g. to the same tissue, artery, vein or other blood vessel. Sequential administration refers to administration of one of the polypeptide, nucleic acid, vector, cell or composition or therapeutic agent followed after a given time interval by separate administration of the other agent. It is not required that the two agents are administered by the same route, although this is the case in some embodiments. The time interval may be any time interval. In some embodiments, the polypeptide, nucleic acid, vector, cell or composition and therapeutic agent are administered separately, simultaneously or sequentially to the eye.

In some embodiments, the other treatment/therapeutic agent is a therapeutically effective amount of Complement Factor I. In some embodiments, Complement Factor I is administered to the subject simultaneously or sequentially with administration of a polypeptide, nucleic acid, vector, cell, or pharmaceutical composition according to the present invention. In some embodiments, the treatment may comprise modifying a cell or population of cells in vitro, ex vivo or in vivo to express and/or secrete Complement Factor I. The cell or population of cells may be the same cell or population of cells as a cell or population of cells modified to comprise/express a polypeptide, nucleic acid or vector according to the present invention, for example the treatment may comprise modifying a cell or population of cells in vitro, ex vivo or in vivo to express and/or secrete a polypeptide, nucleic acid or vector according to the present invention, and Complement Factor I. In some embodiments, Complement Factor I is administered to a subject, wherein the subject comprises a cell or population of cells modified to comprise/express a polypeptide, nucleic acid or vector of the present invention. In some embodiments, Complement Factor I is administered to a subject wherein the subject has expressed in situ or is expressing in situ a polypeptide, nucleic acid or vector of the present invention.

Complement Factor I, or a composition comprising Complement Factor I, may be formulated for topical, parenteral, systemic, intracavitary, intravenous, intravitreal, intra-arterial, intramuscular, intrathecal, intraocular, intraconjunctival, subretinal, suprachoroidal, subcutaneous, intradermal, intrathecal, oral or transdermal routes of administration which may include injection or infusion, or administration as an eye drop (i.e. ophthalmic administration). Suitable formulations may comprise a sterile or isotonic medium. Medicaments and pharmaceutical compositions may be formulated in fluid, including gel, form. Fluid formulations may be formulated for administration by injection or infusion (e.g. via catheter) to a selected organ or region of the human or animal body.

In some embodiments, the other treatment/therapeutic agent is a therapeutically effective amount of an anti-VEGF therapy (e.g. ranibizumab (Lucentis; Genentech/Novartis), bevacizumab (off label Avastin; Genentech), aflibercept (Eylea/VEGF Trap-Eye; Regeneron/Bayer)), pegaptanib (Macugen), laser photocoagulation, or photodynamic therapy (PDT) e.g. with Visudyne™ (verteporfin).

Multiple doses of the polypeptide, nucleic acid, vector, cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

A polypeptide, nucleic acid, vector or composition according to the present invention may be formulated in a sustained release delivery system, in order to release the polypeptide, nucleic acid, vector or composition at a predetermined rate. Sustained release delivery systems may maintain a constant drug/therapeutic concentration for a specified period of time. In some embodiments, a polypeptide, nucleic acid, vector or composition according to the present invention is formulated in a liposome, gel, implant, device, or drug-polymer conjugate e.g. hydrogel.

Genetic Factors in Age-Related Macular Degeneration (AMD)

Complement Factor H (encoded by the CFH gene) is another co-factor for Complement Factor I. Complement Factor H structure and function is reviewed e.g. in Wu et al., Nat Immunol (2009) 10(7): 728-733, which is hereby incorporated by reference in its entirety. Human Complement Factor H (UniProt: P08603; SEQ ID NO:29) has a 1,233 amino acid sequence (including an N-terminal, 18 amino acid signal peptide), and comprises 20 complement control protein (CCP) domains. The first four CCP domains (i.e. CCP1 to CCP4) of Complement Factor H are necessary for Complement Factor I co-factor activity for cleavage of C3b to iC3b. CCPs 19 to 20 have also been shown to engage with C3b and C3d (Morgan et al., Nat Struct Mol Biol (2011) 18(4): 463-470), whilst CCP7 and CCPs 19 to 20 bind to glycosaminoglycans (GAGs) and sialic acid, and are involved in discrimination between self and non-self (Schmidt et al., J Immunol (2008) 181(4): 2610-2619; Kajander et al., PNAS (2011) 108(7): 2897-2902).

One of the major SNPs associated with genetic risk of developing AMD is found in the CFH gene and leads to the Y402H polymorphism in Complement Factor H (see e.g. Haines et al., Science (2005) 308:419-21), and it's alternative splice variant factor H-like protein 1 (FHL-1). Around 30% of individuals of white European heritage have at least one copy of this polymorphism, whilst being a heterozygote increases the risk of AMD by ~3-fold (Sofat et al., Int J Epidemiol (2012) 41:250-262). The Y402H polymorphism, which manifests in the seventh complement control protein (CCP) domain, reduces the binding of FH/FHL-1 to BrM, leading to perturbations in the binding of these blood-borne complement regulators and dampened complement regulation on this surface (Clark et al., J Biol Chem (2010) 285:30192-202).

The binding of FH/FHL-1 to BrM is mediated by sulphated sugars including the glycosaminoglycans (GAGs) heparan sulphate (HS) and dermatan sulphate (DS). The family of GAG sequences found in BrM appears to have greater tissue specificity than previously thought, as they are able to recruit FH/FHL-1 through their CCP7 domains and not FH's secondary anchoring site found in CCPs19-20 (Clark et al., J Immunol (2013) 190:2049-2057). This is likely to be an evolutionary twist, as it has been discovered that the main regulator of complement within BrM is the truncated FHL-1 protein (Clark et al J. Immunol (2014) 193, 4962-4970), which only has the one surface anchoring site in CCP7 and lacks CCPs19-20. In contrast, the Y402H polymorphism is not associated with kidney disease where the CCP19-20 domain of FH is known to be the main GAG-mediated anchoring site (Clark et al., J Immunol (2013) 190:2049-2057). Age-related changes in the BrM expression levels of HS and DS, themselves considered part of the normal ageing process, have also been associated with AMD, and may go some way as to explain the age-related nature of the genetically driven AMD.

A rare mutation (R1210C) in the C-terminal CCP19-20 region of FH, which does not bind to BrM, has a very high level of association with AMD, and FH protein carrying this mutation is found covalently bound to albumin (Sánchez-Corral et al., Am J Hum Genet (2002) 71:1285-1295) preventing the FH protein from leaving the circulation and entering eye tissue. Some research suggests that the large confluent drusen that precede geographic atrophy and the associated pigmentary changes in the RPE indicate that dry AMD results firstly from dysfunction of the RPE with secondary effects within the choroid (Bhutto and Lutty Mol Aspects Med (2012) 33:295-317). In contrast, Whitmore et al. reported changes in the choriocapillaris preceding all forms of late-stage AMD including the deposition of the terminal complement membrane attack complex (MAC), and argue that excessive complement activation in the choriocapillaris is the primary event with RPE atrophy being secondary (Whitmore et al., Prog Retin Eye Res (2015) 45:1-29). These data imply that a genetic predisposition conferred by alterations in complement genes is tolerated until changes in both BrM and the underlying choriocapillaris come to the fore. Whether these changes are age-related, driven by oxidative stress or a result of RPE cell dysfunction remains to be seen, but naturally occurring changes in these structures are known to be age-related.

C3 and C3b

Complement component 3 (C3) is an immune system protein having a central role in innate immunity and the complement system. Processing of C3 is described, for example, in Foley et al. J Thromb Haemostasis (2015) 13: 610-618, which is hereby incorporated by reference in its entirety. Human C3 (UniProt: P01024; SEQ ID NO:18) comprises a 1,663 amino acid sequence (including an N-terminal, 22 amino acid signal peptide). Amino acids 23 to 667 encode C3 β chain (SEQ ID NO:19), and amino acids 749 to 1,663 encode C3 α' chain (SEQ ID NO:20). C3 β chain and C3 α' chain associate through interchain disulphide bonds (formed between cysteine 559 of C3 β chain, and cysteine 816 of the C3 α' chain) to form C3b. C3a is a 77 amino acid fragment corresponding to amino acid positions 672 to 748 of C3 (SEQ ID NO:21), generated by proteolytic cleavage of C3 following activation through the classical complement pathway and the lectin pathways.

C3b is a potent opsonin, targeting pathogens, antibody-antigen immune complexes and apoptotic cells for phagocytosis by phagocytes and NK cells. C3b is also involved in the formation of convertase enzyme complexes for activating and amplifying complement responses. C3b associates with Factor B to form the C3bBb-type C3 convertase (alternative complement pathway), and can associate with C4b and C2a to form the C4b2a3b-type C5 convertase (classical pathway), or with C3bBb to form the C3bBb3b-type C5 convertase (alternative pathway).

Processing of C3b to the form iC3b, which is proteolytically inactive and which cannot itself promote further complement amplification, involves proteolytic cleavage of the C3b α' chain at amino acid positions 1303 and 1320 to form an α' chain fragment 1 (corresponding to amino acid positions 672 to 748 of C3; SEQ ID NO:22), an α' chain fragment 2 (corresponding to amino acid positions 1321 to 1,663 of C3; SEQ ID NO:23). Thus, iC3b comprises the C3 β chain, C3 α' chain fragment 1 and C3 α' chain fragment 2 (associated via disulphide bonds). Cleavage of the α' chain also liberates C3f, which corresponds to amino acid positions 1304 to 1320 of C3 (SEQ ID NO:24).

As used herein "C3" refers to C3 from any species and include isoforms, fragments, variants or homologues of C3 from any species. In some embodiments, the C3 is mammalian C3 (e.g. cynomolgous, human and/or rodent (e.g. rat and/or murine) C3). Isoforms, fragments, variants or homologues of C3 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature C3 from a given species, e.g. human C3 (SEQ ID NO:18).

As used herein "C3b" refers to and includes isoforms, fragments, variants or homologues of C3b from any species. In some embodiments, the C3b is mammalian C3b (e.g. cynomolgous, human and/or rodent (e.g. rat and/or murine) C3b).

Isoforms, fragments, variants or homologues of C3b may optionally be characterised as comprising a C3 α' chain fragment 1, C3 α' chain fragment 2 and a C3 β having at least 70%, preferably one of 80%, 85%, 90%, 91%, 92%, 93%, 94%, 95%, 96%, 97%, 98%, 99% or 100% amino acid sequence identity to the amino acid sequences of the respective polypeptides from a given species, e.g. human. That is, the C3b may comprise: a C3 α' chain fragment 1 having at least 70%, preferably one of 80%, 85%, 90%, 91%, 92%, 93%, 94%, 95%, 96%, 97%, 98%, 99% or 100% amino acid sequence identity to SEQ ID NO:22; a C3 α' chain fragment 2 having at least 70%, preferably one of 80%, 85%, 90%, 91%, 92%, 93%, 94%, 95%, 96%, 97%, 98%, 99% or 100% amino acid sequence identity to SEQ ID NO:23; and a C3 β chain having at least 70%, preferably one of 80%, 85%, 90%, 91%, 92%, 93%, 94%, 95%, 96%, 97%, 98%, 99% or 100% amino acid sequence identity to SEQ ID NO:19.

Isoforms, fragments, variants or homologues of C3b may optionally be functional isoforms, fragments, variants or homologues, e.g. having a functional property/activity of the reference C3b, as determined by analysis by a suitable assay for the functional property/activity. For example, Isoforms, fragments, variants or homologues of C3b may be characterised by the ability to act as an opsonin, and/or to form functional C3/C5 convertase.

Complement Factor I

Processing of C3b to iC3b is performed by Complement Factor I (encoded in humans by the gene CF). Human Complement Factor I (UniProt: P05156; SEQ ID NO:25) has a 583 amino acid sequence (including an N-terminal, 18 amino acid signal peptide). The precursor polypeptide is cleaved by furin to yield the mature Complement Factor I, comprising a heavy chain (amino acids 19 to 335), and light chain (amino acids 340 to 583) linked by interchain disulphide bonds. Amino acids 340 to 574 of the light chain encode the proteolytic domain of Complement Factor I (SEQ ID NO:26), which is a serine protease containing the catalytic triad responsible for cleaving C3b to produce iC3b (Ekdahl et al., J Immunol (1990) 144 (11): 4269-74).

As used herein "Complement Factor I (FI)" refers to Complement Factor I from any species and includes isoforms, fragments, variants or homologues of Complement Factor I from any species. In some embodiments, the Complement Factor I is mammalian Complement Factor I (e.g. cynomolgous, human and/or rodent (e.g. rat and/or murine) Complement Factor I).

Isoforms, fragments, variants or homologues of Complement Factor I may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature Complement Factor I from a given species, e.g. human Complement Factor I (SEQ ID NO:25). Isoforms, fragments, variants or homologues of Complement Factor I may optionally be functional isoforms, fragments, variants or homologues, e.g. having a functional property/activity of the reference Complement Factor I (e.g. full-length human Complement Factor I), as determined by analysis by a suitable assay for the functional property/activity. For example, an isoform, fragment, variant or homologue of Complement Factor I may display serine protease activity and/or may be capable of inactivating C3b.

Proteolytic cleavage of C3b by Complement Factor I to yield iC3b is facilitated by co-factors for Complement Factor I. Co-factors for Complement Factor I typically bind to C3b and/or Complement Factor I, and potentiate processing of C3b to iC3b by Complement Factor I.

Complement Receptor 1

Complement Receptor 1 (CR1) acts as a cofactor for Complement Factor I, enabling cleavage of C3b to iC3b and downstream products.

iC3b does not amplify or activate the complement system, but it can still act as an opsonin to target pathogens for phagocytosis. iC3b production therefore results in local immune system activation and inflammatory effects. This can have negative consequences for sufferers of complement-related disease and may contribute to the development or worsening of an existing complement-related disease/condition.

Factor H (FH) and truncated FH isoform FHL-1 act as co-factors for FI to produce iC3b, but they cannot promote further degradation of iC3b which can lead to undesirable iC3b accumulation. In addition, the accumulation of iC3b may contribute to further debris in the affected area, leading to e.g. the (further) development of drusen in macular degeneration.

In contrast, CR1 and the polypeptides according to the present invention, see e.g. FIGS. 2, 3B, 7A, can act in combination with FI to promote further breakdown of iC3b into advantageous downstream products such as C3c, C3dg and C3b. These molecules are not opsonins and thus avoid recruiting immune system components. Their presence in an affected area is preferable to iC3b accumulation. As used herein, "Complement Receptor 1 (CR1)" refers to CR1 from any species and includes isoforms, fragments, variants or homologues of CR1 from any species. In some embodiments, the CR1 is mammalian CR1 (e.g. cynomolgous, human and/or rodent (e.g. rat and/or murine) CR1).

Aspects and embodiments of the present invention will now be illustrated, by way of example, with reference to the accompanying figures. Further aspects and embodiments will be apparent to those skilled in the art. All documents mentioned in this text are incorporated herein by reference.

The invention includes the combination of the aspects and preferred features described except where such a combination is clearly impermissible or expressly avoided.

The section headings used herein are for organizational purposes only and are not to be construed as limiting the subject matter described.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence in disclosed the reverse complement thereof is also expressly contemplated.

The following numbered paragraphs (paras) describe particular aspects and embodiments of the present invention:

1. A polypeptide having at least 80% sequence identity to SEQ ID NO:4, wherein the polypeptide has a length of 700 amino acids or fewer.

2. The polypeptide according to para 1, wherein the polypeptide has a length of 50 to 700 amino acids.

3. The polypeptide according to para 1 or 2, wherein $X_1$ is A or T, $X_2$ is P or L, and/or $X_3$ is G or R.

4. The polypeptide according to any one of paras 1 to 3, comprising SEQ ID NO:2, SEQ ID NO:3 or SEQ ID NO:13.

5. The polypeptide according to any one of paras 1 to 4, consisting of SEQ ID NO:2, SEQ ID NO:3, or SEQ ID NO:13.

6. The polypeptide according to any one of paras 1 to 5, which is capable of binding to C3b.

7. The polypeptide according to any one of paras 1 to 6, which binds to C3b in the region bound by a co-factor for Complement Factor I.

8. The polypeptide according to any one of paras 1 to 7, which binds to C3b in the region bound by Complement Receptor 1 (CR1).

9. The polypeptide according to any one of paras 1 to 8, which acts as a co-factor for Complement Factor I.

10. The polypeptide according to any one of paras 1 to 9, which is capable of diffusing across Bruch's membrane (BrM).

11. The polypeptide according to any one of paras 1 to 10, which is not glycosylated or is partially glycosylated.

12. The polypeptide according to any one of paras 1 to 11, wherein the amino acid sequence comprises one or more amino acid substitutions at position 509, 578, 959 and/or 1028 (numbered according to Uniprot: P17927).

13. The polypeptide according to para 12, wherein the one or more amino acid substitutions are selected from N509Q, N578Q, N959Q and/or N1028Q (numbered according to Uniprot: P17927).

14. The polypeptide according to any one of paras 1 to 13, comprising, or consisting, of SEQ ID NO:5, SEQ ID NO:6, and/or SEQ ID NO:15.

15. The polypeptide according to any one of paras 1 to 14, additionally comprising a secretory pathway sequence.

16. The polypeptide according to para 15, wherein the secretory pathway sequence comprises SEQ ID NO:7.

17. The polypeptide according to para 15 or para 16, wherein the polypeptide additionally comprises a cleavage site for removing the secretory pathway sequence.

18. A nucleic acid encoding the polypeptide according to any one of paras 1 to 17.

19. A vector comprising the nucleic acid of para 18.

20. A cell comprising the polypeptide according to any one of paras 1 to 17, the nucleic acid according to para 18, or the vector according to para 19.

21. A method for producing a polypeptide, comprising introducing into a cell a nucleic acid according to para 18 or a vector according to para 19, and culturing the cell under conditions suitable for expression of the polypeptide.

22. A cell which is obtained or obtainable by the method according to para 21.

23. A pharmaceutical composition comprising the polypeptide according to any one of paras 1 to 17, the nucleic acid according to para 18, the vector according to para 19, or the cell according to para 20 or 22, optionally comprising a pharmaceutically acceptable carrier, adjuvant, excipient, or diluent.

24. The polypeptide according to any one of paras 1 to 17, the nucleic acid according to para 18, the vector according to para 19, the cell according to para 20 or 22, or the pharmaceutical composition according to para 23, for use in a method of treating or preventing a disease or condition.

25. Use of the polypeptide according to any one of paras 1 to 17, the nucleic acid according to para 18, the vector according to para 19, the cell according to para 20 or 22, or the pharmaceutical composition according to para 23, in the manufacture of a medicament for treating or preventing a disease or condition.

26. A method of treating or preventing a disease or condition, comprising administering to a subject the polypeptide according to any one of paras 1 to 17, the nucleic acid according to para 18, the vector according to para 19, the cell according to para 20 or 22, or the pharmaceutical composition according to para 23.

27. A method of treating or preventing a disease or condition in a subject, comprising modifying at least one cell of the subject to express or comprise a polypeptide according to any one of paras 1 to 17, a nucleic acid according to para 18, or a vector according to para 19.

28. The polypeptide, nucleic acid, vector, cell, or pharmaceutical composition for use according to para 24, the use according to para 25, or the method according to para 26 or para 27, wherein the disease or condition is a disease or condition in which C3b or a C3b-containing complex, an activity/response associated with C3b or a C3b-containing complex, or a product of an activity/response associated with C3b or a C3b-containing complex is pathologically implicated.

29. The polypeptide, nucleic acid, vector, cell, or pharmaceutical composition for use, the use, or the method according to any one of paras 24 to 28, wherein the disease or condition is age-related macular degeneration (AMD).

30. The polypeptide, nucleic acid, vector, cell, or pharmaceutical composition for use, the use, or the method according to any one of paras 24 to 29, wherein the method for treating or preventing a disease or condition comprises modifying at least one retinal pigment epithelial (RPE) cell of the subject to express or comprise a polypeptide according to any one of paras 1 to 17, a nucleic acid according to para 18, or a vector according to para 19.

31. A kit of parts comprising a predetermined quantity of the polypeptide according to any one of paras 1 to 17, the nucleic acid according to para 18, the vector according to para 19, the cell according to para 20 or para 22 or the pharmaceutical composition according to para 23.

BRIEF DESCRIPTION OF THE FIGURES

Embodiments and experiments illustrating the principles of the invention will now be discussed with reference to the accompanying figures.

FIGS. 1A and 1B. CR1a and nCR1a protein expression from human HEK293 cells. (1A) CR1a is expressed as two glyco-forms that are reduced to one lower MW band after deglycosylation treatment with PNGase. (1B) nCR1a is expressed as single form of same MW as deglycosylated CR1a.

EXAMPLES

Figure 1A:
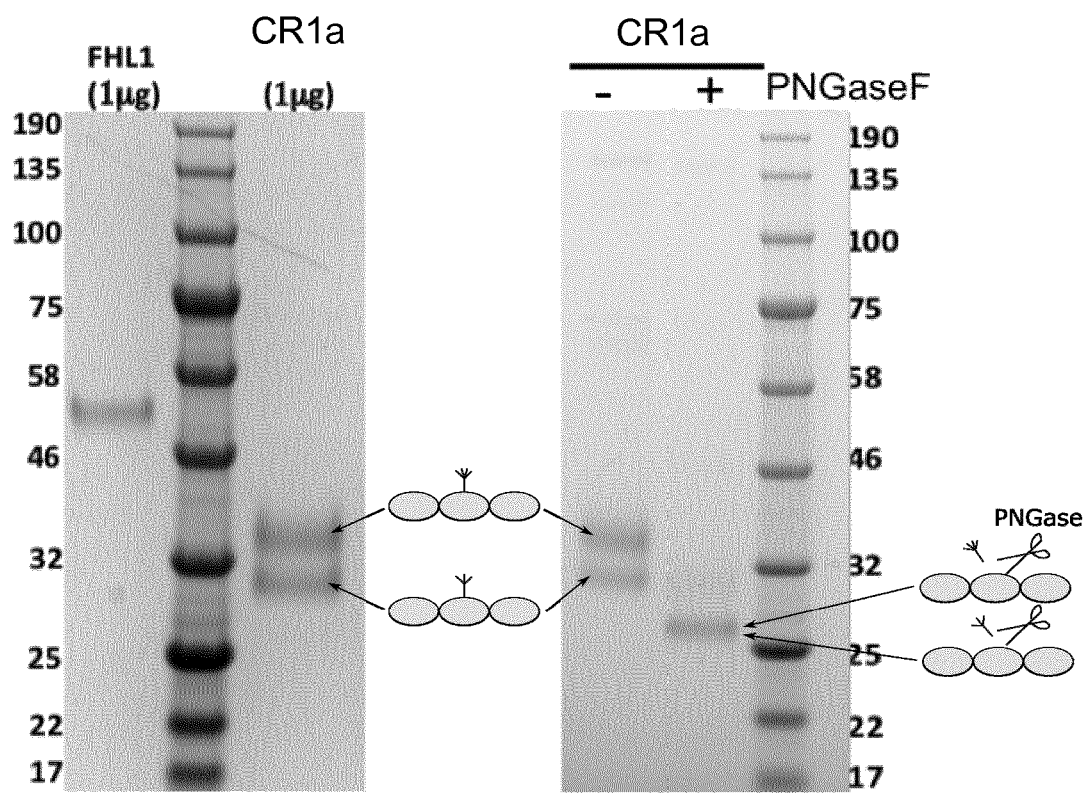

In the following Example(s), the inventors describe the design of recombinant CR1 proteins comprising the C3b binding co-factor regions of Complement Receptor 1. Also described is the ability of these proteins to be expressed by human cells, diffuse through Bruch's membrane enriched from human donor eyes, and confer regulatory activity, i.e. facilitate the FI-mediated breakdown of C3b into iC3b and further breakdown products.

Example 1

DNA inserts encoding the amino acid sequences shown in SEQ ID NOs:2 and 5 were prepared by recombinant DNA techniques, and cloned into a vector to generate constructs for recombinant expression of CR1 peptides. The amino acid sequences and features thereof are shown below:

CR1a (SEQ ID NO:47)

MRLLAKIICLMLWAICVAGHCQAPDHFLFAKLKTQ
TNASDFPIGTSLKYECRPEYYGRPFSITCLDNLV
WSSPKDVCKRKSCKTPPDPVNGMVHVITDIQVGSRI-
NYSCTTGHRLIGHSSAECILSGNAAHWSTKP
PICQRIPCGLPPTIANGDFISTNRENFHYGSVVTYRC-
NPGSGGRKVFELVGEPSIYCTSNDDQVGIWS
GPAPQCII

Signal peptide (SEQ ID NO:7); CCPs8-10 of CR1 (SEQ ID NO:2) (UniProt: P17927, residues 491-685)

nCR1a (SEQ ID NO:48)

MRLLAKIICLMLWAICVAGHCQAPDHFLFAKLKTQ
TQASDFPIGTSLKYECRPEYYGRPFSITCLDNLV
WSSPKDVCKRKSCK-
TPPDPVNGMVHVITDIQVGSRIQYSCTTGHRLIGHS-
SAECILSGNAAHWSTKP    PICQRIPCGLPPTIANGD-
FISTNRENFHYGSVVTYRCNPGSGGRKVFELVGEPSI
YCTSNDDQVGIWS GPAPQCII

Signal peptide (SEQ ID NO:7); CCPs8-10 of CR1 (SEQ ID NO:5) (UniProt: P17927, residues 491-685) comprising substitutions N509Q and N578Q The 18-amino acid signal peptide is designed to be cleaved from the polypeptides upon secretion.

In some experiments, HIS-tagged CR1a and nCR1a were used, e.g. as shown in SEQ ID NO:40 and 21, respectively.

Expression of Protein from Human Cells

HEK 293T cells ($7 \times 10^6$ cell per plate) were grown in 15 cm culture plates overnight in 17 ml of Dulbecco's Modified Eagle's Medium with high glucose (DMEM, Sigma, catalogue number D469) supplemented with 10% Foetal Bovine Serum (FBS, Sigma, catalogue number F9665) in 5% $CO_2$ incubator at 37° C. Once the cells reached 60% confluence they were transiently transfected with 14.4 µg plasmid expressing either CR1a (SEQ ID NO:2) or nCR1a (SEQ ID NO:5) linked to the signal peptide (SEQ ID NO:7) with 86.4 µl of 7.5 mM Polyethylenimine (PEI, Polysciences, catalogue number 24765-2) 150 mM NaCl (Fisher Scientific UK Ltd, catalogue number 1073592). For the negative control 14.4 µl of Tris-EDTA buffer was used instead of the plasmid DNA. Five hours after transfection, the transfection medium containing 10% FBS was replaced with 17.5 ml fresh DMEM with high glucose supplemented with 2% FBS (referred to henceforth as expression media). Expression media was collected 24, 48, 72 and 140 hours after transfection. 80 µl of 0.5 M Phenylmethanesulfonyl fluoride (PMSF, Sigma, Catalogue number P7626) was added to every 100 ml of expression media collected and stored at 4° C. Expression media collected after 24 hrs was used for diffusion and function studies described below.

Characterisation of Secreted Protein from Human Cells

Figure 1B:
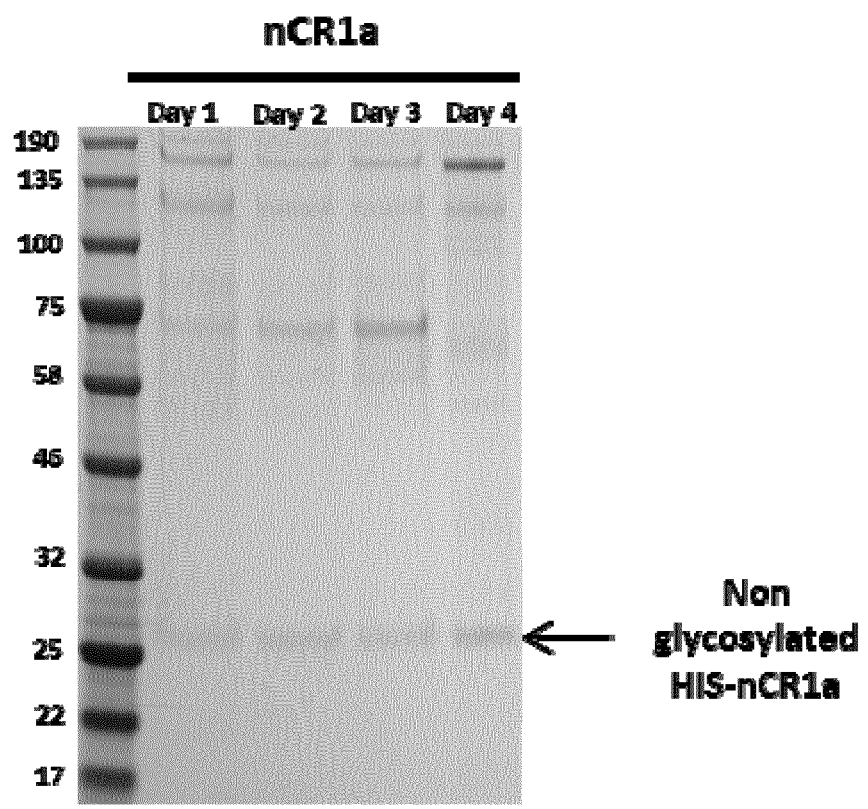

Protein expression from human cells is shown in FIGS. 1A and 1B. Recombinantly expressed and purified CR1a protein was found to be secreted from the cells as two glyco-forms. Treatment with PNGaseF, an enzyme that removes glycosylation, reduced the two bands to one band of lower apparent molecular weight (1A). A non-glycosylated form of the protein (nCR1a) was expressed. Western blotting demonstrated that nCR1a produces a single band that migrates to the same position as the enzymatically de-glycosylated protein (1B).

C3b Breakdown Activity

CR1a and nCR1a expressed and secreted from human HEK293 cells were tested for their ability to act as cofactors for Factor I-mediated breakdown of C3b.

1 µg of recombinant CR1a or nCR1a protein was mixed with 2 µg of pure C3b protein and 0.04 µg of pure complement Factor I (FI; VWR International, catalogue no. 341280) for 15 minutes at 37° C. FHL-1 was provided as a co-factor control for FI. CR1a/nCR1a, CR1a/nCR1a+FI, CR1a/nCR1a+C3b and C3b alone were also provided as controls. Reactions were stopped with the addition of 4×SDS-loading buffer and heating to 100° C. for 5 minutes. Samples were then run on 4-12% NuPAGE Bis-Tris gels, run at 200V for 60 minutes. Samples were transferred onto nitrocellulose membranes at 80 mA for 1.5 hours using semi-dry transfer apparatus in transfer buffer (25 mM Tris, 192 mM glycine, 10% (v/v) Methanol). The membranes were the blocked in PBS, 10% (w/v) milk, 0.2% (w/v) BSA for 16 hours at 4° C. before the addition of anti-C3b antibody (HycultBiotech, catalogue no. HM2287), at 100 µg/ml, in PBS, 0.2% (v/v) Tween-20 (PBS-T) for 1 hours at room temperature. Membranes were washed 2×30 min in PBS-T before the addition of a 1:2500 dilution of HRP conjugated goat anti-mouse for 1 hour at room temperature, protected from light. Membranes were washed 2×30 min in PBS-T before the addition of SuperSignal West Pico Chemiluminescent Substrate (Thermo Fisher Scientific, catalogue no. 34080) for 3 min at room temperature. Reactive bands were detected by exposing Super RX-N X-ray film (FujiFilm, catalogue no. PPB5080) to the treated membrane for 2 min at room temperature, and developed on an automated X-ray film developer.

Figure 2:
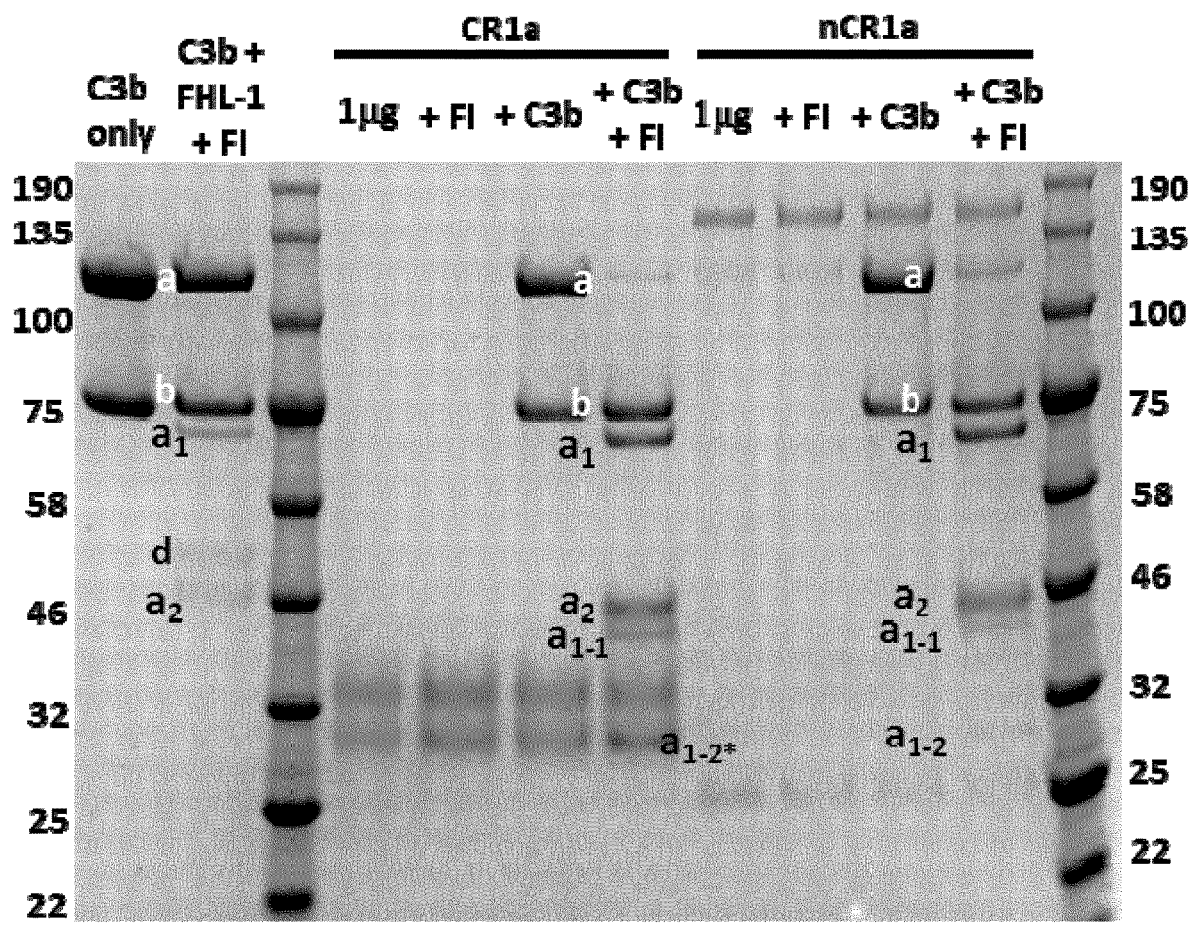
FIG. 2. The ability of CR1a and nCR1a expressed and secreted by human cells to act as cofactors for Factor I-mediated breakdown of C3b. CR1a/nCR1a+FI+C3b reactions produced iC3b and C3dg (lanes 7 and 11).

The results are shown in FIG. 2. Both secreted proteins were found to be able to act as cofactors for Factor I, leading to the breakdown of C3b to firstly iC3b ($a_1$), and further to C3dg ($a_{1-1}$). The C3b breakdown using CR1a/nCR1a continues further than the normal native breakdown of C3b observed using FI+FHL-1 (second lane), which only produces iC3b (a).

Ussing Chamber Diffusion Experiments and C3b Breakdown Activity

Figure 4:
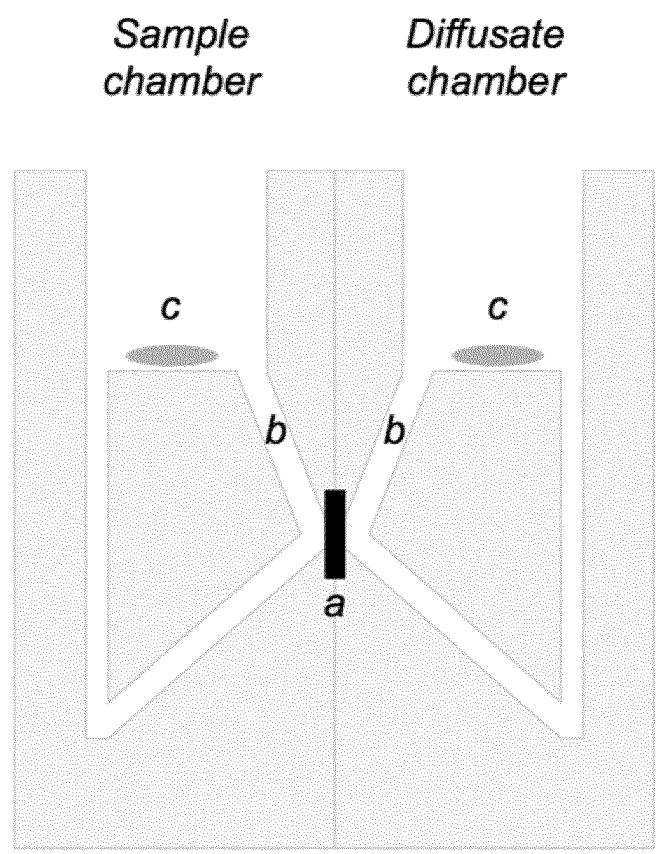
FIG. 4. Schematic of an Ussing chamber used in diffusion experiments, in which (a) is enriched Bruch's membrane from human donor eyes, covering a 5 mm aperture and representing the only passage of liquid from one chamber to another; (b) are sampling access points; and (c) are magnetic stirrer bars.

The macular region of enriched Bruch's membrane isolated from donor eyes was mounted in an Ussing chamber (Harvard Apparatus, Hamden, Conn.) as described in McHarg et al., J Vis Exp (2015) 1-7, supra. Once mounted, the 5-mm-diameter macular area was the only barrier between two identical compartments, i.e. liquid must pass through Bruch's membrane (FIG. 4). Both sides of Bruch's membrane were washed with 2 ml PBS for 5 min at room temperature. The structural integrity of Bruch's membrane was tested prior to the experiments by its ability to retain 2 ml of liquid in one chamber without leaking into the next. 2 ml of expression media containing recombinant protein (CR1a and/or nCR1a, see above) was added to a chamber (henceforth designated the sample chamber) and 2 ml of fresh PBS was added to the other chamber (henceforth referred to as the diffusate/diffusion chamber). The Ussing chamber was left at room temperature for 24 hours with gentle stirring in each compartment with magnetic stirrer bars to avoid generating gradients of diffusing protein.

CR1a was added to the sample chamber. After 24 hours, samples from each chamber (original sample chamber and diffusion chamber) were analysed for the presence of CR1a.

Figure 3A:
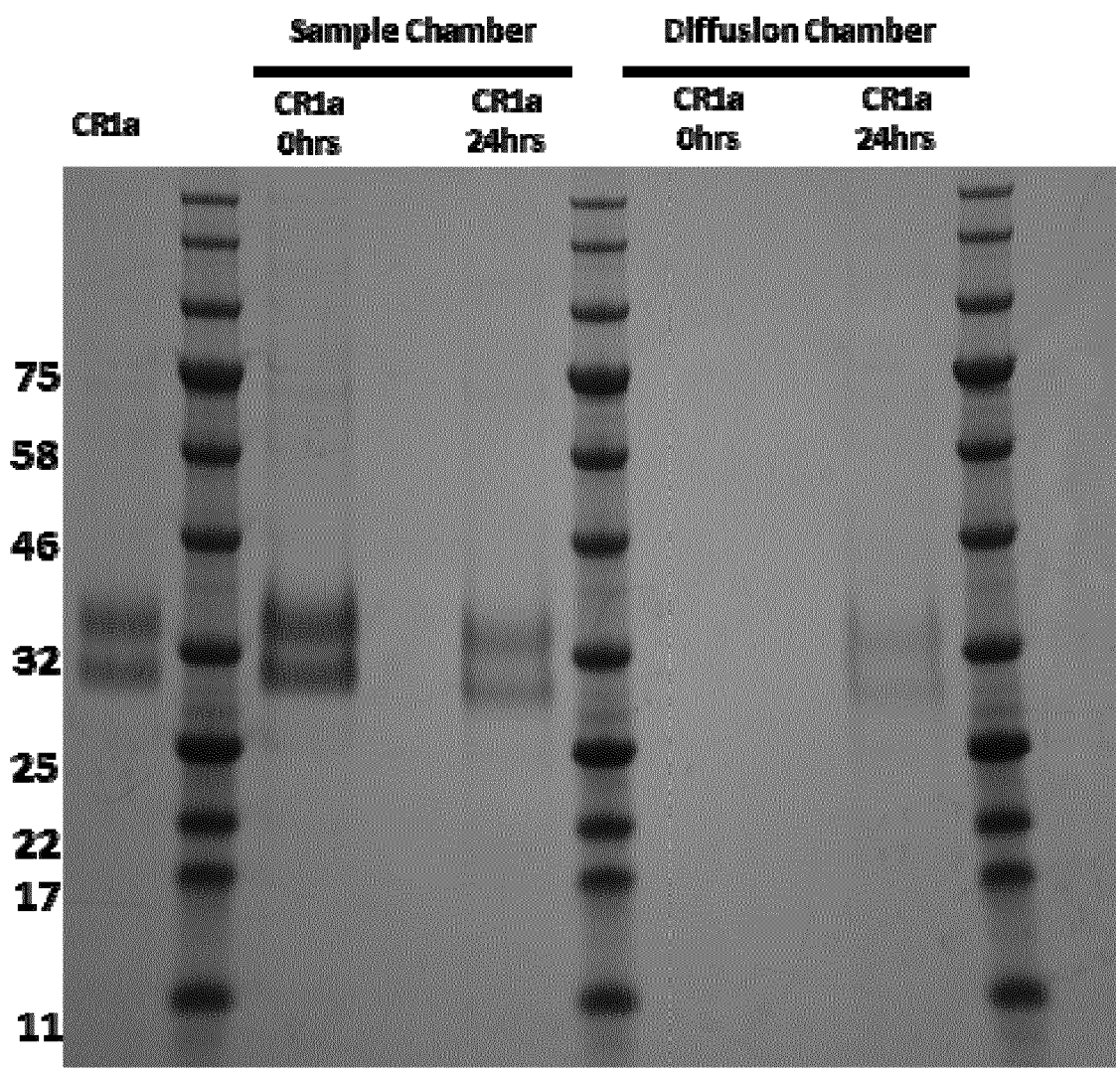
FIGS. 3A to 3C. (3A) Presence of CR1a in the diffusion chamber of an Ussing chamber after 24 hours, showing ability to diffuse through Bruch's membrane (BrM). (3B, 3C) The ability of (3B) CR1a and (3C) nCR1a to act as cofactors for Factor I to break down C3b after polypeptide diffusion through Bruch's membrane (BrM).

The results are shown in FIG. 3A. CR1a was found to be present in the diffusion chamber after 24 hours.

Separately, CR1a and nCR1a were added to sample chambers and samples from both chambers were analysed for C3b-breakdown activity. After 24 hours, 18.6 µl samples were taken from each chamber and mixed with 1 µl (1 µg) of pure C3b protein and 0.4 µl of pure complement factor I (0.04 µg, VWR International, catalogue no. 341280) for one of 15, 30, or 60 minutes at 37° C. Reactions were stopped with the addition of 4×SDS-loading buffer and heating to 100° C. for 5 minutes. Samples were then run on 4-12% NuPAGE Bis-Tris gels, run at 200V for 60 minutes.

Figure 3B:
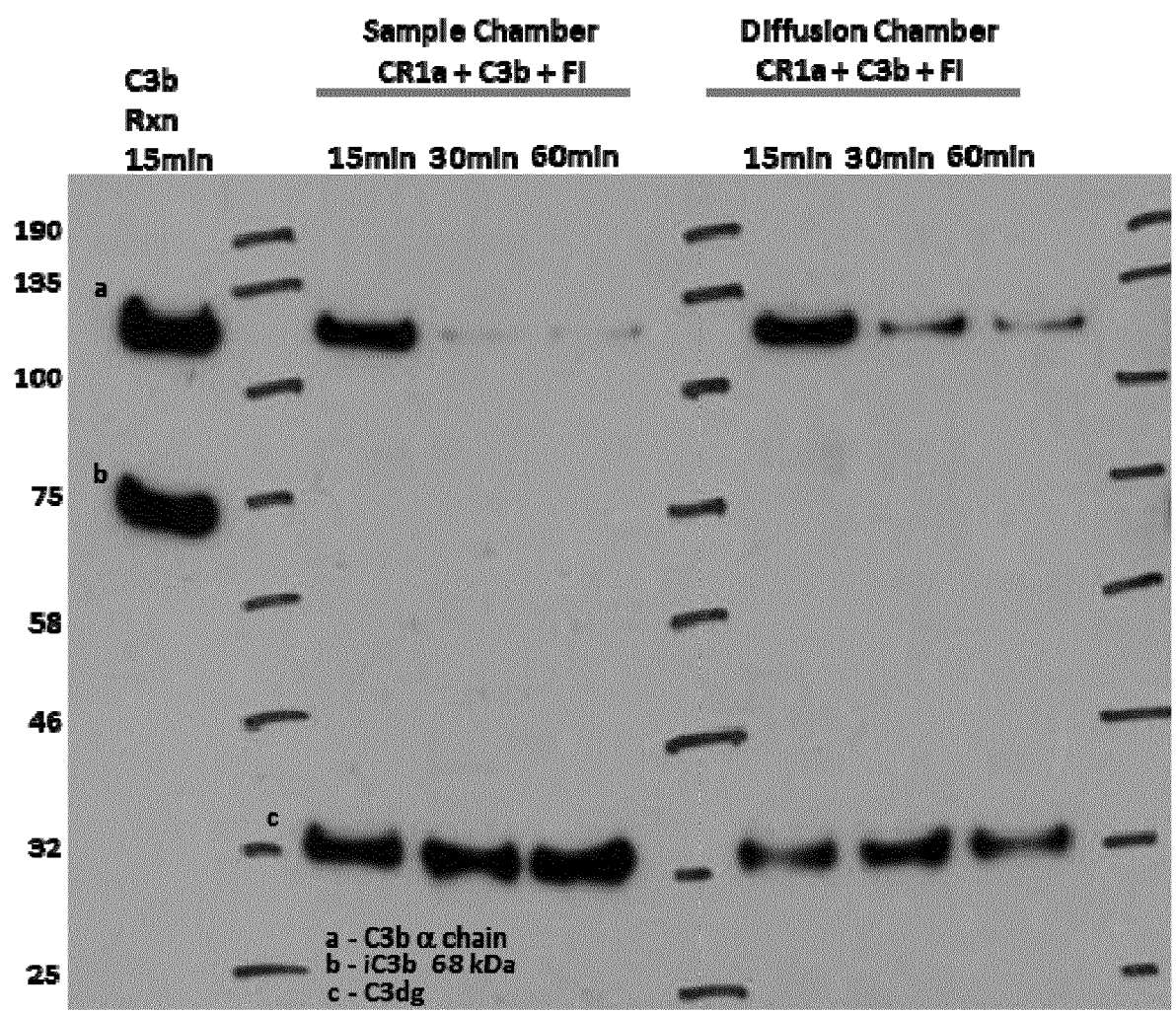
Figure 3C:
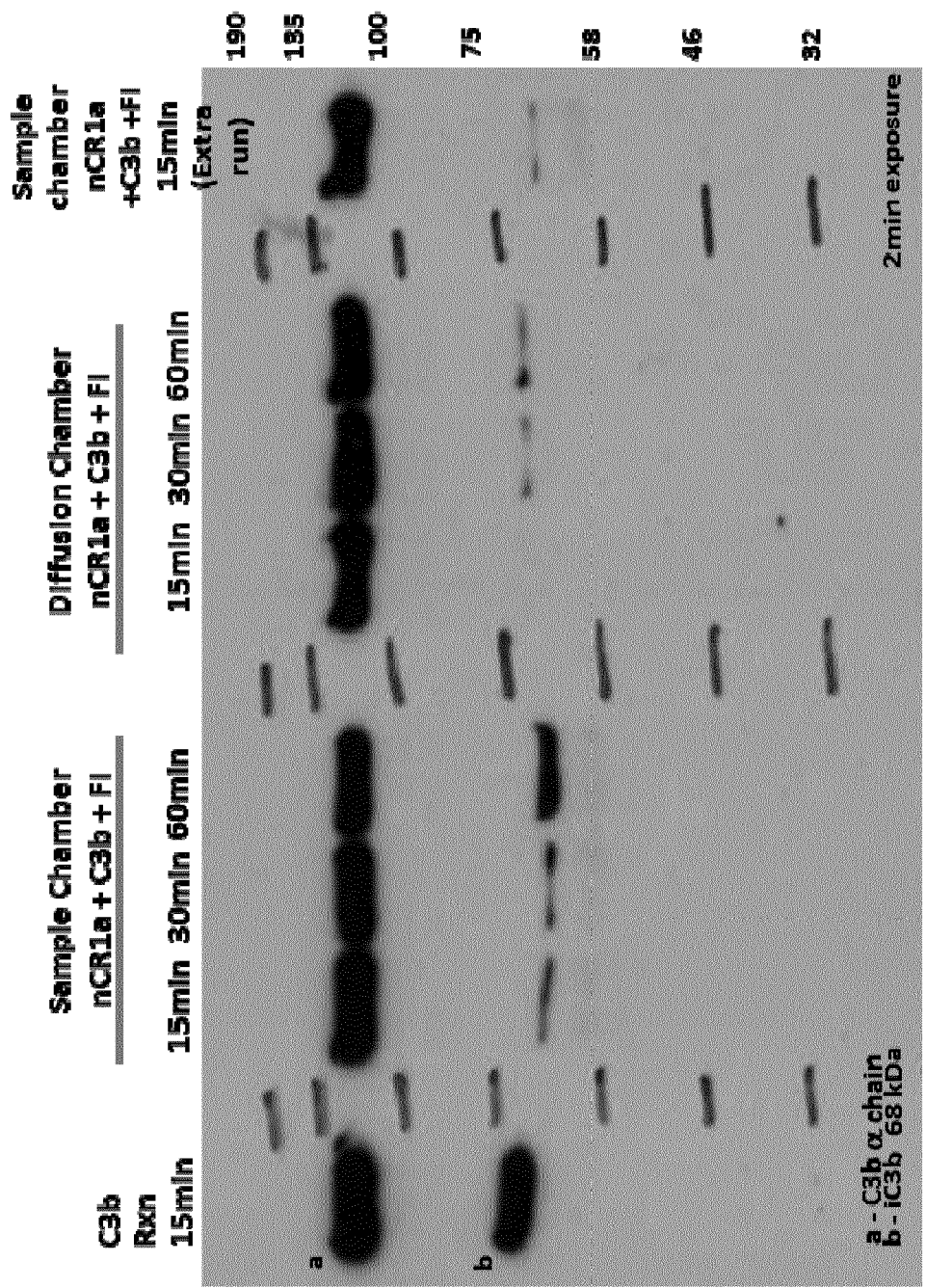

The results are shown in FIGS. 3B and 3C. Breakdown of C3b in the diffusion chamber demonstrates that both glycosylated CR1a (3B) and non-glycosylated nCR1a (3C) were able to cross Bruch's membrane from the sample chamber and remain functionally active. CR1a and nCR1a from both chambers were found to act successfully as co-factors for FI to break down C3b into proteolytically-inactive C3b (iC3b) and further products, as demonstrated by the presence of bands representing C3b breakdown products iC3b and C3dg. Thus, CR1a and nCR1a are able to diffuse through BrM and retain the ability to confer C3b breakdown in the presence of Factor I.

Example 2

The expression levels of polypeptides according to the present invention are compared to assess if there is an optimal formulation, i.e. whether glycosylated polypeptides express at higher levels than non-glycosylated polypeptides. It is anticipated that the glycosylation state of the polypeptides will have a minimal effect on level of expression.

CR1a was found to be expressed well by human cells. nCR1a was found to be expressed at lower levels than CR1a but both polypeptides were found to be functionally active, see e.g. FIG. 2.

Example 3

The binding kinetics of purified polypeptides according to the present invention for C3b is tested using Surface Plasmon Resonance (SPR), whereby C3b is immobilised onto SPR chips and the polypeptides used in the fluid phase. The association and dissociation constants are directly measured and a kD value for the interaction inferred.

Whilst no differences are observed in the binding of the CR1a (CCPs 8-10) or CR1b (CCPs 15-17) species to C3b, glycosylated polypeptides bind more strongly to C3b than non-glycosylated polypeptides.

Binding Kinetics Measured by Bio-Layer Interferometry (BLI)

The affinity of CR1a for C3b protein was measured using OctetRed96 System (ForteBio, Pall Corp., USA). Biotinylated C3b protein was diluted in 0.2% PBST to final concentration of 0.4 µg/mL and loaded onto High Precision Streptavidin (SAX) Biosensors (ForteBio, Pall Corp., USA) for 600 s, previously hydrated with the same buffer for 20 min. C3b-loaded sensors were then washed with 0.2% PBST for 150 s (baseline) and dipped into wells containing CR1a in different concentrations ranging from 30.0 µg/mL to 2.6 µg/mL for 600 s (association) followed by wash with 0.2% PBST for 600 s (dissociation). Association and dissociation profiles were recorded and analysed with ForeBio Data Analysis v9 (ForteBio, Pall Corp., USA). The negative control i.e. 0.2% PBST containing well was used in parallel to subtract binding resulting from nonspecific interactions with the sensors. Experiments were performed using the kinetics mode, at 25° C. and sample plates were pre-agitated for 3 min. The binding profiles were globally fitted to 1:1 (one analyte in solution to one binding site on the surface). The KD was determined using data of the association (from 0 s to 600 s) and dissociation (from 0 s to 100 s) phases from four the lowest available analyte concentration by steady-state analysis. Binding affinities were also determined for native soluble C3b-binding complement regulators Factor H (FH) and FHL-1 to immobilised C3b.

Figure 5:
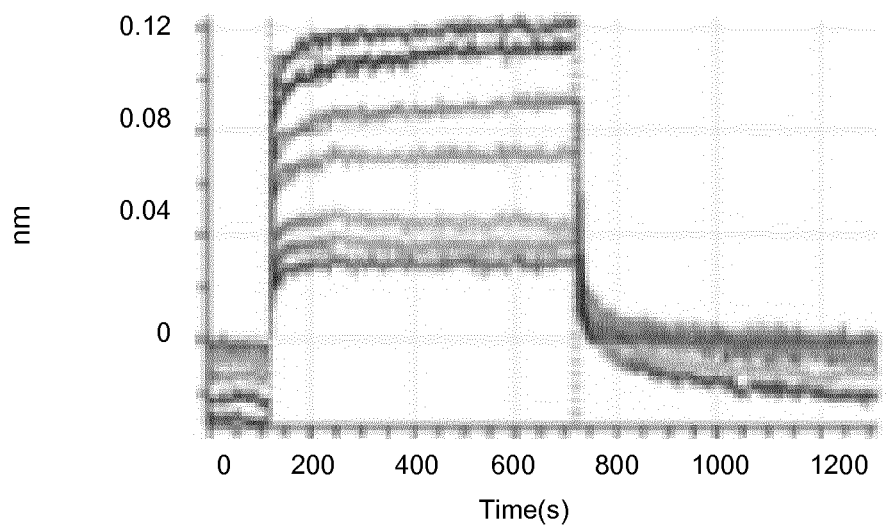
FIG. 5. Binding kinetics of CR1a, FH and FHL-1 for C3b measured by Biolayer interferometry (BLI).
Figure 5:
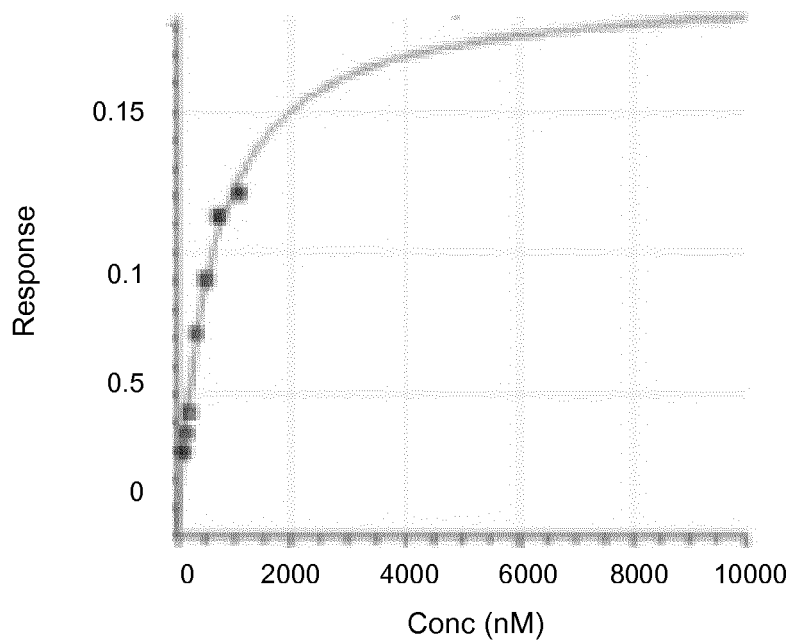
Figure 5:
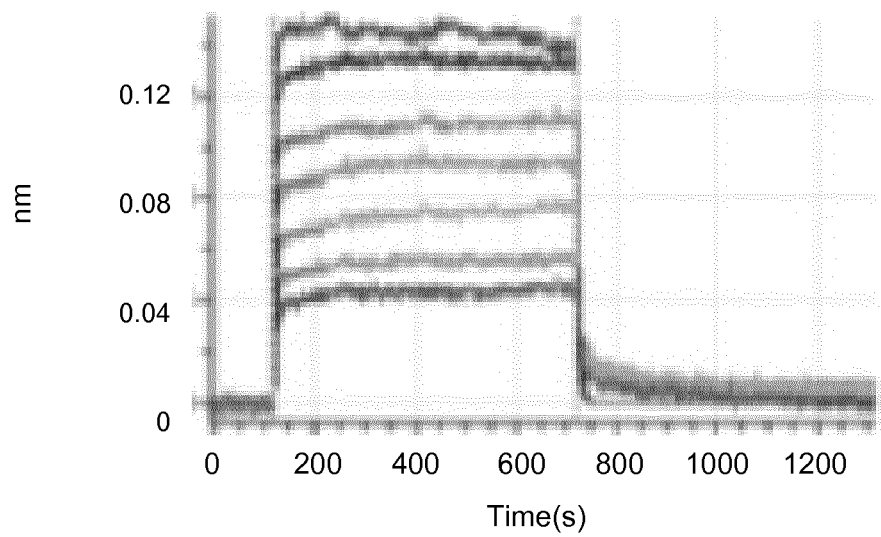
Figure 5:
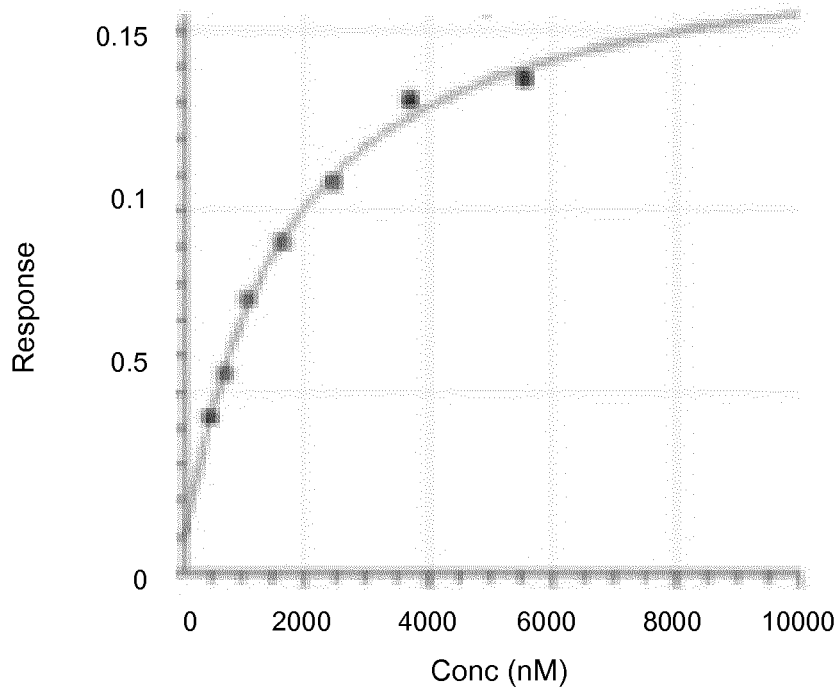
Figure 5:
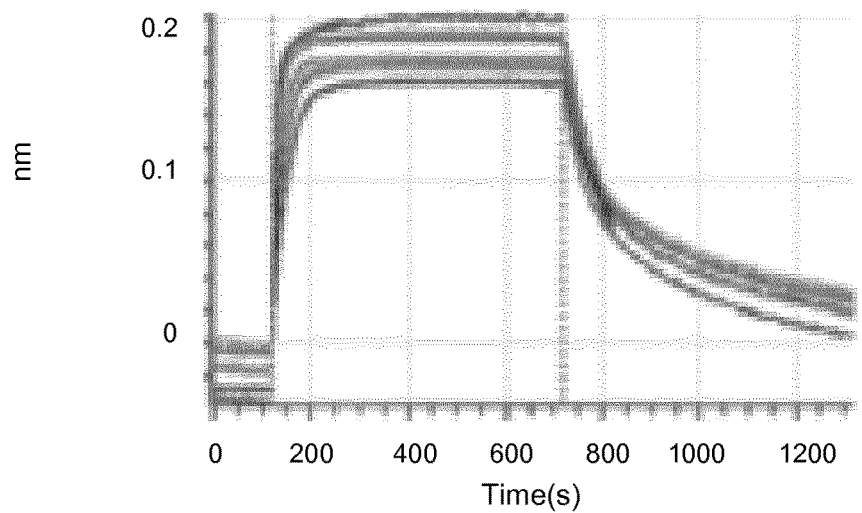
Figure 5:
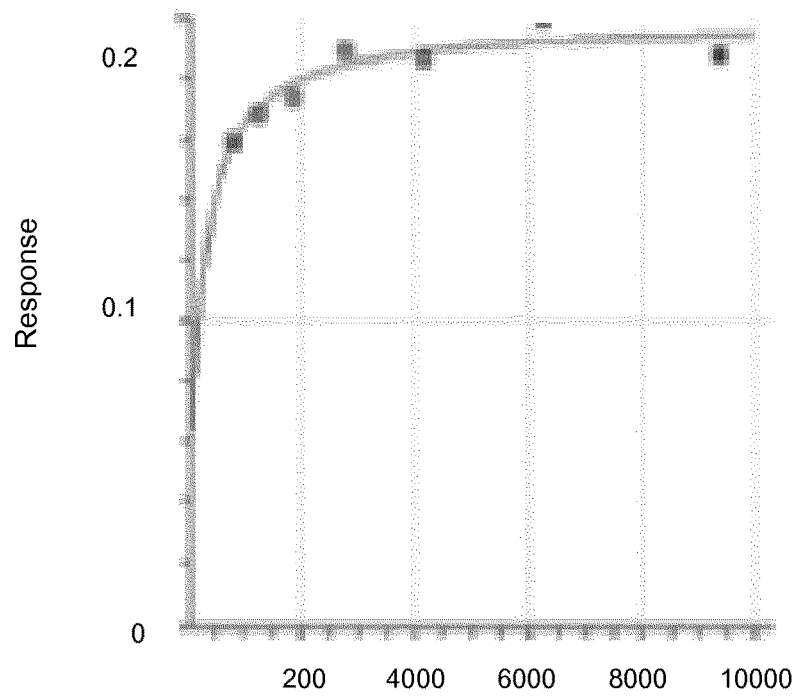

The results are shown in FIG. 5. The binding affinity of CR1a for C3b was found to be 21 nM. For comparison, the binding affinity for C3b of FH was 580 nM and of FHL-1 was 1.2 mM. CR1a therefore binds significantly more strongly to C3b than either native soluble complement regulator. The strong binding affinity of CR1a for C3b means that CR1a is a more effective agent to promote C3b break down than agents based on FH or FHL-1.

A strong binding affinity also enables CR1a to promote degradation of iC3b into desirable further downstream products e.g. C3dg (see FIG. 2). In contrast, FH and FHL-1 cannot cause degradation of C3b beyond iC3b. iC3b is a pro-inflammatory molecule which acts to recruit immune cells to the site of complement activation, which in turn cause negative inflammatory effects. Further breakdown of iC3b to C3dg by CR1a is thus advantageous and avoids further damage caused by the immune system.

Example 4

The diffusion rates of polypeptides according to the present invention are compared using Ussing chamber experiments (described above) to see if any differences arise due to the formulation of the protein.

Experiments include using Bruch's membranes derived from donors with AMD to determine whether the material deposited in the Bruch's membrane in this condition, including drusen and basal linear deposits, compromises the ability of the polypeptide to cross Bruch's membrane. It is anticipated that the optimal polypeptide will cross Bruch's membrane efficiently even in the presence of AMD changes.

Example 5

Nucleic acid according to the present invention, optionally encoding the preferred signal peptide, a polypeptide having at least 80% sequence identity to SEQ ID NO:4 and a termination codon, is inserted into an AAV vector. The resultant expression vector is used to transfect cultured RPE cells. The expression and secretion of the encoded polypeptide is evaluated. It is anticipated that the polypeptide having at least 80% sequence identity to SEQ ID NO:4 is secreted by the RPE cells and that the signal peptide has been cleaved from the secreted polypeptide.

Adeno-Associated Virus (AAV) Transduction

Nucleic acid encoding the CR1a polypeptide described in Example 1 was transfected into human APRE-19 cells (ATCC, USA) derived from retinal pigment epithelium.

AAV2 serotype viral particles were pre-packed with CR1a plasmid. ARPE-19 cells were seeded on six well cell culture plate (Corning) in 2 ml of DMEM/F12 growth medium (ATCC, USA) supplemented with 10% (v/v) fetal bovine serum (ATCC, USA) at the density of 300,000 cells per well. Cells were then left for incubation at 37° C. in humidified atmosphere of 5% $CO_2$ for 24 hrs. After incubation, cells were washed twice with 2 ml serum free DMEM/F12 growth medium. AAV2-CR1a at multiplicity of infection (MOI) 100,000 in serum free DMEM/F12 growth medium in total volume of 1 ml was added. AAV2-CR1a containing medium was incubated with cells for 24 hrs (37° C., 5% $CO_2$) followed by replacement with 2 ml of fresh serum free DMEM/F12 growth medium the next day. Control cells transduced with AAV-GFP were grown in parallel. Transduction efficiency was assessed 14 days post-infection. Secretion of CR1a by ARPE-19 cells was detected by dot blot: conditioned media from CR1a-transduced RPE cells was contacted with in-house polyclonal anti-CR1a antibody.

Figure 6:
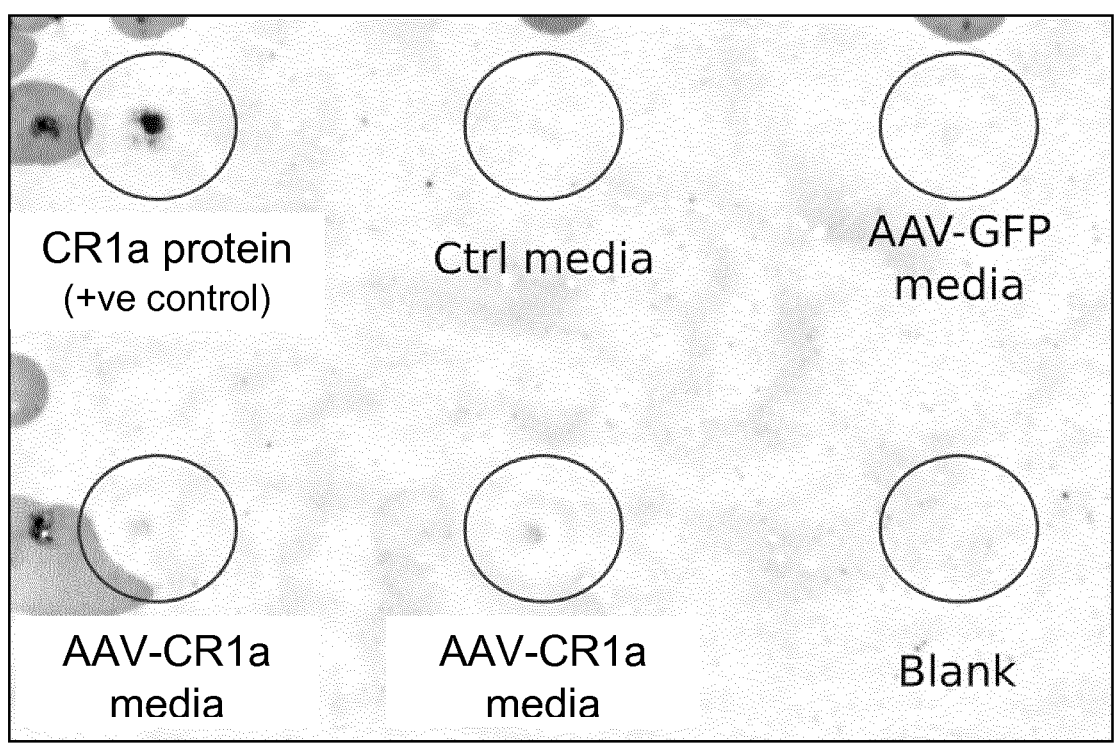
FIG. 6. Detection of secreted CR1a (AAV-CR1a media) from the tissue culture media of AAV-CR1a transduced ARPE-19 cells using anti-CR1a antibody. Recombinant CR1a protein was used as a positive control. Media alone and media from culture of AAV-GFP transduced ARPE-19 cells were used as negative controls.

The results are shown in FIG. 6. Immunoreactivity with the anti-CR1a antibody was seen in both samples tested (AAV-CR1a media), compared to media from RPE cells transduced with AAV-GFP (Ctrl media) used as a negative control. Purified recombinant CR1a protein was included as a positive control.

Recombinant CR1a polypeptides secreted from human APRE-19 and HEK293 cells were assessed for their ability to break down C3b to iC3b and C3dg.

Figure 7A:
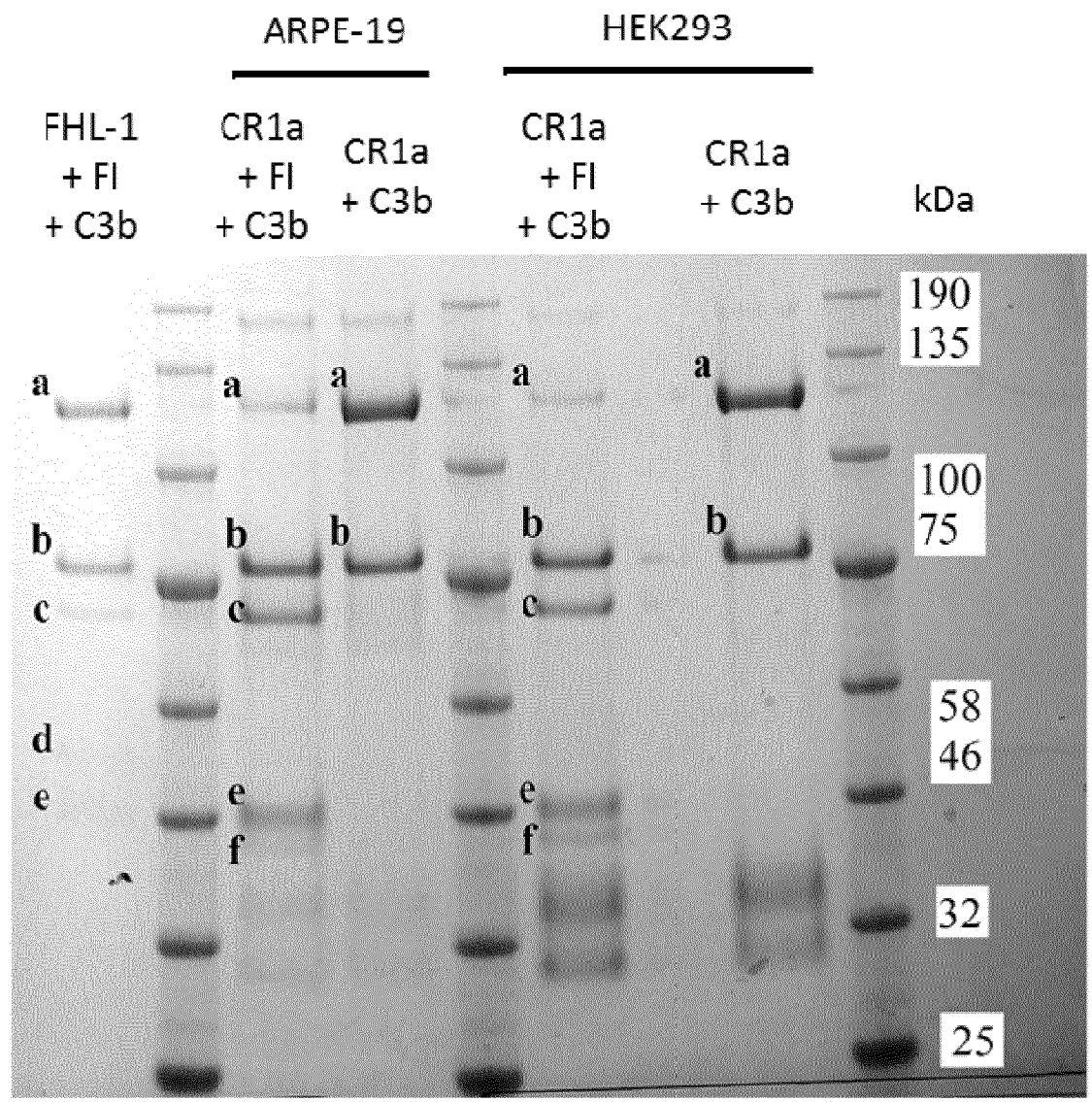
FIGS. 7A and 7B. Ability of secreted CR1a from human ARPE-19 cells to act as a cofactor for Factor I-mediated breakdown of C3b. (7A) Secreted CR1a acts as FI cofactor to produce iC3b (product e) and C3dg (product 0. CR1a secreted from human HEK293 cells was provided as a control. (7B) Cultured AAV-CR1a transduced RPE cells showed increased ability to break down C3b (product a) to iC3b (product b) compared to media containing non-transduced cells.

The results are shown in FIG. 7A. Functional CR1a polypeptide secreted from human APRE-19 cells was found to act as a cofactor for Factor I leading to breakdown of C3b into iC3b (product e) and C3dg (product 0. Reaction containing FHL-1+FI+C3b provided a MW control for C3b and product iC3b.

C3b break down was assessed in tissue culture media of human RPE cells (ARPE-19) transduced with AAV-delivered CR1a. AAV-GFP transduced RPE cells were used as a negative control. Transduced cells were supplemented with purified C3b and Factor 114 days after transduction. C3b and iC3b levels in tissue culture media were detected by Western blot.

Figure 7B:
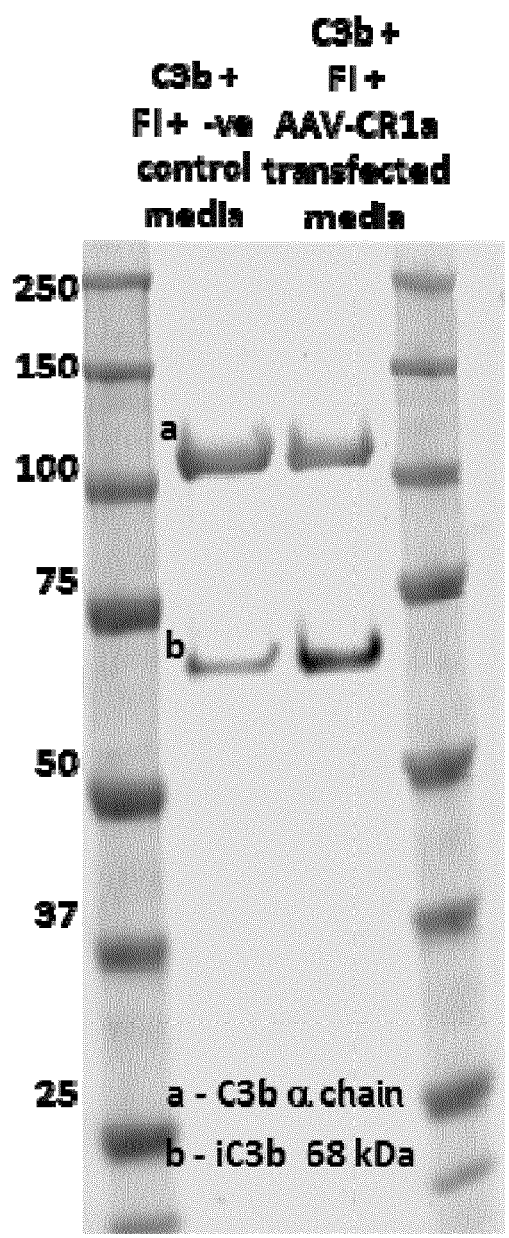

The results are shown in FIG. 7B. RPE cells produce their own complement components and were found to have a low native turnover of C3b (product a) into iC3b (product b; lane 2). However, RPE cells expressing AAV-delivered CR1a were found to have increased C3b breakdown capacity to iC3b (product b; lane 3) compared to the native turnover rate.

This indicates that CR1a is secreted successfully from eye cells, e.g. retinal pigment epithelium cells, is functionally active as a FI cofactor, enhances C3b break down to downstream products, is capable of complement regulation, and would provide therapeutic benefit for conditions involving over-activation of complement e.g. an excess of C3b.

Example 6

The polypeptides of the present invention find use in methods of treatment or prevention of complement-related disorders. One example of a complement related disorder is macular degeneration in the eye, e.g. AMD.

Figure 8:
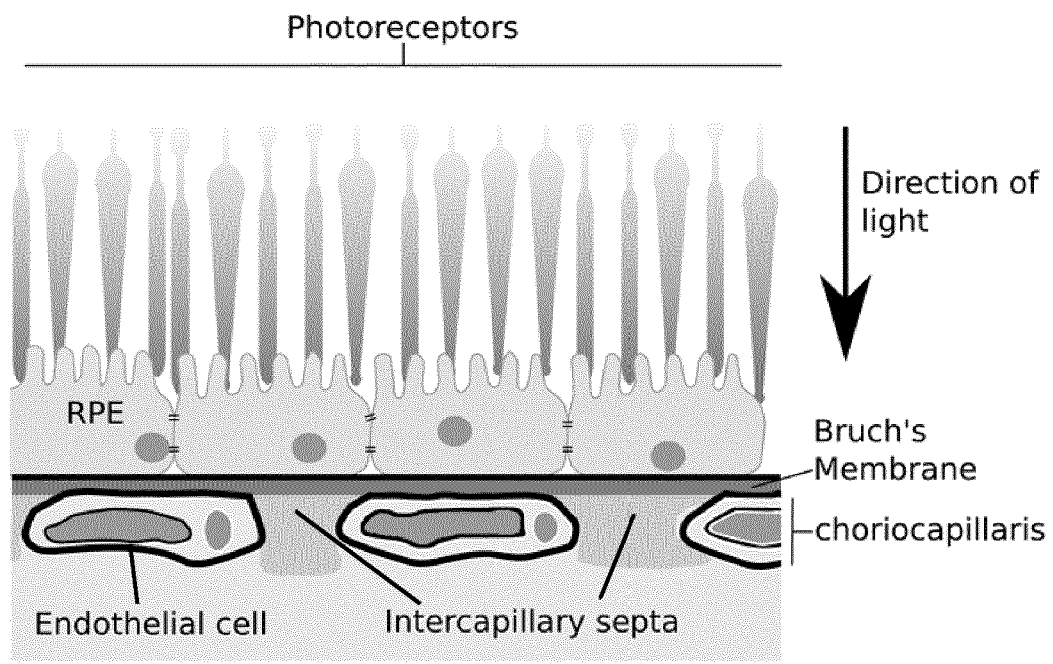
FIG. 8. Schematic of the macular region of the eye, showing photoreceptors, retinal pigment epithelium, Bruch's membrane, and the choriocapillaris and intercapillary septa in the choroid.

FIG. 8 provides a schematic of the eye macular region. The retinal pigment epithelium (RPE) is a continuous monolayer of cuboidal/columnar epithelial cells between the neurosensory retina and the vascular choroid. The cells have physical, optical, metabolic/biochemical and transport functions and play a critical role in the normal visual process. The RPE is separated from the choroid by Bruch's membrane (BrM): a thin (2-4 µm), acellular, five-layered, extracellular matrix. The BrM serves two major functions: the substratum of the RPE and a blood vessel wall. Immediately adjacent to the BrM, and within the choroid, is a layer of capillaries termed the choriocapillaris. Complement activation centres on the extracellular matrix of the choriocapillaris, termed the intercapillary septa.

The hallmark lesions of AMD, drusen, are formed from the accumulation of lipids and cellular debris, including many complement activation products. Drusen develop within the BrM adjacent to the RPE layer and disrupt the flow of nutrients from the choroid to the RPE, leading to cell dysfunction and death. The death of RPE cells also causes dysfunction of photoreceptor cells and subsequent loss of visual acuity.

Figure 9:
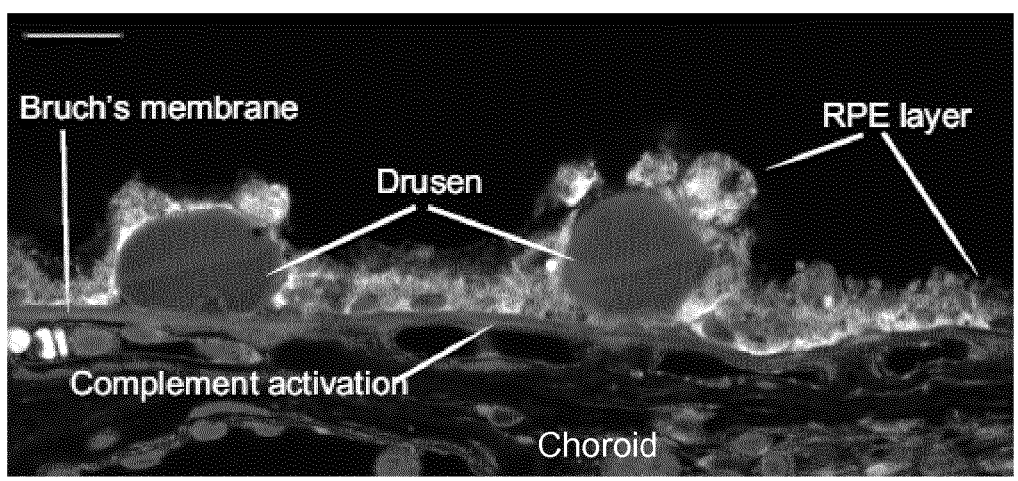
FIG. 9. Representative fluorescence microscopy image of retinal tissue from Forest et al. (2015) *Dis. Mod. Mech.* 8, 421-427 (FIG. 1). Shown are drusen deposits underlying degraded RPE cells and areas of complement activation. Scale bar 20 µm.

A representative fluorescence microscopy image of drusen deposits is provided in FIG. 9, taken from Forest et al. (2015) *Dis. Mod. Mech.* 8, 421-427 (FIG. 1). FIG. 9 shows retinal tissue from an 82-year-old female with AMD. A cell membrane marker shows degraded RPE cells overlying drusen. Areas of complement activation within the drusen and around the blood vessels are indicated by the terminal complement complex marker C5b-9. Nuclei are stained. Scale bar 20 μm.

Figure 10:
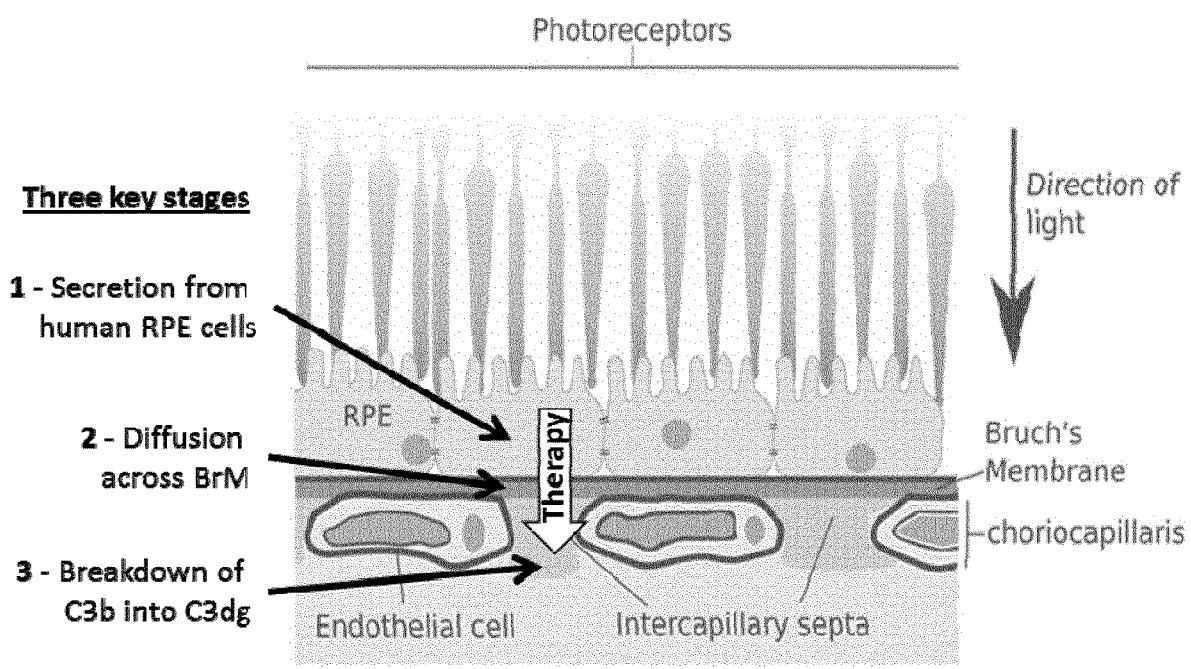
FIG. 10. Schematic of the macular region of the eye showing key stages of localised expression of effective complement therapeutic.
Figure 11:
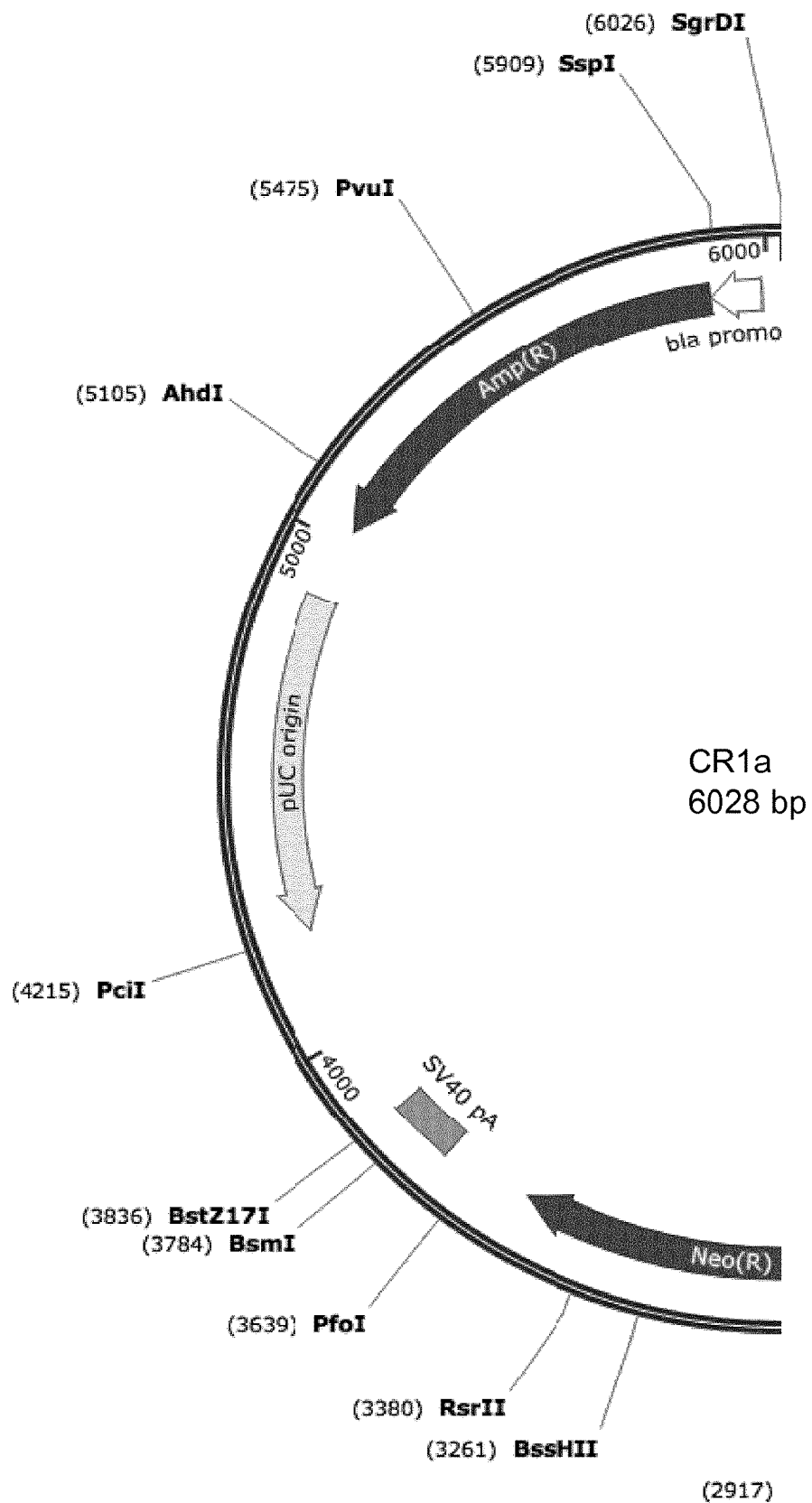
FIG. 11. Example of an expression vector comprising nucleic acid encoding a polypeptide according to the present invention (e.g. CR1a), promoter elements, replication elements and selection elements.
Figure 11:
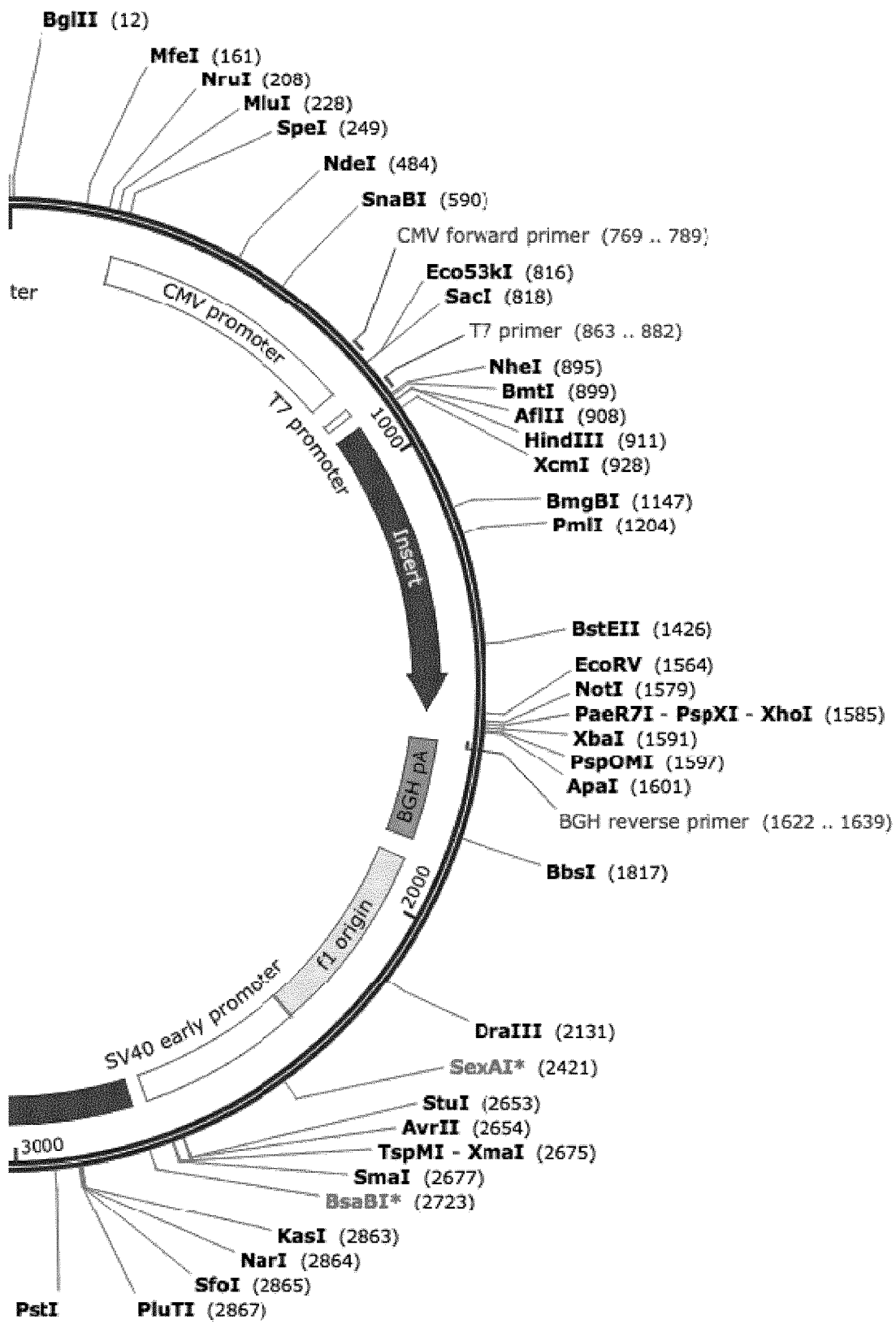

Systemic administration of a complement-regulating molecule would require a high dose and carries a substantial risk of detrimental off-target effects on functioning complement systems. Localised administration, e.g. expression from RPE cells, is a safer and more effective delivery method. However, for an RPE-expressed molecule to be effective in treating/preventing a complement-related disorder in the intercapillary septa of the choriocapillaris, i.e. the site of complement over-activation, the molecule will have to cross Bruch's membrane (see FIG. 10). That is, an effective complement-inhibiting therapy must meet the requirements of all three stages in FIG. 10.

As demonstrated herein, CR1a is:
1. Secreted from human RPE cells (see e.g. FIG. 6);
2. Able to passively diffuse across human BrM (see e.g. FIG. 3); and
3. Able to mediate the breakdown of C3b into iC3b, and further desirable break down products, in the presence of complement factor I (see e.g. FIGS. 2, 3, 7).

Therefore, CR1a is able to be expressed by RPE cells, is able to reach the areas of complement activation where C3b regulation is necessary, and can act as an effective therapeutic agent to treat complement over-activation in the eye, e.g. in AMD.

Example 7

Laser-Induced Choroidal Neovascularisation Model

This model applies laser burns to the retinas of mice or rats to induce choroidal neovascularization, for example as described in Schnabolk et al, Mol Ther Methods Clin Dev. 2018; 9: 1-11. The size of the choroidal neovascular complexes can be measured by fluorescein angiography or by histology.

Rodents are given a subretinal injection of AAV vector, e.g. AAV2, containing CR1a cDNA, or empty AAV vector as a control. Rodents receiving AAV vector containing CR1a cDNA secrete CR1a protein from their retinal pigment epithelial cells. When maximal CR1a protein excretion is achieved, laser burns are applied to the rodent retinas and the size of the choroidal neovascular complexes is measured at a pre-specified time after the laser burns. The complement inhibitory effect of CR1a polypeptide is found to decrease the size of the choroidal neovascular complexes compared to rodents administered the empty AAV vector.

Sodium Iodate Induced Retinal Degeneration

Mice are injected intravenously with sodium iodate which induces a degeneration of the retinal pigment epithelium that is partially dependent upon complement activation, for example as described in Katschke et al., *Sci Rep.* 2018; 8(1):7348. CR1a is delivered by intravitreal injection as a recombinant protein or by subretinal delivery using AAV vector, e.g. AAV2, containing CR1a cDNA. Empty AAV vector is administered as a control. CR1a treated mice are found to have less retinal degeneration than the control mice that did not receive CR1a treatment.

The invention claimed is:

1. A method of treating or reducing the likelihood of an ocular complement-related disease or condition, the method comprising administering a polypeptide which is capable of binding C3b, the polypeptide comprising an amino acid sequence wherein said amino acid sequence consists of a sequence having at least 85% identity to SEQ ID NO:4 and wherein the polypeptide has a total length of 450 amino acids or fewer.

2. A method according to claim 1, wherein the treatment or reduction of the likelihood of an ocular disease or condition comprises modifying at least one ocular cell of a subject to express or comprise the polypeptide.

3. A method according to claim 1, wherein the treatment or reduction of the likelihood of an ocular disease or condition comprises modifying at least one ocular cell of a subject to express or comprise a nucleic acid encoding the polypeptide.

4. A method according to claim 1, wherein the treatment or reduction of the likelihood of an ocular disease or condition comprises administering a vector comprising a nucleic acid encoding the polypeptide to at least one ocular cell of a subject.

5. A method according to claim 2, wherein the at least one ocular cell is a retinal pigment epithelial (RPE) cell.

6. A method according to claim 1, wherein the disease or condition is a disease or condition in which C3b or a C3b-containing complex, an activity/response associated with C3b or a C3b-containing complex, or a product of an activity/response associated with C3b or a C3b-containing complex is pathologically implicated.

7. A method according to claim 1, wherein the disease or condition is selected from one or more of: macular degeneration, age-related macular degeneration (AMD), early AMD, intermediate AMD, late AMD, geographic atrophy (dry' AMD), 'wet' (neovascular) AMD, choroidal neovascularisation (CNV), glaucoma, autoimmune uveitis, diabetic retinopathy, and early-onset macular degeneration (EOMD).

8. A method according to claim 1, wherein the polypeptide comprises an amino acid sequence that consists of a sequence having at least 95% identity to SEQ ID NO:4.

9. A method according to claim 1, wherein Xaa at position 111 of SEQ ID NO:4 is A or T, Xaa at position 157 of SEQ ID NO:4 is P or L, and/or Xaa at position 160 of SEQ ID NO:4 is G or R.

10. A method according to claim 1, wherein the polypeptide has a total length of 50 to 250 amino acids.

11. A method according to claim 1, wherein the polypeptide comprises, or consists of, SEQ ID NO:2, SEQ ID NO:3 or SEQ ID NO:13.

12. A method according to claim 1, wherein the polypeptide is capable of acting as a co-factor for Complement Factor I.

13. A method according to claim 1, wherein the polypeptide is capable of being expressed functionally by RPE cells and/or is capable of diffusing across Bruch's membrane (BrM).

14. A method according to claim 1, wherein the polypeptide binds to C3b in the region bound by a co-factor for Complement Factor I, or wherein the polypeptide binds to C3b in the region bound by Complement Receptor 1 (CR1).

15. A method according to claim 1, wherein the polypeptide comprises a secretory pathway sequence.

16. A method according to claim 15, wherein the secretory pathway sequence comprises, or consists of, SEQ ID NO:7, or wherein the polypeptide comprises, or consists of, SEQ ID NO:47, 49, or 51.

17. A method according to claim 15, wherein the polypeptide comprises a cleavage site for removing the secretory pathway sequence.

18. A method according to claim 1, wherein the treatment or reduction of the likelihood comprises administering a nucleic acid encoding the polypeptide.

19. A method according to claim 18, wherein the nucleic acid encodes a polypeptide comprising or consisting of SEQ ID NO:2.

20. A method according to claim 18, wherein the nucleic acid comprises a sequence having at least 95% sequence identity to SEQ ID NO:35.

21. A method according to claim 4, wherein the vector is a viral vector.

22. A method according to claim 21, wherein the vector is a lentiviral vector, a retroviral vector, an adenoviral vector, an adeno-associated viral (AAV) vector, a vaccinia virus vector, or a herpesvirus vector.

23. A method according to claim 1, wherein the polypeptide is functional on the RPE side of Bruch's membrane and in the choroid and/or choriocapillaris.

* * * * *

SEQUENCE LISTING

```
<160> NUMBER OF SEQ ID NOS: 54

<210> SEQ ID NO 1
<211> LENGTH: 2039
<212> TYPE: PRT
<213> ORGANISM: Homo sapiens

<400> SEQUENCE: 1

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
```

```
            130                 135                 140
Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
                180                 185                 190

Tyr Arg Cys Asn Pro Gly Ser Gly Arg Lys Val Phe Glu Leu Val
                195                 200                 205

Gly Glu Pro Ser Ile Tyr Cys Thr Ser Asn Asp Asp Gln Val Gly Ile
                210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asn Arg Ser Leu Phe
                245                 250                 255

Ser Leu Asn Glu Val Val Glu Phe Arg Cys Gln Pro Gly Phe Val Met
                260                 265                 270

Lys Gly Pro Arg Arg Val Lys Cys Gln Ala Leu Asn Lys Trp Glu Pro
                275                 280                 285

Glu Leu Pro Ser Cys Ser Arg Val Cys Gln Pro Pro Asp Val Leu
                290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
                340                 345                 350

Cys Glu Val Lys Ser Cys Asp Asp Phe Met Gly Gln Leu Leu Asn Gly
                355                 360                 365

Arg Val Leu Phe Pro Val Asn Leu Gln Leu Gly Ala Lys Val Asp Phe
                370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Pro Val Ile Pro Asn Gly Arg His
                420                 425                 430

Thr Gly Lys Pro Leu Glu Val Phe Pro Phe Gly Lys Thr Val Asn Tyr
                435                 440                 445

Thr Cys Asp Pro His Pro Asp Arg Gly Thr Ser Phe Asp Leu Ile Gly
                450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
                500                 505                 510

Phe Pro Ile Gly Thr Ser Leu Lys Tyr Glu Cys Arg Pro Glu Tyr Tyr
                515                 520                 525

Gly Arg Pro Phe Ser Ile Thr Cys Leu Asp Asn Leu Val Trp Ser Ser
                530                 535                 540

Pro Lys Asp Val Cys Lys Arg Lys Ser Cys Lys Thr Pro Pro Asp Pro
545                 550                 555                 560
```

-continued

```
Val Asn Gly Met Val His Val Ile Thr Asp Ile Gln Val Gly Ser Arg
            565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
            595                 600                 605

Pro Ile Cys Gln Arg Ile Pro Cys Gly Leu Pro Pro Thr Ile Ala Asn
            610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Arg Lys Val Phe Glu
            645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
            675                 680                 685

Thr Pro Pro Asn Val Glu Asn Gly Ile Leu Val Ser Asp Asn Arg Ser
            690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
            725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
            755                 760                 765

Gly Gln Glu Val Phe Tyr Ser Cys Glu Pro Gly Tyr Asp Leu Arg Gly
            770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
            805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
            835                 840                 845

Tyr Cys Val Leu Ala Gly Met Glu Ser Leu Trp Asn Ser Ser Val Pro
850                 855                 860

Val Cys Glu Gln Ile Phe Cys Pro Ser Pro Val Ile Pro Asn Gly
865                 870                 875                 880

Arg His Thr Gly Lys Pro Leu Glu Val Phe Pro Phe Gly Lys Ala Val
            885                 890                 895

Asn Tyr Thr Cys Asp Pro His Pro Asp Arg Gly Thr Ser Phe Asp Leu
            900                 905                 910

Ile Gly Glu Ser Thr Ile Arg Cys Thr Ser Asp Pro Gln Gly Asn Gly
            915                 920                 925

Val Trp Ser Ser Pro Ala Pro Arg Cys Gly Ile Leu Gly His Cys Gln
            930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
            965                 970                 975
```

```
            Tyr Tyr Gly Arg Pro Phe Ser Ile Thr Cys Leu Asp Asn Leu Val Trp
                            980                 985                 990

Ser Ser Pro Lys Asp Val Cys Lys Arg Lys Ser Cys Lys Thr Pro Pro
                    995                 1000                1005

Asp Pro Val Asn Gly Met Val His Val Ile Thr Asp Ile Gln Val
                1010                1015                1020

Gly Ser Arg Ile Asn Tyr Ser Cys Thr Thr Gly His Arg Leu Ile
                1025                1030                1035

Gly His Ser Ser Ala Glu Cys Ile Leu Ser Gly Asn Thr Ala His
                1040                1045                1050

Trp Ser Thr Lys Pro Pro Ile Cys Gln Arg Ile Pro Cys Gly Leu
                1055                1060                1065

Pro Pro Thr Ile Ala Asn Gly Asp Phe Ile Ser Thr Asn Arg Glu
                1070                1075                1080

Asn Phe His Tyr Gly Ser Val Val Thr Tyr Arg Cys Asn Leu Gly
                1085                1090                1095

Ser Arg Gly Arg Lys Val Phe Glu Leu Val Gly Glu Pro Ser Ile
                1100                1105                1110

Tyr Cys Thr Ser Asn Asp Asp Gln Val Gly Ile Trp Ser Gly Pro
                1115                1120                1125

Ala Pro Gln Cys Ile Ile Pro Asn Lys Cys Thr Pro Pro Asn Val
                1130                1135                1140

Glu Asn Gly Ile Leu Val Ser Asp Asn Arg Ser Leu Phe Ser Leu
                1145                1150                1155

Asn Glu Val Val Glu Phe Arg Cys Gln Pro Gly Phe Val Met Lys
                1160                1165                1170

Gly Pro Arg Arg Val Lys Cys Gln Ala Leu Asn Lys Trp Glu Pro
                1175                1180                1185

Glu Leu Pro Ser Cys Ser Arg Val Cys Gln Pro Pro Pro Glu Ile
                1190                1195                1200

Leu His Gly Glu His Thr Pro Ser His Gln Asp Asn Phe Ser Pro
                1205                1210                1215

Gly Gln Glu Val Phe Tyr Ser Cys Glu Pro Gly Tyr Asp Leu Arg
                1220                1225                1230

Gly Ala Ala Ser Leu His Cys Thr Pro Gln Gly Asp Trp Ser Pro
                1235                1240                1245

Glu Ala Pro Arg Cys Ala Val Lys Ser Cys Asp Asp Phe Leu Gly
                1250                1255                1260

Gln Leu Pro His Gly Arg Val Leu Phe Pro Leu Asn Leu Gln Leu
                1265                1270                1275

Gly Ala Lys Val Ser Phe Val Cys Asp Glu Gly Phe Arg Leu Lys
                1280                1285                1290

Gly Ser Ser Val Ser His Cys Val Leu Val Gly Met Arg Ser Leu
                1295                1300                1305

Trp Asn Asn Ser Val Pro Val Cys Glu His Ile Phe Cys Pro Asn
                1310                1315                1320

Pro Pro Ala Ile Leu Asn Gly Arg His Thr Gly Thr Pro Ser Gly
                1325                1330                1335

Asp Ile Pro Tyr Gly Lys Glu Ile Ser Tyr Thr Cys Asp Pro His
                1340                1345                1350

Pro Asp Arg Gly Met Thr Phe Asn Leu Ile Gly Glu Ser Thr Ile
                1355                1360                1365

Arg Cys Thr Ser Asp Pro His Gly Asn Gly Val Trp Ser Ser Pro
```

```
            1370                1375                1380

Ala Pro Arg Cys Glu Leu Ser  Val Arg Ala Gly His  Cys Lys Thr
    1385                1390                1395

Pro Glu Gln Phe Pro Phe Ala  Ser Pro Thr Ile Pro  Ile Asn Asp
    1400                1405                1410

Phe Glu Phe Pro Val Gly Thr  Ser Leu Asn Tyr Glu  Cys Arg Pro
    1415                1420                1425

Gly Tyr Phe Gly Lys Met Phe  Ser Ile Ser Cys Leu  Glu Asn Leu
    1430                1435                1440

Val Trp Ser Ser Val Glu Asp  Asn Cys Arg Arg Lys  Ser Cys Gly
    1445                1450                1455

Pro Pro Pro Glu Pro Phe Asn  Gly Met Val His Ile  Asn Thr Asp
    1460                1465                1470

Thr Gln Phe Gly Ser Thr Val  Asn Tyr Ser Cys Asn  Glu Gly Phe
    1475                1480                1485

Arg Leu Ile Gly Ser Pro Ser  Thr Thr Cys Leu Val  Ser Gly Asn
    1490                1495                1500

Asn Val Thr Trp Asp Lys Lys  Ala Pro Ile Cys Glu  Ile Ile Ser
    1505                1510                1515

Cys Glu Pro Pro Pro Thr Ile  Ser Asn Gly Asp Phe  Tyr Ser Asn
    1520                1525                1530

Asn Arg Thr Ser Phe His Asn  Gly Thr Val Val Thr  Tyr Gln Cys
    1535                1540                1545

His Thr Gly Pro Asp Gly Glu  Gln Leu Phe Glu Leu  Val Gly Glu
    1550                1555                1560

Arg Ser Ile Tyr Cys Thr Ser  Lys Asp Asp Gln Val  Gly Val Trp
    1565                1570                1575

Ser Ser Pro Pro Pro Arg Cys  Ile Ser Thr Asn Lys  Cys Thr Ala
    1580                1585                1590

Pro Glu Val Glu Asn Ala Ile  Arg Val Pro Gly Asn  Arg Ser Phe
    1595                1600                1605

Phe Ser Leu Thr Glu Ile Ile  Arg Phe Arg Cys Gln  Pro Gly Phe
    1610                1615                1620

Val Met Val Gly Ser His Thr  Val Gln Cys Gln Thr  Asn Gly Arg
    1625                1630                1635

Trp Gly Pro Lys Leu Pro His  Cys Ser Arg Val Cys  Gln Pro Pro
    1640                1645                1650

Pro Glu Ile Leu His Gly Glu  His Thr Leu Ser His  Gln Asp Asn
    1655                1660                1665

Phe Ser Pro Gly Gln Glu Val  Phe Tyr Ser Cys Glu  Pro Ser Tyr
    1670                1675                1680

Asp Leu Arg Gly Ala Ala Ser  Leu His Cys Thr Pro  Gln Gly Asp
    1685                1690                1695

Trp Ser Pro Glu Ala Pro Arg  Cys Thr Val Lys Ser  Cys Asp Asp
    1700                1705                1710

Phe Leu Gly Gln Leu Pro His  Gly Arg Val Leu Leu  Pro Leu Asn
    1715                1720                1725

Leu Gln Leu Gly Ala Lys Val  Ser Phe Val Cys Asp  Glu Gly Phe
    1730                1735                1740

Arg Leu Lys Gly Arg Ser Ala  Ser His Cys Val Leu  Ala Gly Met
    1745                1750                1755

Lys Ala Leu Trp Asn Ser Ser  Val Pro Val Cys Glu  Gln Ile Phe
    1760                1765                1770
```

Cys Pro Asn Pro Pro Ala Ile Leu Asn Gly Arg His Thr Gly Thr
    1775                1780                1785

Pro Phe Gly Asp Ile Pro Tyr Gly Lys Glu Ile Ser Tyr Ala Cys
    1790                1795                1800

Asp Thr His Pro Asp Arg Gly Met Thr Phe Asn Leu Ile Gly Glu
    1805                1810                1815

Ser Ser Ile Arg Cys Thr Ser Asp Pro Gln Gly Asn Gly Val Trp
    1820                1825                1830

Ser Ser Pro Ala Pro Arg Cys Glu Leu Ser Val Pro Ala Ala Cys
    1835                1840                1845

Pro His Pro Pro Lys Ile Gln Asn Gly His Tyr Ile Gly Gly His
    1850                1855                1860

Val Ser Leu Tyr Leu Pro Gly Met Thr Ile Ser Tyr Ile Cys Asp
    1865                1870                1875

Pro Gly Tyr Leu Leu Val Gly Lys Gly Phe Ile Phe Cys Thr Asp
    1880                1885                1890

Gln Gly Ile Trp Ser Gln Leu Asp His Tyr Cys Lys Glu Val Asn
    1895                1900                1905

Cys Ser Phe Pro Leu Phe Met Asn Gly Ile Ser Lys Glu Leu Glu
    1910                1915                1920

Met Lys Lys Val Tyr His Tyr Gly Asp Tyr Val Thr Leu Lys Cys
    1925                1930                1935

Glu Asp Gly Tyr Thr Leu Glu Gly Ser Pro Trp Ser Gln Cys Gln
    1940                1945                1950

Ala Asp Asp Arg Trp Asp Pro Pro Leu Ala Lys Cys Thr Ser Arg
    1955                1960                1965

Thr His Asp Ala Leu Ile Val Gly Thr Leu Ser Gly Thr Ile Phe
    1970                1975                1980

Phe Ile Leu Leu Ile Ile Phe Leu Ser Trp Ile Ile Leu Lys His
    1985                1990                1995

Arg Lys Gly Asn Asn Ala His Glu Asn Pro Lys Glu Val Ala Ile
    2000                2005                2010

His Leu His Ser Gln Gly Gly Ser Ser Val His Pro Arg Thr Leu
    2015                2020                2025

Gln Thr Asn Glu Glu Asn Ser Arg Val Leu Pro
    2030                2035

<210> SEQ ID NO 2
<211> LENGTH: 194
<212> TYPE: PRT
<213> ORGANISM: Homo sapiens

<400> SEQUENCE: 2

Gly His Cys Gln Ala Pro Asp His Phe Leu Phe Ala Lys Leu Lys Thr
1               5                   10                  15

Gln Thr Asn Ala Ser Asp Phe Pro Ile Gly Thr Ser Leu Lys Tyr Glu
                20                  25                  30

Cys Arg Pro Glu Tyr Tyr Gly Arg Pro Phe Ser Ile Thr Cys Leu Asp
            35                  40                  45

Asn Leu Val Trp Ser Ser Pro Lys Asp Val Cys Lys Arg Lys Ser Cys
        50                  55                  60

Lys Thr Pro Pro Asp Pro Val Asn Gly Met Val His Val Ile Thr Asp
65                  70                  75                  80

Ile Gln Val Gly Ser Arg Ile Asn Tyr Ser Cys Thr Thr Gly His Arg

```
                85                  90                  95
Leu Ile Gly His Ser Ser Ala Glu Cys Ile Leu Ser Gly Asn Ala Ala
            100                 105                 110
His Trp Ser Thr Lys Pro Pro Ile Cys Gln Arg Ile Pro Cys Gly Leu
            115                 120                 125
Pro Pro Thr Ile Ala Asn Gly Asp Phe Ile Ser Thr Asn Arg Glu Asn
130                 135                 140
Phe His Tyr Gly Ser Val Val Thr Tyr Arg Cys Asn Pro Gly Ser Gly
145                 150                 155                 160
Gly Arg Lys Val Phe Glu Leu Val Gly Glu Pro Ser Ile Tyr Cys Thr
                165                 170                 175
Ser Asn Asp Asp Gln Val Gly Ile Trp Ser Gly Pro Ala Pro Gln Cys
            180                 185                 190
Ile Ile

<210> SEQ ID NO 3
<211> LENGTH: 194
<212> TYPE: PRT
<213> ORGANISM: Homo sapiens

<400> SEQUENCE: 3

Gly His Cys Gln Ala Pro Asp His Phe Leu Phe Ala Lys Leu Lys Thr
1               5                   10                  15
Gln Thr Asn Ala Ser Asp Phe Pro Ile Gly Thr Ser Leu Lys Tyr Glu
            20                  25                  30
Cys Arg Pro Glu Tyr Tyr Gly Arg Pro Phe Ser Ile Thr Cys Leu Asp
        35                  40                  45
Asn Leu Val Trp Ser Ser Pro Lys Asp Val Cys Lys Arg Lys Ser Cys
    50                  55                  60
Lys Thr Pro Pro Asp Pro Val Asn Gly Met Val His Val Ile Thr Asp
65                  70                  75                  80
Ile Gln Val Gly Ser Arg Ile Asn Tyr Ser Cys Thr Thr Gly His Arg
                85                  90                  95
Leu Ile Gly His Ser Ser Ala Glu Cys Ile Leu Ser Gly Asn Thr Ala
            100                 105                 110
His Trp Ser Thr Lys Pro Pro Ile Cys Gln Arg Ile Pro Cys Gly Leu
            115                 120                 125
Pro Pro Thr Ile Ala Asn Gly Asp Phe Ile Ser Thr Asn Arg Glu Asn
130                 135                 140
Phe His Tyr Gly Ser Val Val Thr Tyr Arg Cys Asn Leu Gly Ser Arg
145                 150                 155                 160
Gly Arg Lys Val Phe Glu Leu Val Gly Glu Pro Ser Ile Tyr Cys Thr
                165                 170                 175
Ser Asn Asp Asp Gln Val Gly Ile Trp Ser Gly Pro Ala Pro Gln Cys
            180                 185                 190
Ile Ile

<210> SEQ ID NO 4
<211> LENGTH: 194
<212> TYPE: PRT
<213> ORGANISM: Homo sapiens
<220> FEATURE:
<221> NAME/KEY: MISC_FEATURE
<222> LOCATION: (111)..(111)
<223> OTHER INFORMATION: X = A or T
<220> FEATURE:
<221> NAME/KEY: MISC_FEATURE
```

```
<222> LOCATION: (157)..(157)
<223> OTHER INFORMATION: X = P or L
<220> FEATURE:
<221> NAME/KEY: MISC_FEATURE
<222> LOCATION: (160)..(160)
<223> OTHER INFORMATION: X = G or R

<400> SEQUENCE: 4
```

| Gly | His | Cys | Gln | Ala | Pro | Asp | His | Phe | Leu | Phe | Ala | Lys | Leu | Lys | Thr |
|---|---|---|---|---|---|---|---|---|---|---|---|---|---|---|---|
| 1 | | | | 5 | | | | | 10 | | | | | 15 | |

| Gln | Thr | Asn | Ala | Ser | Asp | Phe | Pro | Ile | Gly | Thr | Ser | Leu | Lys | Tyr | Glu |
|---|---|---|---|---|---|---|---|---|---|---|---|---|---|---|---|
| | | | 20 | | | | | 25 | | | | | 30 | | |

| Cys | Arg | Pro | Glu | Tyr | Tyr | Gly | Arg | Pro | Phe | Ser | Ile | Thr | Cys | Leu | Asp |
|---|---|---|---|---|---|---|---|---|---|---|---|---|---|---|---|
| | | 35 | | | | | 40 | | | | | 45 | | | |

| Asn | Leu | Val | Trp | Ser | Ser | Pro | Lys | Asp | Val | Cys | Lys | Arg | Lys | Ser | Cys |
|---|---|---|---|---|---|---|---|---|---|---|---|---|---|---|---|
| 50 | | | | | 55 | | | | | 60 | | | | | |

| Lys | Thr | Pro | Pro | Asp | Pro | Val | Asn | Gly | Met | Val | His | Val | Ile | Thr | Asp |
|---|---|---|---|---|---|---|---|---|---|---|---|---|---|---|---|
| 65 | | | | 70 | | | | | 75 | | | | | 80 | |

| Ile | Gln | Val | Gly | Ser | Arg | Ile | Asn | Tyr | Ser | Cys | Thr | Thr | Gly | His | Arg |
|---|---|---|---|---|---|---|---|---|---|---|---|---|---|---|---|
| | | | | 85 | | | | | 90 | | | | | 95 | |

| Leu | Ile | Gly | His | Ser | Ser | Ala | Glu | Cys | Ile | Leu | Ser | Gly | Asn | Xaa | Ala |
|---|---|---|---|---|---|---|---|---|---|---|---|---|---|---|---|
| | | | 100 | | | | | 105 | | | | | 110 | | |

| His | Trp | Ser | Thr | Lys | Pro | Pro | Ile | Cys | Gln | Arg | Ile | Pro | Cys | Gly | Leu |
|---|---|---|---|---|---|---|---|---|---|---|---|---|---|---|---|
| | | 115 | | | | | 120 | | | | | 125 | | | |

| Pro | Pro | Thr | Ile | Ala | Asn | Gly | Asp | Phe | Ile | Ser | Thr | Asn | Arg | Glu | Asn |
|---|---|---|---|---|---|---|---|---|---|---|---|---|---|---|---|
| 130 | | | | | 135 | | | | | 140 | | | | | |

| Phe | His | Tyr | Gly | Ser | Val | Val | Thr | Tyr | Arg | Cys | Asn | Xaa | Gly | Ser | Xaa |
|---|---|---|---|---|---|---|---|---|---|---|---|---|---|---|---|
| 145 | | | | 150 | | | | | 155 | | | | | 160 | |

| Gly | Arg | Lys | Val | Phe | Glu | Leu | Val | Gly | Glu | Pro | Ser | Ile | Tyr | Cys | Thr |
|---|---|---|---|---|---|---|---|---|---|---|---|---|---|---|---|
| | | | | 165 | | | | | 170 | | | | | 175 | |

| Ser | Asn | Asp | Asp | Gln | Val | Gly | Ile | Trp | Ser | Gly | Pro | Ala | Pro | Gln | Cys |
|---|---|---|---|---|---|---|---|---|---|---|---|---|---|---|---|
| | | | 180 | | | | | 185 | | | | | 190 | | |

| Ile | Ile |
|---|---|
| | |

```
<210> SEQ ID NO 5
<211> LENGTH: 194
<212> TYPE: PRT
<213> ORGANISM: Homo sapiens

<400> SEQUENCE: 5
```

| Gly | His | Cys | Gln | Ala | Pro | Asp | His | Phe | Leu | Phe | Ala | Lys | Leu | Lys | Thr |
|---|---|---|---|---|---|---|---|---|---|---|---|---|---|---|---|
| 1 | | | | 5 | | | | | 10 | | | | | 15 | |

| Gln | Thr | Gln | Ala | Ser | Asp | Phe | Pro | Ile | Gly | Thr | Ser | Leu | Lys | Tyr | Glu |
|---|---|---|---|---|---|---|---|---|---|---|---|---|---|---|---|
| | | | 20 | | | | | 25 | | | | | 30 | | |

| Cys | Arg | Pro | Glu | Tyr | Tyr | Gly | Arg | Pro | Phe | Ser | Ile | Thr | Cys | Leu | Asp |
|---|---|---|---|---|---|---|---|---|---|---|---|---|---|---|---|
| | | 35 | | | | | 40 | | | | | 45 | | | |

| Asn | Leu | Val | Trp | Ser | Ser | Pro | Lys | Asp | Val | Cys | Lys | Arg | Lys | Ser | Cys |
|---|---|---|---|---|---|---|---|---|---|---|---|---|---|---|---|
| 50 | | | | | 55 | | | | | 60 | | | | | |

| Lys | Thr | Pro | Pro | Asp | Pro | Val | Asn | Gly | Met | Val | His | Val | Ile | Thr | Asp |
|---|---|---|---|---|---|---|---|---|---|---|---|---|---|---|---|
| 65 | | | | 70 | | | | | 75 | | | | | 80 | |

| Ile | Gln | Val | Gly | Ser | Arg | Ile | Gln | Tyr | Ser | Cys | Thr | Thr | Gly | His | Arg |
|---|---|---|---|---|---|---|---|---|---|---|---|---|---|---|---|
| | | | | 85 | | | | | 90 | | | | | 95 | |

| Leu | Ile | Gly | His | Ser | Ser | Ala | Glu | Cys | Ile | Leu | Ser | Gly | Asn | Ala | Ala |
|---|---|---|---|---|---|---|---|---|---|---|---|---|---|---|---|
| | | | 100 | | | | | 105 | | | | | 110 | | |

| His | Trp | Ser | Thr | Lys | Pro | Pro | Ile | Cys | Gln | Arg | Ile | Pro | Cys | Gly | Leu |
|---|---|---|---|---|---|---|---|---|---|---|---|---|---|---|---|
| | | 115 | | | | | 120 | | | | | 125 | | | |

```
Pro Pro Thr Ile Ala Asn Gly Asp Phe Ile Ser Thr Asn Arg Glu Asn
    130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
                180                 185                 190

Ile Ile

<210> SEQ ID NO 6
<211> LENGTH: 194
<212> TYPE: PRT
<213> ORGANISM: Homo sapiens

<400> SEQUENCE: 6

Gly His Cys Gln Ala Pro Asp His Phe Leu Phe Ala Lys Leu Lys Thr
1               5                   10                  15

Gln Thr Gln Ala Ser Asp Phe Pro Ile Gly Thr Ser Leu Lys Tyr Glu
            20                  25                  30

Cys Arg Pro Glu Tyr Tyr Gly Arg Pro Phe Ser Ile Thr Cys Leu Asp
        35                  40                  45

Asn Leu Val Trp Ser Ser Pro Lys Asp Val Cys Lys Arg Lys Ser Cys
    50                  55                  60

Lys Thr Pro Pro Asp Pro Val Asn Gly Met Val His Val Ile Thr Asp
65                  70                  75                  80

Ile Gln Val Gly Ser Arg Ile Gln Tyr Ser Cys Thr Thr Gly His Arg
                85                  90                  95

Leu Ile Gly His Ser Ser Ala Glu Cys Ile Leu Ser Gly Asn Thr Ala
            100                 105                 110

His Trp Ser Thr Lys Pro Pro Ile Cys Gln Arg Ile Pro Cys Gly Leu
        115                 120                 125

Pro Pro Thr Ile Ala Asn Gly Asp Phe Ile Ser Thr Asn Arg Glu Asn
    130                 135                 140

Phe His Tyr Gly Ser Val Val Thr Tyr Arg Cys Asn Leu Gly Ser Arg
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
                180                 185                 190

Ile Ile

<210> SEQ ID NO 7
<211> LENGTH: 18
<212> TYPE: PRT
<213> ORGANISM: Artificial Sequence
<220> FEATURE:
<223> OTHER INFORMATION: Synthetic construct

<400> SEQUENCE: 7

Met Arg Leu Leu Ala Lys Ile Ile Cys Leu Met Leu Trp Ala Ile Cys
1               5                   10                  15

Val Ala

<210> SEQ ID NO 8
<211> LENGTH: 61
<212> TYPE: PRT
```

-continued

<213> ORGANISM: Homo sapiens

<400> SEQUENCE: 8

Gly His Cys Gln Ala Pro Asp His Phe Leu Phe Ala Lys Leu Lys Thr
1               5                   10                  15

Gln Thr Asn Ala Ser Asp Phe Pro Ile Gly Thr Ser Leu Lys Tyr Glu
                20                  25                  30

Cys Arg Pro Glu Tyr Tyr Gly Arg Pro Phe Ser Ile Thr Cys Leu Asp
            35                  40                  45

Asn Leu Val Trp Ser Ser Pro Lys Asp Val Cys Lys Arg
        50                  55                  60

<210> SEQ ID NO 9
<211> LENGTH: 61
<212> TYPE: PRT
<213> ORGANISM: Homo sapiens

<400> SEQUENCE: 9

Lys Ser Cys Lys Thr Pro Pro Asp Pro Val Asn Gly Met Val His Val
1               5                   10                  15

Ile Thr Asp Ile Gln Val Gly Ser Arg Ile Asn Tyr Ser Cys Thr Thr
                20                  25                  30

Gly His Arg Leu Ile Gly His Ser Ser Ala Glu Cys Ile Leu Ser Gly
            35                  40                  45

Asn Ala Ala His Trp Ser Thr Lys Pro Pro Ile Cys Gln
        50                  55                  60

<210> SEQ ID NO 10
<211> LENGTH: 72
<212> TYPE: PRT
<213> ORGANISM: Homo sapiens

<400> SEQUENCE: 10

Arg Ile Pro Cys Gly Leu Pro Pro Thr Ile Ala Asn Gly Asp Phe Ile
1               5                   10                  15

Ser Thr Asn Arg Glu Asn Phe His Tyr Gly Ser Val Val Thr Tyr Arg
                20                  25                  30

Cys Asn Pro Gly Ser Gly Gly Arg Lys Val Phe Glu Leu Val Gly Glu
            35                  40                  45

Pro Ser Ile Tyr Cys Thr Ser Asn Asp Asp Gln Val Gly Ile Trp Ser
        50                  55                  60

Gly Pro Ala Pro Gln Cys Ile Ile
65                  70

<210> SEQ ID NO 11
<211> LENGTH: 61
<212> TYPE: PRT
<213> ORGANISM: Homo sapiens

<400> SEQUENCE: 11

Lys Ser Cys Lys Thr Pro Pro Asp Pro Val Asn Gly Met Val His Val
1               5                   10                  15

Ile Thr Asp Ile Gln Val Gly Ser Arg Ile Asn Tyr Ser Cys Thr Thr
                20                  25                  30

Gly His Arg Leu Ile Gly His Ser Ser Ala Glu Cys Ile Leu Ser Gly
            35                  40                  45

Asn Thr Ala His Trp Ser Thr Lys Pro Pro Ile Cys Gln
        50                  55                  60

```
<210> SEQ ID NO 12
<211> LENGTH: 72
<212> TYPE: PRT
<213> ORGANISM: Homo sapiens

<400> SEQUENCE: 12

Arg Ile Pro Cys Gly Leu Pro Pro Thr Ile Ala Asn Gly Asp Phe Ile
1               5                   10                  15

Ser Thr Asn Arg Glu Asn Phe His Tyr Gly Ser Val Val Thr Tyr Arg
            20                  25                  30

Cys Asn Leu Gly Ser Arg Gly Arg Lys Val Phe Glu Leu Val Gly Glu
        35                  40                  45

Pro Ser Ile Tyr Cys Thr Ser Asn Asp Asp Gln Val Gly Ile Trp Ser
    50                  55                  60

Gly Pro Ala Pro Gln Cys Ile Ile
65                  70

<210> SEQ ID NO 13
<211> LENGTH: 388
<212> TYPE: PRT
<213> ORGANISM: Homo sapiens

<400> SEQUENCE: 13

Gly His Cys Gln Ala Pro Asp His Phe Leu Phe Ala Lys Leu Lys Thr
1               5                   10                  15

Gln Thr Asn Ala Ser Asp Phe Pro Ile Gly Thr Ser Leu Lys Tyr Glu
            20                  25                  30

Cys Arg Pro Glu Tyr Tyr Gly Arg Pro Phe Ser Ile Thr Cys Leu Asp
        35                  40                  45

Asn Leu Val Trp Ser Ser Pro Lys Asp Val Cys Lys Arg Lys Ser Cys
    50                  55                  60

Lys Thr Pro Pro Asp Pro Val Asn Gly Met Val His Val Ile Thr Asp
65                  70                  75                  80

Ile Gln Val Gly Ser Arg Ile Asn Tyr Ser Cys Thr Thr Gly His Arg
                85                  90                  95

Leu Ile Gly His Ser Ser Ala Glu Cys Ile Leu Ser Gly Asn Ala Ala
            100                 105                 110

His Trp Ser Thr Lys Pro Pro Ile Cys Gln Arg Ile Pro Cys Gly Leu
        115                 120                 125

Pro Pro Thr Ile Ala Asn Gly Asp Phe Ile Ser Thr Asn Arg Glu Asn
    130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Gly His Cys Gln Ala Pro Asp His Phe Leu Phe Ala Lys Leu
        195                 200                 205

Lys Thr Gln Thr Asn Ala Ser Asp Phe Pro Ile Gly Thr Ser Leu Lys
    210                 215                 220

Tyr Glu Cys Arg Pro Glu Tyr Tyr Gly Arg Pro Phe Ser Ile Thr Cys
225                 230                 235                 240

Leu Asp Asn Leu Val Trp Ser Ser Pro Lys Asp Val Cys Lys Arg Lys
                245                 250                 255
```

Ser Cys Lys Thr Pro Pro Asp Pro Val Asn Gly Met Val His Val Ile
            260                 265                 270

Thr Asp Ile Gln Val Gly Ser Arg Ile Asn Tyr Ser Cys Thr Thr Gly
        275                 280                 285

His Arg Leu Ile Gly His Ser Ser Ala Glu Cys Ile Leu Ser Gly Asn
    290                 295                 300

Thr Ala His Trp Ser Thr Lys Pro Pro Ile Cys Gln Arg Ile Pro Cys
305                 310                 315                 320

Gly Leu Pro Pro Thr Ile Ala Asn Gly Asp Phe Ile Ser Thr Asn Arg
                325                 330                 335

Glu Asn Phe His Tyr Gly Ser Val Val Thr Tyr Arg Cys Asn Leu Gly
            340                 345                 350

Ser Arg Gly Arg Lys Val Phe Glu Leu Val Gly Glu Pro Ser Ile Tyr
        355                 360                 365

Cys Thr Ser Asn Asp Asp Gln Val Gly Ile Trp Ser Gly Pro Ala Pro
    370                 375                 380

Gln Cys Ile Ile
385

<210> SEQ ID NO 14
<211> LENGTH: 423
<212> TYPE: PRT
<213> ORGANISM: Homo sapiens
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: MISC_FEATURE
<222> LOCATION: (196)..(229)
<223> OTHER INFORMATION: Xaa can be any naturally occurring amino acid
      or absent

<400> SEQUENCE: 14

Gly His Cys Gln Ala Pro Asp His Phe Leu Phe Ala Lys Leu Lys Thr
1               5                   10                  15

Gln Thr Asn Ala Ser Asp Phe Pro Ile Gly Thr Ser Leu Lys Tyr Glu
            20                  25                  30

Cys Arg Pro Glu Tyr Tyr Gly Arg Pro Phe Ser Ile Thr Cys Leu Asp
        35                  40                  45

Asn Leu Val Trp Ser Ser Pro Lys Asp Val Cys Lys Arg Lys Ser Cys
    50                  55                  60

Lys Thr Pro Pro Asp Pro Val Asn Gly Met Val His Val Ile Thr Asp
65                  70                  75                  80

Ile Gln Val Gly Ser Arg Ile Asn Tyr Ser Cys Thr Thr Gly His Arg
                85                  90                  95

Leu Ile Gly His Ser Ser Ala Glu Cys Ile Leu Ser Gly Asn Ala Ala
            100                 105                 110

His Trp Ser Thr Lys Pro Pro Ile Cys Gln Arg Ile Pro Cys Gly Leu
        115                 120                 125

Pro Pro Thr Ile Ala Asn Gly Asp Phe Ile Ser Thr Asn Arg Glu Asn
    130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

```
Ile Ile Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa
    210                 215                 220

Xaa Xaa Xaa Xaa Xaa Gly His Cys Gln Ala Pro Asp His Phe Leu Phe
225                 230                 235                 240

Ala Lys Leu Lys Thr Gln Thr Asn Ala Ser Asp Phe Pro Ile Gly Thr
                245                 250                 255

Ser Leu Lys Tyr Glu Cys Arg Pro Glu Tyr Tyr Gly Arg Pro Phe Ser
                260                 265                 270

Ile Thr Cys Leu Asp Asn Leu Val Trp Ser Ser Pro Lys Asp Val Cys
            275                 280                 285

Lys Arg Lys Ser Cys Lys Thr Pro Pro Asp Pro Val Asn Gly Met Val
        290                 295                 300

His Val Ile Thr Asp Ile Gln Val Gly Ser Arg Ile Asn Tyr Ser Cys
305                 310                 315                 320

Thr Thr Gly His Arg Leu Ile Gly His Ser Ser Ala Glu Cys Ile Leu
                325                 330                 335

Ser Gly Asn Thr Ala His Trp Ser Thr Lys Pro Pro Ile Cys Gln Arg
                340                 345                 350

Ile Pro Cys Gly Leu Pro Pro Thr Ile Ala Asn Gly Asp Phe Ile Ser
            355                 360                 365

Thr Asn Arg Glu Asn Phe His Tyr Gly Ser Val Val Thr Tyr Arg Cys
        370                 375                 380

Asn Leu Gly Ser Arg Gly Arg Lys Val Phe Glu Leu Val Gly Glu Pro
385                 390                 395                 400

Ser Ile Tyr Cys Thr Ser Asn Asp Asp Gln Val Gly Ile Trp Ser Gly
                405                 410                 415

Pro Ala Pro Gln Cys Ile Ile
                420

<210> SEQ ID NO 15
<211> LENGTH: 388
<212> TYPE: PRT
<213> ORGANISM: Homo sapiens

<400> SEQUENCE: 15

Gly His Cys Gln Ala Pro Asp His Phe Leu Phe Ala Lys Leu Lys Thr
1               5                   10                  15

Gln Thr Gln Ala Ser Asp Phe Pro Ile Gly Thr Ser Leu Lys Tyr Glu
            20                  25                  30

Cys Arg Pro Glu Tyr Tyr Gly Arg Pro Phe Ser Ile Thr Cys Leu Asp
        35                  40                  45

Asn Leu Val Trp Ser Ser Pro Lys Asp Val Cys Lys Arg Lys Ser Cys
    50                  55                  60

Lys Thr Pro Pro Asp Pro Val Asn Gly Met Val His Val Ile Thr Asp
65                  70                  75                  80

Ile Gln Val Gly Ser Arg Ile Gln Tyr Ser Cys Thr Thr Gly His Arg
                85                  90                  95

Leu Ile Gly His Ser Ser Ala Glu Cys Ile Leu Ser Gly Asn Ala Ala
            100                 105                 110

His Trp Ser Thr Lys Pro Pro Ile Cys Gln Arg Ile Pro Cys Gly Leu
        115                 120                 125

Pro Pro Thr Ile Ala Asn Gly Asp Phe Ile Ser Thr Asn Arg Glu Asn
```

```
                130              135                140
    Phe His Tyr Gly Ser Val Val Thr Tyr Arg Cys Asn Pro Gly Ser Gly
    145                 150                 155                 160

Gly Arg Lys Val Phe Glu Leu Val Gly Glu Pro Ser Ile Tyr Cys Thr
                    165                 170                 175

Ser Asn Asp Asp Gln Val Gly Ile Trp Ser Gly Pro Ala Pro Gln Cys
                180                 185                 190

Ile Ile Gly His Cys Gln Ala Pro Asp His Phe Leu Phe Ala Lys Leu
                195                 200                 205

Lys Thr Gln Thr Gln Ala Ser Asp Phe Pro Ile Gly Thr Ser Leu Lys
                210                 215                 220

Tyr Glu Cys Arg Pro Glu Tyr Tyr Gly Arg Pro Phe Ser Ile Thr Cys
    225                 230                 235                 240

Leu Asp Asn Leu Val Trp Ser Ser Pro Lys Asp Val Cys Lys Arg Lys
                    245                 250                 255

Ser Cys Lys Thr Pro Pro Asp Pro Val Asn Gly Met Val His Val Ile
                260                 265                 270

Thr Asp Ile Gln Val Gly Ser Arg Ile Gln Tyr Ser Cys Thr Thr Gly
                275                 280                 285

His Arg Leu Ile Gly His Ser Ser Ala Glu Cys Ile Leu Ser Gly Asn
                290                 295                 300

Thr Ala His Trp Ser Thr Lys Pro Pro Ile Cys Gln Arg Ile Pro Cys
    305                 310                 315                 320

Gly Leu Pro Pro Thr Ile Ala Asn Gly Asp Phe Ile Ser Thr Asn Arg
                    325                 330                 335

Glu Asn Phe His Tyr Gly Ser Val Val Thr Tyr Arg Cys Asn Leu Gly
                340                 345                 350

Ser Arg Gly Arg Lys Val Phe Glu Leu Val Gly Glu Pro Ser Ile Tyr
                355                 360                 365

Cys Thr Ser Asn Asp Asp Gln Val Gly Ile Trp Ser Gly Pro Ala Pro
                370                 375                 380

Gln Cys Ile Ile
    385

<210> SEQ ID NO 16
<211> LENGTH: 61
<212> TYPE: PRT
<213> ORGANISM: Homo sapiens
<220> FEATURE:
<221> NAME/KEY: MISC_FEATURE
<222> LOCATION: (50)..(50)
<223> OTHER INFORMATION: Xaa = Ala or Thr

<400> SEQUENCE: 16

Lys Ser Cys Lys Thr Pro Pro Asp Pro Val Asn Gly Met Val His Val
    1               5                   10                  15

Ile Thr Asp Ile Gln Val Gly Ser Arg Ile Asn Tyr Ser Cys Thr Thr
                    20                  25                  30

Gly His Arg Leu Ile Gly His Ser Ser Ala Glu Cys Ile Leu Ser Gly
                35                  40                  45

Asn Xaa Ala His Trp Ser Thr Lys Pro Pro Ile Cys Gln
    50                  55                  60

<210> SEQ ID NO 17
<211> LENGTH: 72
<212> TYPE: PRT
<213> ORGANISM: Homo sapiens
```

```
<220> FEATURE:
<221> NAME/KEY: MISC_FEATURE
<222> LOCATION: (35)..(35)
<223> OTHER INFORMATION: Xaa = Pro or Leu
<220> FEATURE:
<221> NAME/KEY: MISC_FEATURE
<222> LOCATION: (38)..(38)
<223> OTHER INFORMATION: Xaa = Gly or Arg

<400> SEQUENCE: 17
```

Arg Ile Pro Cys Gly Leu Pro Pro Thr Ile Ala Asn Gly Asp Phe Ile
1               5                   10                  15

Ser Thr Asn Arg Glu Asn Phe His Tyr Gly Ser Val Val Thr Tyr Arg
            20                  25                  30

Cys Asn Xaa Gly Ser Xaa Gly Arg Lys Val Phe Glu Leu Val Gly Glu
            35                  40                  45

Pro Ser Ile Tyr Cys Thr Ser Asn Asp Asp Gln Val Gly Ile Trp Ser
        50                  55                  60

Gly Pro Ala Pro Gln Cys Ile Ile
65                  70

```
<210> SEQ ID NO 18
<211> LENGTH: 1663
<212> TYPE: PRT
<213> ORGANISM: Homo sapiens

<400> SEQUENCE: 18
```

Met Gly Pro Thr Ser Gly Pro Ser Leu Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

```
Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
        260                 265                 270

Phe Gly Ile Gln Asp Gly Glu Gln Arg Ile Ser Leu Pro Glu Ser Leu
    275                 280                 285

Lys Arg Ile Pro Ile Glu Asp Gly Ser Gly Glu Val Val Leu Ser Arg
290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365

Pro Phe Asp Leu Met Val Phe Val Thr Asn Pro Asp Gly Ser Pro Ala
    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445

Val Gly Asn Ser Asn Asn Tyr Leu His Leu Ser Val Leu Arg Thr Glu
450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
```

-continued

Val Gln Leu Thr Glu Lys Arg Met Asp Lys Val Gly Lys Tyr Pro Lys
                660                 665                 670

Glu Leu Arg Lys Cys Cys Glu Asp Gly Met Arg Glu Asn Pro Met Arg
    675                 680                 685

Phe Ser Cys Gln Arg Arg Thr Arg Phe Ile Ser Leu Gly Glu Ala Cys
690                 695                 700

Lys Lys Val Phe Leu Asp Cys Cys Asn Tyr Ile Thr Glu Leu Arg Arg
705                 710                 715                 720

Gln His Ala Arg Ala Ser His Leu Gly Leu Ala Arg Ser Asn Leu Asp
    725                 730                 735

Glu Asp Ile Ile Ala Glu Asn Ile Val Ser Arg Ser Glu Phe Pro
740                 745                 750

Glu Ser Trp Leu Trp Asn Val Glu Asp Leu Lys Glu Pro Pro Lys Asn
    755                 760                 765

Gly Ile Ser Thr Lys Leu Met Asn Ile Phe Leu Lys Asp Ser Ile Thr
770                 775                 780

Thr Trp Glu Ile Leu Ala Val Ser Met Ser Asp Lys Lys Gly Ile Cys
785                 790                 795                 800

Val Ala Asp Pro Phe Glu Val Thr Val Met Gln Asp Phe Phe Ile Asp
    805                 810                 815

Leu Arg Leu Pro Tyr Ser Val Val Arg Asn Glu Gln Val Glu Ile Arg
820                 825                 830

Ala Val Leu Tyr Asn Tyr Arg Gln Asn Gln Glu Leu Lys Val Arg Val
    835                 840                 845

Glu Leu Leu His Asn Pro Ala Phe Cys Ser Leu Ala Thr Thr Lys Arg
850                 855                 860

Arg His Gln Gln Thr Val Thr Ile Pro Pro Lys Ser Ser Leu Ser Val
865                 870                 875                 880

Pro Tyr Val Ile Val Pro Leu Lys Thr Gly Leu Gln Glu Val Glu Val
    885                 890                 895

Lys Ala Ala Val Tyr His His Phe Ile Ser Asp Gly Val Arg Lys Ser
900                 905                 910

Leu Lys Val Val Pro Glu Gly Ile Arg Met Asn Lys Thr Val Ala Val
    915                 920                 925

Arg Thr Leu Asp Pro Glu Arg Leu Gly Arg Glu Gly Val Gln Lys Glu
930                 935                 940

Asp Ile Pro Pro Ala Asp Leu Ser Asp Gln Val Pro Asp Thr Glu Ser
945                 950                 955                 960

Glu Thr Arg Ile Leu Leu Gln Gly Thr Pro Val Ala Gln Met Thr Glu
    965                 970                 975

Asp Ala Val Asp Ala Glu Arg Leu Lys His Leu Ile Val Thr Pro Ser
980                 985                 990

Gly Cys Gly Glu Gln Asn Met Ile Gly Met Thr Pro Thr Val Ile
    995                 1000                1005

Ala Val His Tyr Leu Asp Glu Thr Glu Gln Trp Glu Lys Phe Gly
1010                1015                1020

Leu Glu Lys Arg Gln Gly Ala Leu Glu Leu Ile Lys Lys Gly Tyr
    1025                1030                1035

Thr Gln Gln Leu Ala Phe Arg Gln Pro Ser Ser Ala Phe Ala Ala
1040                1045                1050

Phe Val Lys Arg Ala Pro Ser Thr Trp Leu Thr Ala Tyr Val Val
    1055                1060                1065

1070                1075                1080

```
Lys Val Phe Ser Leu Ala Val Asn Leu Ile Ala Ile Asp Ser Gln
    1085            1090            1095

Val Leu Cys Gly Ala Val Lys Trp Leu Ile Leu Glu Lys Gln Lys
    1100            1105            1110

Pro Asp Gly Val Phe Gln Glu Asp Ala Pro Val Ile His Gln Glu
    1115            1120            1125

Met Ile Gly Gly Leu Arg Asn Asn Asn Glu Lys Asp Met Ala Leu
    1130            1135            1140

Thr Ala Phe Val Leu Ile Ser Leu Gln Glu Ala Lys Asp Ile Cys
    1145            1150            1155

Glu Glu Gln Val Asn Ser Leu Pro Gly Ser Ile Thr Lys Ala Gly
    1160            1165            1170

Asp Phe Leu Glu Ala Asn Tyr Met Asn Leu Gln Arg Ser Tyr Thr
    1175            1180            1185

Val Ala Ile Ala Gly Tyr Ala Leu Ala Gln Met Gly Arg Leu Lys
    1190            1195            1200

Gly Pro Leu Leu Asn Lys Phe Leu Thr Thr Ala Lys Asp Lys Asn
    1205            1210            1215

Arg Trp Glu Asp Pro Gly Lys Gln Leu Tyr Asn Val Glu Ala Thr
    1220            1225            1230

Ser Tyr Ala Leu Leu Ala Leu Leu Gln Leu Lys Asp Phe Asp Phe
    1235            1240            1245

Val Pro Pro Val Val Arg Trp Leu Asn Glu Gln Arg Tyr Tyr Gly
    1250            1255            1260

Gly Gly Tyr Gly Ser Thr Gln Ala Thr Phe Met Val Phe Gln Ala
    1265            1270            1275

Leu Ala Gln Tyr Gln Lys Asp Ala Pro Asp His Gln Glu Leu Asn
    1280            1285            1290

Leu Asp Val Ser Leu Gln Leu Pro Ser Arg Ser Ser Lys Ile Thr
    1295            1300            1305

His Arg Ile His Trp Glu Ser Ala Ser Leu Leu Arg Ser Glu Glu
    1310            1315            1320

Thr Lys Glu Asn Glu Gly Phe Thr Val Thr Ala Glu Gly Lys Gly
    1325            1330            1335

Gln Gly Thr Leu Ser Val Val Thr Met Tyr His Ala Lys Ala Lys
    1340            1345            1350

Asp Gln Leu Thr Cys Asn Lys Phe Asp Leu Lys Val Thr Ile Lys
    1355            1360            1365

Pro Ala Pro Glu Thr Glu Lys Arg Pro Gln Asp Ala Lys Asn Thr
    1370            1375            1380

Met Ile Leu Glu Ile Cys Thr Arg Tyr Arg Gly Asp Gln Asp Ala
    1385            1390            1395

Thr Met Ser Ile Leu Asp Ile Ser Met Met Thr Gly Phe Ala Pro
    1400            1405            1410

Asp Thr Asp Asp Leu Lys Gln Leu Ala Asn Gly Val Asp Arg Tyr
    1415            1420            1425

Ile Ser Lys Tyr Glu Leu Asp Lys Ala Phe Ser Asp Arg Asn Thr
    1430            1435            1440

Leu Ile Ile Tyr Leu Asp Lys Val Ser His Ser Glu Asp Asp Cys
    1445            1450            1455

Leu Ala Phe Lys Val His Gln Tyr Phe Asn Val Glu Leu Ile Gln
    1460            1465            1470
```

```
Pro Gly Ala Val Lys Val Tyr Ala Tyr Asn Leu Glu Glu Ser
    1475                1480                1485

Cys Thr Arg Phe Tyr His Pro Glu Lys Glu Asp Gly Lys Leu Asn
    1490                1495                1500

Lys Leu Cys Arg Asp Glu Leu Cys Arg Cys Ala Glu Glu Asn Cys
    1505                1510                1515

Phe Ile Gln Lys Ser Asp Asp Lys Val Thr Leu Glu Glu Arg Leu
    1520                1525                1530

Asp Lys Ala Cys Glu Pro Gly Val Asp Tyr Val Tyr Lys Thr Arg
    1535                1540                1545

Leu Val Lys Val Gln Leu Ser Asn Asp Phe Asp Glu Tyr Ile Met
    1550                1555                1560

Ala Ile Glu Gln Thr Ile Lys Ser Gly Ser Asp Glu Val Gln Val
    1565                1570                1575

Gly Gln Gln Arg Thr Phe Ile Ser Pro Ile Lys Cys Arg Glu Ala
    1580                1585                1590

Leu Lys Leu Glu Glu Lys Lys His Tyr Leu Met Trp Gly Leu Ser
    1595                1600                1605

Ser Asp Phe Trp Gly Glu Lys Pro Asn Leu Ser Tyr Ile Ile Gly
    1610                1615                1620

Lys Asp Thr Trp Val Glu His Trp Pro Glu Glu Asp Glu Cys Gln
    1625                1630                1635

Asp Glu Glu Asn Gln Lys Gln Cys Gln Asp Leu Gly Ala Phe Thr
    1640                1645                1650

Glu Ser Met Val Val Phe Gly Cys Pro Asn
    1655                1660
```

<210> SEQ ID NO 19
<211> LENGTH: 645
<212> TYPE: PRT
<213> ORGANISM: Homo sapiens

<400> SEQUENCE: 19

```
Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
                20                  25                  30

Val Thr Val Thr Val His Asp Phe Pro Gly Lys Lys Leu Val Leu Ser
            35                  40                  45

Ser Glu Lys Thr Val Leu Thr Pro Ala Thr Asn His Met Gly Asn Val
        50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175
```

-continued

Val Asn Met Gly Gln Trp Lys Ile Arg Ala Tyr Tyr Glu Asn Ser Pro
            180                 185                 190

Gln Gln Val Phe Ser Thr Glu Phe Glu Val Lys Glu Tyr Val Leu Pro
        195                 200                 205

Ser Phe Glu Val Ile Val Glu Pro Thr Glu Lys Phe Tyr Tyr Ile Tyr
    210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
            260                 265                 270

Asp Gly Ser Gly Glu Val Val Leu Ser Arg Lys Val Leu Leu Asp Gly
        275                 280                 285

Val Gln Asn Pro Arg Ala Glu Asp Leu Val Gly Lys Ser Leu Tyr Val
    290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
            340                 345                 350

Phe Val Thr Asn Pro Asp Gly Ser Pro Ala Tyr Arg Val Pro Val Ala
        355                 360                 365

Val Gln Gly Glu Asp Thr Val Gln Ser Leu Thr Gln Gly Asp Gly Val
    370                 375                 380

Ala Lys Leu Ser Ile Asn Thr His Pro Ser Gln Lys Pro Leu Ser Ile
385                 390                 395                 400

Thr Val Arg Thr Lys Lys Gln Glu Leu Ser Glu Ala Glu Gln Ala Thr
                405                 410                 415

Arg Thr Met Gln Ala Leu Pro Tyr Ser Thr Val Gly Asn Ser Asn Asn
            420                 425                 430

Tyr Leu His Leu Ser Val Leu Arg Thr Glu Leu Arg Pro Gly Glu Thr
        435                 440                 445

Leu Asn Val Asn Phe Leu Leu Arg Met Asp Arg Ala His Glu Ala Lys
    450                 455                 460

Ile Arg Tyr Tyr Thr Tyr Leu Ile Met Asn Lys Gly Arg Leu Leu Lys
465                 470                 475                 480

Ala Gly Arg Gln Val Arg Glu Pro Gly Gln Asp Leu Val Val Leu Pro
                485                 490                 495

Leu Ser Ile Thr Thr Asp Phe Ile Pro Ser Phe Arg Leu Val Ala Tyr
            500                 505                 510

Tyr Thr Leu Ile Gly Ala Ser Gly Gln Arg Glu Val Val Ala Asp Ser
        515                 520                 525

Val Trp Val Asp Val Lys Asp Ser Cys Val Gly Ser Leu Val Val Lys
    530                 535                 540

Ser Gly Gln Ser Glu Asp Arg Gln Pro Val Pro Gly Gln Gln Met Thr
545                 550                 555                 560

Leu Lys Ile Glu Gly Asp His Gly Ala Arg Val Val Leu Val Ala Val
                565                 570                 575

Asp Lys Gly Val Phe Val Leu Asn Lys Lys Asn Lys Leu Thr Gln Ser
            580                 585                 590

```
Lys Ile Trp Asp Val Val Glu Lys Ala Asp Ile Gly Cys Thr Pro Gly
            595                 600                 605

Ser Gly Lys Asp Tyr Ala Gly Val Phe Ser Asp Ala Gly Leu Thr Phe
            610                 615                 620

Thr Ser Ser Ser Gly Gln Gln Thr Ala Gln Arg Ala Glu Leu Gln Cys
625                 630                 635                 640

Pro Gln Pro Ala Ala
                645

<210> SEQ ID NO 20
<211> LENGTH: 915
<212> TYPE: PRT
<213> ORGANISM: Homo sapiens

<400> SEQUENCE: 20

Ser Asn Leu Asp Glu Asp Ile Ile Ala Glu Asn Ile Val Ser Arg
1               5                   10                  15

Ser Glu Phe Pro Glu Ser Trp Leu Trp Asn Val Glu Asp Leu Lys Glu
            20                  25                  30

Pro Pro Lys Asn Gly Ile Ser Thr Lys Leu Met Asn Ile Phe Leu Lys
            35                  40                  45

Asp Ser Ile Thr Thr Trp Glu Ile Leu Ala Val Ser Met Ser Asp Lys
        50                  55                  60

Lys Gly Ile Cys Val Ala Asp Pro Phe Glu Val Thr Val Met Gln Asp
65                  70                  75                  80

Phe Phe Ile Asp Leu Arg Leu Pro Tyr Ser Val Val Arg Asn Glu Gln
                85                  90                  95

Val Glu Ile Arg Ala Val Leu Tyr Asn Tyr Arg Gln Asn Gln Glu Leu
            100                 105                 110

Lys Val Arg Val Glu Leu Leu His Asn Pro Ala Phe Cys Ser Leu Ala
            115                 120                 125

Thr Thr Lys Arg Arg His Gln Gln Thr Val Thr Ile Pro Pro Lys Ser
        130                 135                 140

Ser Leu Ser Val Pro Tyr Val Ile Val Pro Leu Lys Thr Gly Leu Gln
145                 150                 155                 160

Glu Val Glu Val Lys Ala Ala Val Tyr His His Phe Ile Ser Asp Gly
                165                 170                 175

Val Arg Lys Ser Leu Lys Val Val Pro Glu Gly Ile Arg Met Asn Lys
            180                 185                 190

Thr Val Ala Val Arg Thr Leu Asp Pro Glu Arg Leu Gly Arg Glu Gly
            195                 200                 205

Val Gln Lys Glu Asp Ile Pro Pro Ala Asp Leu Ser Asp Gln Val Pro
        210                 215                 220

Asp Thr Glu Ser Glu Thr Arg Ile Leu Leu Gln Gly Thr Pro Val Ala
225                 230                 235                 240

Gln Met Thr Glu Asp Ala Val Asp Ala Glu Arg Leu Lys His Leu Ile
                245                 250                 255

Val Thr Pro Ser Gly Cys Gly Glu Gln Asn Met Ile Gly Met Thr Pro
            260                 265                 270

Thr Val Ile Ala Val His Tyr Leu Asp Glu Thr Glu Gln Trp Glu Lys
            275                 280                 285

Phe Gly Leu Glu Lys Arg Gln Gly Ala Leu Glu Leu Ile Lys Lys Gly
        290                 295                 300

Tyr Thr Gln Gln Leu Ala Phe Arg Gln Pro Ser Ser Ala Phe Ala Ala
305                 310                 315                 320
```

Phe Val Lys Arg Ala Pro Ser Thr Trp Leu Thr Ala Tyr Val Val Lys
                325                 330                 335

Val Phe Ser Leu Ala Val Asn Leu Ile Ala Ile Asp Ser Gln Val Leu
                340                 345                 350

Cys Gly Ala Val Lys Trp Leu Ile Leu Glu Lys Gln Lys Pro Asp Gly
                355                 360                 365

Val Phe Gln Glu Asp Ala Pro Val Ile His Gln Glu Met Ile Gly Gly
                370                 375                 380

Leu Arg Asn Asn Asn Glu Lys Asp Met Ala Leu Thr Ala Phe Val Leu
385                 390                 395                 400

Ile Ser Leu Gln Glu Ala Lys Asp Ile Cys Glu Glu Gln Val Asn Ser
                405                 410                 415

Leu Pro Gly Ser Ile Thr Lys Ala Gly Asp Phe Leu Glu Ala Asn Tyr
                420                 425                 430

Met Asn Leu Gln Arg Ser Tyr Thr Val Ala Ile Ala Gly Tyr Ala Leu
                435                 440                 445

Ala Gln Met Gly Arg Leu Lys Gly Pro Leu Leu Asn Lys Phe Leu Thr
                450                 455                 460

Thr Ala Lys Asp Lys Asn Arg Trp Glu Asp Pro Gly Lys Gln Leu Tyr
465                 470                 475                 480

Asn Val Glu Ala Thr Ser Tyr Ala Leu Leu Ala Leu Leu Gln Leu Lys
                485                 490                 495

Asp Phe Asp Phe Val Pro Pro Val Val Arg Trp Leu Asn Glu Gln Arg
                500                 505                 510

Tyr Tyr Gly Gly Gly Tyr Gly Ser Thr Gln Ala Thr Phe Met Val Phe
                515                 520                 525

Gln Ala Leu Ala Gln Tyr Gln Lys Asp Ala Pro Asp His Gln Glu Leu
                530                 535                 540

Asn Leu Asp Val Ser Leu Gln Leu Pro Ser Arg Ser Ser Lys Ile Thr
545                 550                 555                 560

His Arg Ile His Trp Glu Ser Ala Ser Leu Leu Arg Ser Glu Glu Thr
                565                 570                 575

Lys Glu Asn Glu Gly Phe Thr Val Thr Ala Glu Gly Lys Gly Gln Gly
                580                 585                 590

Thr Leu Ser Val Val Thr Met Tyr His Ala Lys Ala Lys Asp Gln Leu
                595                 600                 605

Thr Cys Asn Lys Phe Asp Leu Lys Val Thr Ile Lys Pro Ala Pro Glu
610                 615                 620

Thr Glu Lys Arg Pro Gln Asp Ala Lys Asn Thr Met Ile Leu Glu Ile
625                 630                 635                 640

Cys Thr Arg Tyr Arg Gly Asp Gln Asp Ala Thr Met Ser Ile Leu Asp
                645                 650                 655

Ile Ser Met Met Thr Gly Phe Ala Pro Asp Thr Asp Asp Leu Lys Gln
                660                 665                 670

Leu Ala Asn Gly Val Asp Arg Tyr Ile Ser Lys Tyr Glu Leu Asp Lys
                675                 680                 685

Ala Phe Ser Asp Arg Asn Thr Leu Ile Ile Tyr Leu Asp Lys Val Ser
                690                 695                 700

His Ser Glu Asp Asp Cys Leu Ala Phe Lys Val His Gln Tyr Phe Asn
705                 710                 715                 720

Val Glu Leu Ile Gln Pro Gly Ala Val Lys Val Tyr Ala Tyr Tyr Asn
                725                 730                 735

-continued

```
Leu Glu Glu Ser Cys Thr Arg Phe Tyr His Pro Glu Lys Glu Asp Gly
        740                 745                 750

Lys Leu Asn Lys Leu Cys Arg Asp Glu Leu Cys Arg Cys Ala Glu Glu
        755                 760                 765

Asn Cys Phe Ile Gln Lys Ser Asp Asp Lys Val Thr Leu Glu Glu Arg
        770                 775                 780

Leu Asp Lys Ala Cys Glu Pro Gly Val Asp Tyr Val Tyr Lys Thr Arg
785                 790                 795                 800

Leu Val Lys Val Gln Leu Ser Asn Asp Phe Asp Glu Tyr Ile Met Ala
                805                 810                 815

Ile Glu Gln Thr Ile Lys Ser Gly Ser Asp Glu Val Gln Val Gly Gln
        820                 825                 830

Gln Arg Thr Phe Ile Ser Pro Ile Lys Cys Arg Glu Ala Leu Lys Leu
        835                 840                 845

Glu Glu Lys Lys His Tyr Leu Met Trp Gly Leu Ser Ser Asp Phe Trp
        850                 855                 860

Gly Glu Lys Pro Asn Leu Ser Tyr Ile Ile Gly Lys Asp Thr Trp Val
865                 870                 875                 880

Glu His Trp Pro Glu Glu Asp Glu Cys Gln Asp Glu Glu Asn Gln Lys
                885                 890                 895

Gln Cys Gln Asp Leu Gly Ala Phe Thr Glu Ser Met Val Val Phe Gly
        900                 905                 910

Cys Pro Asn
        915

<210> SEQ ID NO 21
<211> LENGTH: 77
<212> TYPE: PRT
<213> ORGANISM: Homo sapiens

<400> SEQUENCE: 21

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
                20                  25                  30

Arg Phe Ser Cys Gln Arg Arg Thr Arg Phe Ile Ser Leu Gly Glu Ala
            35                  40                  45

Cys Lys Lys Val Phe Leu Asp Cys Cys Asn Tyr Ile Thr Glu Leu Arg
        50                  55                  60

Arg Gln His Ala Arg Ala Ser His Leu Gly Leu Ala Arg
65                  70                  75

<210> SEQ ID NO 22
<211> LENGTH: 555
<212> TYPE: PRT
<213> ORGANISM: Homo sapiens

<400> SEQUENCE: 22

Ser Asn Leu Asp Glu Asp Ile Ile Ala Glu Glu Asn Ile Val Ser Arg
1               5                   10                  15

Ser Glu Phe Pro Glu Ser Trp Leu Trp Asn Val Glu Asp Leu Lys Glu
                20                  25                  30

Pro Pro Lys Asn Gly Ile Ser Thr Lys Leu Met Asn Ile Phe Leu Lys
            35                  40                  45

Asp Ser Ile Thr Thr Trp Glu Ile Leu Ala Val Ser Met Ser Asp Lys
        50                  55                  60
```

```
Lys Gly Ile Cys Val Ala Asp Pro Phe Glu Val Thr Val Met Gln Asp
 65                  70                  75                  80

Phe Phe Ile Asp Leu Arg Leu Pro Tyr Ser Val Val Arg Asn Glu Gln
                 85                  90                  95

Val Glu Ile Arg Ala Val Leu Tyr Asn Tyr Arg Gln Asn Gln Glu Leu
            100                 105                 110

Lys Val Arg Val Glu Leu Leu His Asn Pro Ala Phe Cys Ser Leu Ala
        115                 120                 125

Thr Thr Lys Arg Arg His Gln Gln Thr Val Thr Ile Pro Pro Lys Ser
    130                 135                 140

Ser Leu Ser Val Pro Tyr Val Ile Val Pro Leu Lys Thr Gly Leu Gln
145                 150                 155                 160

Glu Val Glu Val Lys Ala Ala Val Tyr His His Phe Ile Ser Asp Gly
                165                 170                 175

Val Arg Lys Ser Leu Lys Val Val Pro Glu Gly Ile Arg Met Asn Lys
            180                 185                 190

Thr Val Ala Val Arg Thr Leu Asp Pro Glu Arg Leu Gly Arg Glu Gly
        195                 200                 205

Val Gln Lys Glu Asp Ile Pro Pro Ala Asp Leu Ser Asp Gln Val Pro
    210                 215                 220

Asp Thr Glu Ser Glu Thr Arg Ile Leu Leu Gln Gly Thr Pro Val Ala
225                 230                 235                 240

Gln Met Thr Glu Asp Ala Val Asp Ala Glu Arg Leu Lys His Leu Ile
                245                 250                 255

Val Thr Pro Ser Gly Cys Gly Glu Gln Asn Met Ile Gly Met Thr Pro
            260                 265                 270

Thr Val Ile Ala Val His Tyr Leu Asp Glu Thr Glu Gln Trp Glu Lys
        275                 280                 285

Phe Gly Leu Glu Lys Arg Gln Gly Ala Leu Glu Leu Ile Lys Lys Gly
    290                 295                 300

Tyr Thr Gln Gln Leu Ala Phe Arg Gln Pro Ser Ser Ala Phe Ala Ala
305                 310                 315                 320

Phe Val Lys Arg Ala Pro Ser Thr Trp Leu Thr Ala Tyr Val Val Lys
                325                 330                 335

Val Phe Ser Leu Ala Val Asn Leu Ile Ala Ile Asp Ser Gln Val Leu
            340                 345                 350

Cys Gly Ala Val Lys Trp Leu Ile Leu Glu Lys Gln Lys Pro Asp Gly
        355                 360                 365

Val Phe Gln Glu Asp Ala Pro Val Ile His Gln Glu Met Ile Gly Gly
    370                 375                 380

Leu Arg Asn Asn Asn Glu Lys Asp Met Ala Leu Thr Ala Phe Val Leu
385                 390                 395                 400

Ile Ser Leu Gln Glu Ala Lys Asp Ile Cys Glu Glu Gln Val Asn Ser
                405                 410                 415

Leu Pro Gly Ser Ile Thr Lys Ala Gly Asp Phe Leu Glu Ala Asn Tyr
            420                 425                 430

Met Asn Leu Gln Arg Ser Tyr Thr Val Ala Ile Ala Gly Tyr Ala Leu
        435                 440                 445

Ala Gln Met Gly Arg Leu Lys Gly Pro Leu Leu Asn Lys Phe Leu Thr
    450                 455                 460

Thr Ala Lys Asp Lys Asn Arg Trp Glu Asp Pro Gly Lys Gln Leu Tyr
465                 470                 475                 480

Asn Val Glu Ala Thr Ser Tyr Ala Leu Leu Ala Leu Leu Gln Leu Lys
```

```
                         485                 490                 495
Asp Phe Asp Phe Val Pro Pro Val Arg Trp Leu Asn Glu Gln Arg
                500                 505                 510
Tyr Tyr Gly Gly Gly Tyr Gly Ser Thr Gln Ala Thr Phe Met Val Phe
            515                 520                 525
Gln Ala Leu Ala Gln Tyr Gln Lys Asp Ala Pro Asp His Gln Glu Leu
        530                 535                 540
Asn Leu Asp Val Ser Leu Gln Leu Pro Ser Arg
545                 550                 555

<210> SEQ ID NO 23
<211> LENGTH: 343
<212> TYPE: PRT
<213> ORGANISM: Homo sapiens

<400> SEQUENCE: 23

Ser Glu Glu Thr Lys Glu Asn Glu Gly Phe Thr Val Thr Ala Glu Gly
1               5                   10                  15
Lys Gly Gln Gly Thr Leu Ser Val Val Thr Met Tyr His Ala Lys Ala
            20                  25                  30
Lys Asp Gln Leu Thr Cys Asn Lys Phe Asp Leu Lys Val Thr Ile Lys
        35                  40                  45
Pro Ala Pro Glu Thr Glu Lys Arg Pro Gln Asp Ala Lys Asn Thr Met
    50                  55                  60
Ile Leu Glu Ile Cys Thr Arg Tyr Arg Gly Asp Gln Asp Ala Thr Met
65                  70                  75                  80
Ser Ile Leu Asp Ile Ser Met Met Thr Gly Phe Ala Pro Asp Thr Asp
                85                  90                  95
Asp Leu Lys Gln Leu Ala Asn Gly Val Asp Arg Tyr Ile Ser Lys Tyr
            100                 105                 110
Glu Leu Asp Lys Ala Phe Ser Asp Arg Asn Thr Leu Ile Ile Tyr Leu
        115                 120                 125
Asp Lys Val Ser His Ser Glu Asp Asp Cys Leu Ala Phe Lys Val His
    130                 135                 140
Gln Tyr Phe Asn Val Glu Leu Ile Gln Pro Gly Ala Val Lys Val Tyr
145                 150                 155                 160
Ala Tyr Tyr Asn Leu Glu Glu Ser Cys Thr Arg Phe Tyr His Pro Glu
                165                 170                 175
Lys Glu Asp Gly Lys Leu Asn Lys Leu Cys Arg Asp Glu Leu Cys Arg
            180                 185                 190
Cys Ala Glu Glu Asn Cys Phe Ile Gln Lys Ser Asp Asp Lys Val Thr
        195                 200                 205
Leu Glu Glu Arg Leu Asp Lys Ala Cys Glu Pro Gly Val Asp Tyr Val
    210                 215                 220
Tyr Lys Thr Arg Leu Val Lys Val Gln Leu Ser Asn Asp Phe Asp Glu
225                 230                 235                 240
Tyr Ile Met Ala Ile Glu Gln Thr Ile Lys Ser Gly Ser Asp Glu Val
                245                 250                 255
Gln Val Gly Gln Gln Arg Thr Phe Ile Ser Pro Ile Lys Cys Arg Glu
            260                 265                 270
Ala Leu Lys Leu Glu Glu Lys Lys His Tyr Leu Met Trp Gly Leu Ser
        275                 280                 285
Ser Asp Phe Trp Gly Glu Lys Pro Asn Leu Ser Tyr Ile Ile Gly Lys
    290                 295                 300
```

```
Asp Thr Trp Val Glu His Trp Pro Glu Glu Glu Cys Gln Asp Glu
305                 310                 315                 320

Glu Asn Gln Lys Gln Cys Gln Asp Leu Gly Ala Phe Thr Glu Ser Met
            325                 330                 335

Val Val Phe Gly Cys Pro Asn
            340
```

<210> SEQ ID NO 24
<211> LENGTH: 17
<212> TYPE: PRT
<213> ORGANISM: Homo sapiens

<400> SEQUENCE: 24

```
Ser Ser Lys Ile Thr His Arg Ile His Trp Glu Ser Ala Ser Leu Leu
1               5                   10                  15

Arg
```

<210> SEQ ID NO 25
<211> LENGTH: 583
<212> TYPE: PRT
<213> ORGANISM: Homo sapiens

<400> SEQUENCE: 25

```
Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
                20                  25                  30

Cys Leu Ala Lys Lys Tyr Thr His Leu Ser Cys Asp Lys Val Phe Cys
            35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
```

```
                260                 265                 270
Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Thr Gln Glu Glu Thr
        290                 295                 300

Glu Ile Leu Thr Ala Asp Met Asp Ala Glu Arg Arg Ile Lys Ser
305                 310                 315                 320

Leu Leu Pro Lys Leu Ser Cys Gly Val Lys Asn Arg Met His Ile Arg
                325                 330                 335

Arg Lys Arg Ile Val Gly Gly Lys Arg Ala Gln Leu Gly Asp Leu Pro
                340                 345                 350

Trp Gln Val Ala Ile Lys Asp Ala Ser Gly Ile Thr Cys Gly Gly Ile
        355                 360                 365

Tyr Ile Gly Gly Cys Trp Ile Leu Thr Ala Ala His Cys Leu Arg Ala
        370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
                420                 425                 430

Ile Glu Met Lys Lys Asp Gly Asn Lys Lys Asp Cys Glu Leu Pro Arg
                435                 440                 445

Ser Ile Pro Ala Cys Val Pro Trp Ser Pro Tyr Leu Phe Gln Pro Asn
        450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
                500                 505                 510

Thr Tyr Asp Gly Ser Ile Asp Ala Cys Lys Gly Asp Ser Gly Gly Pro
        515                 520                 525

Leu Val Cys Met Asp Ala Asn Asn Val Thr Tyr Val Trp Gly Val Val
        530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
                580

<210> SEQ ID NO 26
<211> LENGTH: 235
<212> TYPE: PRT
<213> ORGANISM: Homo sapiens

<400> SEQUENCE: 26

Ile Val Gly Gly Lys Arg Ala Gln Leu Gly Asp Leu Pro Trp Gln Val
1               5                   10                  15

Ala Ile Lys Asp Ala Ser Gly Ile Thr Cys Gly Gly Ile Tyr Ile Gly
                20                  25                  30

Gly Cys Trp Ile Leu Thr Ala Ala His Cys Leu Arg Ala Ser Lys Thr
        35                  40                  45
```

His Arg Tyr Gln Ile Trp Thr Thr Val Val Asp Trp Ile His Pro Asp
    50                  55                  60

Leu Lys Arg Ile Val Ile Glu Tyr Val Asp Arg Ile Ile Phe His Glu
65                  70                  75                  80

Asn Tyr Asn Ala Gly Thr Tyr Gln Asn Asp Ile Ala Leu Ile Glu Met
                85                  90                  95

Lys Lys Asp Gly Asn Lys Lys Asp Cys Glu Leu Pro Arg Ser Ile Pro
            100                 105                 110

Ala Cys Val Pro Trp Ser Pro Tyr Leu Phe Gln Pro Asn Asp Thr Cys
        115                 120                 125

Ile Val Ser Gly Trp Gly Arg Glu Lys Asp Asn Glu Arg Val Phe Ser
130                 135                 140

Leu Gln Trp Gly Glu Val Lys Leu Ile Ser Asn Cys Ser Lys Phe Tyr
145                 150                 155                 160

Gly Asn Arg Phe Tyr Glu Lys Glu Met Glu Cys Ala Gly Thr Tyr Asp
                165                 170                 175

Gly Ser Ile Asp Ala Cys Lys Gly Asp Ser Gly Gly Pro Leu Val Cys
            180                 185                 190

Met Asp Ala Asn Asn Val Thr Tyr Val Trp Gly Val Val Ser Trp Gly
        195                 200                 205

Glu Asn Cys Gly Lys Pro Glu Phe Pro Gly Val Tyr Thr Lys Val Ala
    210                 215                 220

Asn Tyr Phe Asp Trp Ile Ser Tyr His Val Gly
225                 230                 235

<210> SEQ ID NO 27
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa = any amino acid except for Pro
<220> FEATURE:
<221> NAME/KEY: MISC_FEATURE
<222> LOCATION: (3)..(3)
<223> OTHER INFORMATION: Xaa = Ser or Thr

<400> SEQUENCE: 27

Asn Xaa Xaa
1

<210> SEQ ID NO 28
<211> LENGTH: 449
<212> TYPE: PRT
<213> ORGANISM: Artificial Sequence
<220> FEATURE:
<223> OTHER INFORMATION: Synthetic construct

<400> SEQUENCE: 28

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

```
Val Cys Arg Lys Gly Glu Trp Val Ala Leu Asn Pro Leu Arg Lys Cys
 65                  70                  75                  80

Gln Lys Arg Pro Cys Gly His Pro Gly Asp Thr Pro Phe Gly Thr Phe
             85                  90                  95

Thr Leu Thr Gly Gly Asn Val Phe Glu Tyr Gly Val Lys Ala Val Tyr
        100                 105                 110

Thr Cys Asn Glu Gly Tyr Gln Leu Leu Gly Glu Ile Asn Tyr Arg Glu
    115                 120                 125

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Ser Phe Thr
        435                 440                 445

Leu

<210> SEQ ID NO 29
<211> LENGTH: 1231
<212> TYPE: PRT
<213> ORGANISM: Homo sapiens
```

<400> SEQUENCE: 29

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
```

```
                    405                 410                 415
His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
            435                 440                 445

Ser Lys Ser Ser Ile Asp Ile Glu Asn Gly Phe Ile Ser Glu Ser Gln
        450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830
```

```
Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
            885                 890                 895

Leu Ser Tyr Thr Cys Glu Gly Gly Phe Arg Ile Ser Glu Glu Asn Glu
        900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
        930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230
```

<210> SEQ ID NO 30
<211> LENGTH: 644
<212> TYPE: PRT
<213> ORGANISM: Homo sapiens

<400> SEQUENCE: 30

```
Gly His Cys Gln Ala Pro Asp His Phe Leu Phe Ala Lys Leu Lys Thr
1               5                   10                  15
Gln Thr Asn Ala Ser Asp Phe Pro Ile Gly Thr Ser Leu Lys Tyr Glu
            20                  25                  30
Cys Arg Pro Glu Tyr Tyr Gly Arg Pro Phe Ser Ile Thr Cys Leu Asp
        35                  40                  45
Asn Leu Val Trp Ser Ser Pro Lys Asp Val Cys Lys Arg Lys Ser Cys
    50                  55                  60
Lys Thr Pro Pro Asp Pro Val Asn Gly Met Val His Val Ile Thr Asp
65                  70                  75                  80
Ile Gln Val Gly Ser Arg Ile Asn Tyr Ser Cys Thr Thr Gly His Arg
                85                  90                  95
Leu Ile Gly His Ser Ser Ala Glu Cys Ile Leu Ser Gly Asn Ala Ala
            100                 105                 110
His Trp Ser Thr Lys Pro Pro Ile Cys Gln Arg Ile Pro Cys Gly Leu
        115                 120                 125
Pro Pro Thr Ile Ala Asn Gly Asp Phe Ile Ser Thr Asn Arg Glu Asn
    130                 135                 140
Phe His Tyr Gly Ser Val Val Thr Tyr Arg Cys Asn Pro Gly Ser Gly
145                 150                 155                 160
Gly Arg Lys Val Phe Glu Leu Val Gly Glu Pro Ser Ile Tyr Cys Thr
                165                 170                 175
Ser Asn Asp Asp Gln Val Gly Ile Trp Ser Gly Pro Ala Pro Gln Cys
            180                 185                 190
Ile Ile Pro Asn Lys Cys Thr Pro Pro Asn Val Glu Asn Gly Ile Leu
        195                 200                 205
Val Ser Asp Asn Arg Ser Leu Phe Ser Leu Asn Glu Val Val Glu Phe
    210                 215                 220
Arg Cys Gln Pro Gly Phe Val Met Lys Gly Pro Arg Arg Val Lys Cys
225                 230                 235                 240
Gln Ala Leu Asn Lys Trp Glu Pro Glu Leu Pro Ser Cys Ser Arg Val
                245                 250                 255
Cys Gln Pro Pro Pro Asp Val Leu His Ala Glu Arg Thr Gln Arg Asp
            260                 265                 270
Lys Asp Asn Phe Ser Pro Gly Gln Glu Val Phe Tyr Ser Cys Glu Pro
        275                 280                 285
Gly Tyr Asp Leu Arg Gly Ala Ala Ser Met Arg Cys Thr Pro Gln Gly
    290                 295                 300
Asp Trp Ser Pro Ala Ala Pro Thr Cys Glu Val Lys Ser Cys Asp Asp
305                 310                 315                 320
Phe Met Gly Gln Leu Leu Asn Gly Arg Val Leu Phe Pro Val Asn Leu
                325                 330                 335
Gln Leu Gly Ala Lys Val Asp Phe Val Cys Asp Glu Gly Phe Gln Leu
            340                 345                 350
Lys Gly Ser Ser Ala Ser Tyr Cys Val Leu Ala Gly Met Glu Ser Leu
        355                 360                 365
Trp Asn Ser Ser Val Pro Val Cys Glu Gln Ile Phe Cys Pro Ser Pro
    370                 375                 380
```

```
Pro Val Ile Pro Asn Gly Arg His Thr Gly Lys Pro Leu Glu Val Phe
385                 390                 395                 400

Pro Phe Gly Lys Ala Val Asn Tyr Thr Cys Asp Pro His Pro Asp Arg
            405                 410                 415

Gly Thr Ser Phe Asp Leu Ile Gly Glu Ser Thr Ile Arg Cys Thr Ser
        420                 425                 430

Asp Pro Gln Gly Asn Gly Val Trp Ser Ser Pro Ala Pro Arg Cys Gly
    435                 440                 445

Ile Leu Gly His Cys Gln Ala Pro Asp His Phe Leu Phe Ala Lys Leu
450                 455                 460

Lys Thr Gln Thr Asn Ala Ser Asp Phe Pro Ile Gly Thr Ser Leu Lys
465                 470                 475                 480

Tyr Glu Cys Arg Pro Glu Tyr Tyr Gly Arg Pro Phe Ser Ile Thr Cys
                485                 490                 495

Leu Asp Asn Leu Val Trp Ser Ser Pro Lys Asp Val Cys Lys Arg Lys
            500                 505                 510

Ser Cys Lys Thr Pro Pro Asp Pro Val Asn Gly Met Val His Val Ile
        515                 520                 525

Thr Asp Ile Gln Val Gly Ser Arg Ile Asn Tyr Ser Cys Thr Thr Gly
530                 535                 540

His Arg Leu Ile Gly His Ser Ser Ala Glu Cys Ile Leu Ser Gly Asn
545                 550                 555                 560

Thr Ala His Trp Ser Thr Lys Pro Pro Ile Cys Gln Arg Ile Pro Cys
                565                 570                 575

Gly Leu Pro Pro Thr Ile Ala Asn Gly Asp Phe Ile Ser Thr Asn Arg
            580                 585                 590

Glu Asn Phe His Tyr Gly Ser Val Val Thr Tyr Arg Cys Asn Leu Gly
        595                 600                 605

Ser Arg Gly Arg Lys Val Phe Glu Leu Val Gly Glu Pro Ser Ile Tyr
    610                 615                 620

Cys Thr Ser Asn Asp Asp Gln Val Gly Ile Trp Ser Gly Pro Ala Pro
625                 630                 635                 640

Gln Cys Ile Ile

<210> SEQ ID NO 31
<211> LENGTH: 644
<212> TYPE: PRT
<213> ORGANISM: Homo sapiens

<400> SEQUENCE: 31

Gly His Cys Gln Ala Pro Asp His Phe Leu Phe Ala Lys Leu Lys Thr
1               5                   10                  15

Gln Thr Gln Ala Ser Asp Phe Pro Ile Gly Thr Ser Leu Lys Tyr Glu
            20                  25                  30

Cys Arg Pro Glu Tyr Tyr Gly Arg Pro Phe Ser Ile Thr Cys Leu Asp
        35                  40                  45

Asn Leu Val Trp Ser Ser Pro Lys Asp Val Cys Lys Arg Lys Ser Cys
    50                  55                  60

Lys Thr Pro Pro Asp Pro Val Asn Gly Met Val His Val Ile Thr Asp
65                  70                  75                  80

Ile Gln Val Gly Ser Arg Ile Gln Tyr Ser Cys Thr Thr Gly His Arg
                85                  90                  95

Leu Ile Gly His Ser Ser Ala Glu Cys Ile Leu Ser Gly Asn Ala Ala
            100                 105                 110
```

```
His Trp Ser Thr Lys Pro Pro Ile Cys Gln Arg Ile Pro Cys Gly Leu
            115                 120                 125

Pro Pro Thr Ile Ala Asn Gly Asp Phe Ile Ser Thr Asn Arg Glu Asn
130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys Cys Thr Pro Pro Asn Val Glu Asn Gly Ile Leu
            195                 200                 205

Val Ser Asp Asn Arg Ser Leu Phe Ser Leu Asn Glu Val Val Glu Phe
210                 215                 220

Arg Cys Gln Pro Gly Phe Val Met Lys Gly Pro Arg Arg Val Lys Cys
225                 230                 235                 240

Gln Ala Leu Asn Lys Trp Glu Pro Glu Leu Pro Ser Cys Ser Arg Val
            245                 250                 255

Cys Gln Pro Pro Pro Asp Val Leu His Ala Glu Arg Thr Gln Arg Asp
            260                 265                 270

Lys Asp Asn Phe Ser Pro Gly Gln Glu Val Phe Tyr Ser Cys Glu Pro
            275                 280                 285

Gly Tyr Asp Leu Arg Gly Ala Ala Ser Met Arg Cys Thr Pro Gln Gly
            290                 295                 300

Asp Trp Ser Pro Ala Ala Pro Thr Cys Glu Val Lys Ser Cys Asp Asp
305                 310                 315                 320

Phe Met Gly Gln Leu Leu Asn Gly Arg Val Leu Phe Pro Val Asn Leu
                325                 330                 335

Gln Leu Gly Ala Lys Val Asp Phe Val Cys Asp Glu Gly Phe Gln Leu
            340                 345                 350

Lys Gly Ser Ser Ala Ser Tyr Cys Val Leu Ala Gly Met Glu Ser Leu
            355                 360                 365

Trp Asn Ser Ser Val Pro Val Cys Glu Gln Ile Phe Cys Pro Ser Pro
            370                 375                 380

Pro Val Ile Pro Asn Gly Arg His Thr Gly Lys Pro Leu Glu Val Phe
385                 390                 395                 400

Pro Phe Gly Lys Ala Val Asn Tyr Thr Cys Asp Pro His Pro Asp Arg
            405                 410                 415

Gly Thr Ser Phe Asp Leu Ile Gly Glu Ser Thr Ile Arg Cys Thr Ser
            420                 425                 430

Asp Pro Gln Gly Asn Gly Val Trp Ser Ser Pro Ala Pro Arg Cys Gly
            435                 440                 445

Ile Leu Gly His Cys Gln Ala Pro Asp His Phe Leu Phe Ala Lys Leu
            450                 455                 460

Lys Thr Gln Thr Gln Ala Ser Asp Phe Pro Ile Gly Thr Ser Leu Lys
465                 470                 475                 480

Tyr Glu Cys Arg Pro Glu Tyr Tyr Gly Arg Pro Phe Ser Ile Thr Cys
                485                 490                 495

Leu Asp Asn Leu Val Trp Ser Ser Pro Lys Asp Val Cys Lys Arg Lys
            500                 505                 510

Ser Cys Lys Thr Pro Pro Asp Pro Val Asn Gly Met Val His Val Ile
            515                 520                 525
```

```
Thr Asp Ile Gln Val Gly Ser Arg Ile Gln Tyr Ser Cys Thr Thr Gly
    530                 535                 540

His Arg Leu Ile Gly His Ser Ser Ala Glu Cys Ile Leu Ser Gly Asn
545                 550                 555                 560

Thr Ala His Trp Ser Thr Lys Pro Pro Ile Cys Gln Arg Ile Pro Cys
                565                 570                 575

Gly Leu Pro Pro Thr Ile Ala Asn Gly Asp Phe Ile Ser Thr Asn Arg
            580                 585                 590

Glu Asn Phe His Tyr Gly Ser Val Val Thr Tyr Arg Cys Asn Leu Gly
        595                 600                 605

Ser Arg Gly Arg Lys Val Phe Glu Leu Val Gly Glu Pro Ser Ile Tyr
    610                 615                 620

Cys Thr Ser Asn Asp Asp Gln Val Gly Ile Trp Ser Gly Pro Ala Pro
625                 630                 635                 640

Gln Cys Ile Ile
```

```
<210> SEQ ID NO 32
<211> LENGTH: 25
<212> TYPE: PRT
<213> ORGANISM: Homo sapiens

<400> SEQUENCE: 32

Ala Leu Ile Val Gly Thr Leu Ser Gly Thr Ile Phe Phe Ile Leu Leu
1               5                   10                  15

Ile Ile Phe Leu Ser Trp Ile Ile Leu
            20                  25
```

```
<210> SEQ ID NO 33
<211> LENGTH: 43
<212> TYPE: PRT
<213> ORGANISM: Homo sapiens

<400> SEQUENCE: 33

Lys His Arg Lys Gly Asn Asn Ala His Glu Asn Pro Lys Glu Val Ala
1               5                   10                  15

Ile His Leu His Ser Gln Gly Gly Ser Ser Val His Pro Arg Thr Leu
            20                  25                  30

Gln Thr Asn Glu Glu Asn Ser Arg Val Leu Pro
        35                  40
```

```
<210> SEQ ID NO 34
<211> LENGTH: 8
<212> TYPE: PRT
<213> ORGANISM: Artificial Sequence
<220> FEATURE:
<223> OTHER INFORMATION: Synthetic construct

<400> SEQUENCE: 34

Glu Asn Leu Tyr Phe Gln Gly Ser
1               5
```

```
<210> SEQ ID NO 35
<211> LENGTH: 657
<212> TYPE: DNA
<213> ORGANISM: Homo sapiens

<400> SEQUENCE: 35
aagcttgcca ccatgagact gctggccaag atcatctgcc tgatgctgtg ggccatctgc     60
gtggccggac attgtcaggc ccctgaccac ttcctgttcg ccaagctgaa aacccagacc    120
```

| | |
|---|---|
| aacgccagcg acttccctat cggcaccagc ctgaagtacg agtgcagacc cgagtactac | 180 |
| ggcagaccct tcagcatcac ctgtctggac aacctcgtgt ggtctagccc caaggacgtg | 240 |
| tgcaagagaa agagctgcaa gacccctcct gatcctgtga acggcatggt gcacgtgatc | 300 |
| accgacatcc aagtgggcag cagaatcaac tacagctgca ccaccggcca cagactgatc | 360 |
| ggacactcta gcgccgagtg tatcctgagc ggcaatgccg cacactggtc caccaagcct | 420 |
| ccaatctgcc agagaatccc ttgcggcctg cctcctacaa cgccaacgg cgatttcatc | 480 |
| agcaccaaca gagagaactt ccactacggc tccgtggtca cctacagatg caatcctggc | 540 |
| agcggcggca gaaaggtgtt cgaacttgtg ggcgagccca gcatctactg caccagcaac | 600 |
| gatgaccaag tcggcatttg gagcggccct gctcctcagt gcatcatcta agatatc | 657 |

<210> SEQ ID NO 36
<211> LENGTH: 657
<212> TYPE: DNA
<213> ORGANISM: Homo sapiens

<400> SEQUENCE: 36

| | |
|---|---|
| aagcttgcca ccatgagact gctggccaag atcatctgcc tgatgctgtg ggccatctgc | 60 |
| gtggccggac attgtcaggc ccctgaccac ttcctgttcg ccaagctgaa aacccagaca | 120 |
| caggccagcg acttccctat cggcaccagc ctgaagtacg agtgcagacc cgagtactac | 180 |
| ggcagaccct tcagcatcac ctgtctggac aacctcgtgt ggtctagccc caaggacgtg | 240 |
| tgcaagagaa agagctgcaa gacccctcct gatcctgtga acggcatggt gcacgtgatc | 300 |
| accgacatcc aagtgggcag cagaatccag tacagctgca ccacaggcca cagactgatc | 360 |
| ggccactcta gcgccgagtg tatcctgtct ggcaatgccg ctcactggtc caccaagcct | 420 |
| ccaatctgcc agagaatccc ttgcggcctg cctcctacaa cgccaacgg cgatttcatc | 480 |
| agcaccaaca gagagaactt ccactacggc tccgtggtca cctacagatg caatcctggc | 540 |
| agcggcggca gaaaggtgtt cgaacttgtg ggcgagccca gcatctactg caccagcaac | 600 |
| gatgaccaag tcggcatttg gagcggccct gctcctcagt gcatcatcta agatatc | 657 |

<210> SEQ ID NO 37
<211> LENGTH: 659
<212> TYPE: DNA
<213> ORGANISM: Homo sapiens

<400> SEQUENCE: 37

| | |
|---|---|
| aagcttgcca ccatgagact gctggccaag atcatctgcc tgatgctgtg ggccatctgc | 60 |
| gtggccggcc actgtcaggc ccctgatcac ttcctgttcg ccaagctgaa aacccagacc | 120 |
| aacgccagcg acttccctat cggcaccagc ctgaagtacg agtgcagacc cgagtactac | 180 |
| ggcagaccct tcagcatcac ctgtctggac aacctcgtgt ggtctagccc caaggacgtg | 240 |
| tgcaagagaa agagctgcaa gacccctcct gatcctgtga acggcatggt gcacgtgatc | 300 |
| accgacatcc aagtgggcag cagaatcaac tacagctgca ccaccggcca cagactgatc | 360 |
| ggacactcta gcgccgagtg tatcctgagc ggcaatgccg cacactggtc caccaagcct | 420 |
| ccaatctgcc agagaatccc ttgcggcctg cctcctacaa cgccaacgg cgatttcatc | 480 |
| agcaccaaca gagagaactt ccactacggc tccgtggtca cctacagatg caatcctggc | 540 |
| agcggcggca gaaaggtgtt cgaacttgtg ggcgagccca gcatctactg caccagcaac | 600 |
| gatgaccaag tcggcatttg gagcggccct gctcctcagt gcatcatccc taagatatc | 659 |

<210> SEQ ID NO 38
<211> LENGTH: 659
<212> TYPE: DNA
<213> ORGANISM: Homo sapiens

<400> SEQUENCE: 38

| | | | | | |
|---|---|---|---|---|---|
| aagcttgcca | ccatgagact | gctggccaag | atcatctgcc | tgatgctgtg ggccatctgc | 60 |
| gtggccggcc | actgtcaggc | ccctgatcac | ttcctgttcg | ccaagctgaa aacccagaca | 120 |
| caggccagcg | acttccctat | cggcaccagc | ctgaagtacg | agtgcagacc cgagtactac | 180 |
| ggcagaccct | cagcatcac | ctgtctggac | aacctcgtgt | ggtctagccc caaggacgtg | 240 |
| tgcaagagaa | agagctgcaa | gacccctcct | gatcctgtga | acggcatggt gcacgtgatc | 300 |
| accgacatcc | aagtgggcag | cagaatccag | tacagctgca | ccacaggcca cagactgatc | 360 |
| ggccactcta | gcgccgagtg | tatcctgagc | ggaaacacag | cccactggtc caccaagcct | 420 |
| ccaatctgcc | agagaatccc | ttgcggcctg | cctcctacaa | tcgccaacgg cgatttcatc | 480 |
| agcaccaaca | gagagaactt | ccactacggc | tccgtggtca | cctacagatg caacctgggc | 540 |
| tccagaggcc | ggaaggtgtt | cgaacttgtg | ggcgagccta | gcatctactg caccagcaac | 600 |
| gacgaccaag | tcggcatttg | gagcggacct | gctcctcagt | gcatcatccc taagatatc | 659 |

<210> SEQ ID NO 39
<211> LENGTH: 714
<212> TYPE: DNA
<213> ORGANISM: Homo sapiens

<400> SEQUENCE: 39

| | | | | | |
|---|---|---|---|---|---|
| aagcttgcca | ccatgagact | gctggccaag | atcatctgcc | tgatgctgtg ggccatctgc | 60 |
| gtggcccacc | accatcacca | tcacggcagc | agcgagaacc | tgtacttcca aggatcttct | 120 |
| ggcggccact | gtcaggcccc | tgatcacttc | ctgttcgcca | agctgaaaac ccagaccaac | 180 |
| gccagcgact | tccctatcgg | caccagcctg | aagtacgagt | gcagacccga gtactacggc | 240 |
| agacccttca | gcatcacctg | tctggacaac | ctcgtgtggt | ctagccccaa ggacgtgtgc | 300 |
| aagagaaaga | gctgcaagac | ccctcctgat | cctgtgaacg | gcatggtgca cgtgatcacc | 360 |
| gacatccaag | tgggcagcag | aatcaactac | agctgcacca | ccggccacag actgatcgga | 420 |
| cactctagcg | ccgagtgtat | cctgagcggc | aatgccgcac | actggtccac caagcctcca | 480 |
| atctgccaga | gaatcccttg | cggcctgcct | cctacaatcg | ccaacggcga tttcatcagc | 540 |
| accaacagag | agaacttcca | ctacggctcc | gtggtcacct | acagatgcaa tcctggcagc | 600 |
| ggcggcagaa | aggtgttcga | acttgtgggc | gagcccagca | tctactgcac cagcaacgat | 660 |
| gaccaagtcg | gcatttggag | cggccctgct | cctcagtgca | tcatctaaga tatc | 714 |

<210> SEQ ID NO 40
<211> LENGTH: 231
<212> TYPE: PRT
<213> ORGANISM: Homo sapiens

<400> SEQUENCE: 40

Met Arg Leu Leu Ala Lys Ile Ile Cys Leu Met Leu Trp Ala Ile Cys
1               5                   10                  15

Val Ala His His His His His His Gly Ser Ser Glu Asn Leu Tyr Phe
            20                  25                  30

Gln Gly Ser Ser Gly Gly His Cys Gln Ala Pro Asp His Phe Leu Phe
        35                  40                  45

Ala Lys Leu Lys Thr Gln Thr Asn Ala Ser Asp Phe Pro Ile Gly Thr

```
          50                  55                  60
Ser Leu Lys Tyr Glu Cys Arg Pro Glu Tyr Tyr Gly Arg Pro Phe Ser
 65                  70                  75                  80

Ile Thr Cys Leu Asp Asn Leu Val Trp Ser Pro Lys Asp Val Cys
                 85                  90                  95

Lys Arg Lys Ser Cys Lys Thr Pro Asp Pro Val Asn Gly Met Val
                100                 105                 110

His Val Ile Thr Asp Ile Gln Val Gly Ser Arg Ile Asn Tyr Ser Cys
                115                 120                 125

Thr Thr Gly His Arg Leu Ile Gly His Ser Ser Ala Glu Cys Ile Leu
            130                 135                 140

Ser Gly Asn Ala Ala His Trp Ser Thr Lys Pro Pro Ile Cys Gln Arg
145                 150                 155                 160

Ile Pro Cys Gly Leu Pro Pro Thr Ile Ala Asn Gly Asp Phe Ile Ser
                165                 170                 175

Thr Asn Arg Glu Asn Phe His Tyr Gly Ser Val Val Thr Tyr Arg Cys
            180                 185                 190

Asn Pro Gly Ser Gly Gly Arg Lys Val Phe Glu Leu Val Gly Glu Pro
        195                 200                 205

Ser Ile Tyr Cys Thr Ser Asn Asp Asp Gln Val Gly Ile Trp Ser Gly
    210                 215                 220

Pro Ala Pro Gln Cys Ile Ile
225                 230

<210> SEQ ID NO 41
<211> LENGTH: 714
<212> TYPE: DNA
<213> ORGANISM: Homo sapiens

<400> SEQUENCE: 41
aagcttgcca ccatgagact gctggccaag atcatctgcc tgatgctgtg ggccatctgc      60
gtggcccacc accatcacca tcacggcagc agcgagaacc tgtacttcca aggatcttct    120
ggcggccact gtcaggcccc tgatcacttc ctgttcgcca agctgaaaac ccagacacag    180
gccagcgact ccctatcgg caccagcctg aagtacgagt gcagacccga gtactacggc     240
agacccttca gcatcacctg tctggacaac ctcgtgtggt ctagccccaa ggacgtgtgc    300
aagagaaaga gctgcaagac ccctcctgat cctgtgaacg gcatggtgca cgtgatcacc    360
gacatccaag tgggcagcag aatccagtac agctgcacca caggccacag actgatcggc    420
cactctagcg ccgagtgtat cctgtctggc aatgccgctc actggtccac caagcctcca    480
atctgccaga gaatcccttg cggcctgcct cctacaatcg ccaacggcga tttcatcagc    540
accaacagag agaacttcca ctacggctcc gtggtcacct acagatgcaa tcctggcagc    600
ggcggcagaa aggtgttcga acttgtgggc gagcccagca tctactgcac cagcaacgat    660
gaccaagtcg gcatttggag cggccctgct cctcagtgca tcatctaaga tatc          714

<210> SEQ ID NO 42
<211> LENGTH: 231
<212> TYPE: PRT
<213> ORGANISM: Homo sapiens

<400> SEQUENCE: 42

Met Arg Leu Leu Ala Lys Ile Ile Cys Leu Met Leu Trp Ala Ile Cys
  1               5                  10                  15

Val Ala His His His His His His Gly Ser Ser Glu Asn Leu Tyr Phe
```

```
                    20                  25                  30
Gln Gly Ser Ser Gly His Cys Gln Ala Pro Asp His Phe Leu Phe
            35                  40                  45

Ala Lys Leu Lys Thr Gln Thr Gln Ala Ser Asp Phe Pro Ile Gly Thr
 50                  55                  60

Ser Leu Lys Tyr Glu Cys Arg Pro Glu Tyr Tyr Gly Arg Pro Phe Ser
 65                  70                  75                  80

Ile Thr Cys Leu Asp Asn Leu Val Trp Ser Ser Pro Lys Asp Val Cys
                85                  90                  95

Lys Arg Lys Ser Cys Lys Thr Pro Pro Asp Pro Val Asn Gly Met Val
            100                 105                 110

His Val Ile Thr Asp Ile Gln Val Gly Ser Arg Ile Gln Tyr Ser Cys
            115                 120                 125

Thr Thr Gly His Arg Leu Ile Gly His Ser Ser Ala Glu Cys Ile Leu
            130                 135                 140

Ser Gly Asn Ala Ala His Trp Ser Thr Lys Pro Pro Ile Cys Gln Arg
145                 150                 155                 160

Ile Pro Cys Gly Leu Pro Pro Thr Ile Ala Asn Gly Asp Phe Ile Ser
                165                 170                 175

Thr Asn Arg Glu Asn Phe His Tyr Gly Ser Val Val Thr Tyr Arg Cys
            180                 185                 190

Asn Pro Gly Ser Gly Gly Arg Lys Val Phe Glu Leu Val Gly Glu Pro
            195                 200                 205

Ser Ile Tyr Cys Thr Ser Asn Asp Asp Gln Val Gly Ile Trp Ser Gly
            210                 215                 220

Pro Ala Pro Gln Cys Ile Ile
225                 230

<210> SEQ ID NO 43
<211> LENGTH: 716
<212> TYPE: DNA
<213> ORGANISM: Homo sapiens

<400> SEQUENCE: 43
aagcttgcca ccatgagact gctggccaag atcatctgcc tgatgctgtg ggccatctgc      60
gtggcccacc accatcacca tcacggcagc agcgagaacc tgtacttcca aggatcttct     120
ggcggcacct gtcaggcccc tgatcacttc ctgttcgcca agctgaaaac ccagaccaac     180
gccagcgact ccctatcgg caccagcctg aagtacgagt gcagacccga gtactacggc     240
agacccttca gcatcacctg tctggacaac ctcgtgtggt ctagcccaa ggacgtgtgc     300 aagagaaaga gctgcaagac ccctcctgat cctgtgaacg gcatggtgca cgtgatcacc     360
gacatccaag tgggcagcag aatcaactac agctgcacca ccggccacag actgatcgga     420
cactctagcg ccgagtgtat cctgagcggc aatgccgcac actggtccac caagcctcca     480
atctgccaga gaatcccttg cggcctgcct cctacaatcg ccaacggcga tttcatcagc     540
accaacagag agaacttcca ctacggctcc gtggtcacct acagatgcaa tcctggcagc     600
ggcggcagaa aggtgttcga acttgtgggc gagcccagca tctactgcac cagcaacgat     660
gaccaagtcg gcatttggag cggccctgct cctcagtgca tcatccctaa gatatc        716

<210> SEQ ID NO 44
<211> LENGTH: 231
<212> TYPE: PRT
<213> ORGANISM: Homo sapiens
```

<400> SEQUENCE: 44

```
Met Arg Leu Leu Ala Lys Ile Ile Cys Leu Met Leu Trp Ala Ile Cys
1               5                   10                  15
Val Ala His His His His His His Gly Ser Ser Glu Asn Leu Tyr Phe
            20                  25                  30
Gln Gly Ser Gly Gly His Cys Gln Ala Pro Asp His Phe Leu Phe
        35                  40                  45
Ala Lys Leu Lys Thr Gln Thr Asn Ala Ser Asp Phe Pro Ile Gly Thr
    50                  55                  60
Ser Leu Lys Tyr Glu Cys Arg Pro Glu Tyr Tyr Gly Arg Pro Phe Ser
65                  70                  75                  80
Ile Thr Cys Leu Asp Asn Leu Val Trp Ser Ser Pro Lys Asp Val Cys
                85                  90                  95
Lys Arg Lys Ser Cys Lys Thr Pro Pro Asp Pro Val Asn Gly Met Val
            100                 105                 110
His Val Ile Thr Asp Ile Gln Val Gly Ser Arg Ile Asn Tyr Ser Cys
        115                 120                 125
Thr Thr Gly His Arg Leu Ile Gly His Ser Ser Ala Glu Cys Ile Leu
    130                 135                 140
Ser Gly Asn Thr Ala His Trp Ser Thr Lys Pro Pro Ile Cys Gln Arg
145                 150                 155                 160
Ile Pro Cys Gly Leu Pro Pro Thr Ile Ala Asn Gly Asp Phe Ile Ser
                165                 170                 175
Thr Asn Arg Glu Asn Phe His Tyr Gly Ser Val Val Thr Tyr Arg Cys
            180                 185                 190
Asn Leu Gly Ser Arg Gly Arg Lys Val Phe Glu Leu Val Gly Glu Pro
        195                 200                 205
Ser Ile Tyr Cys Thr Ser Asn Asp Asp Gln Val Gly Ile Trp Ser Gly
    210                 215                 220
Pro Ala Pro Gln Cys Ile Ile
225                 230
```

<210> SEQ ID NO 45
<211> LENGTH: 716
<212> TYPE: DNA
<213> ORGANISM: Homo sapiens

<400> SEQUENCE: 45

```
aagcttgcca ccatgagact gctggccaag atcatctgcc tgatgctgtg ggccatctgc      60
gtggcccacc accatcacca tcacggcagc agcgagaacc tgtacttcca aggatcttct     120
ggcggccact gtcaggcccc tgatcacttc ctgttcgcca agctgaaaac ccagacacag     180
gccagcgact ccctatcgg caccagcctg aagtacgagt gcagaccgga gtactacggc     240
agacccttca gcatcacctg tctggacaac ctcgtgtggt ctagccccaa ggacgtgtgc     300
aagagaaaga gctgcaagac ccctcctgat cctgtgaacg gcatggtgca cgtgatcacc     360
gacatccaag tgggcagcag aatccagtac agctgcacca caggccacag actgatcggc     420
cactctagcg ccgagtgtat cctgagcgga aacacagccc actggtccac caagcctcca     480
atctgccaga gaatcccttg cggcctgcct cctacaatcg ccaacggcga tttcatcagc     540
accaacagag agaacttcca ctacggctcc gtggtcacct acagatgcaa cctgggctcc     600
agaggccgga aggtgttcga acttgtgggc gagcctagca tctactgcac cagcaacgac     660
gaccaagtcg gcatttggag cggacctgct cctcagtgca tcatccctaa gatatc        716
```

<210> SEQ ID NO 46
<211> LENGTH: 231
<212> TYPE: PRT
<213> ORGANISM: Homo sapiens

<400> SEQUENCE: 46

Met Arg Leu Leu Ala Lys Ile Ile Cys Leu Met Leu Trp Ala Ile Cys
1               5                   10                  15

Val Ala His His His His His His Gly Ser Ser Glu Asn Leu Tyr Phe
            20                  25                  30

Gln Gly Ser Ser Gly Gly His Cys Gln Ala Pro Asp His Phe Leu Phe
        35                  40                  45

Ala Lys Leu Lys Thr Gln Thr Gln Ala Ser Asp Phe Pro Ile Gly Thr
    50                  55                  60

Ser Leu Lys Tyr Glu Cys Arg Pro Glu Tyr Tyr Gly Arg Pro Phe Ser
65                  70                  75                  80

Ile Thr Cys Leu Asp Asn Leu Val Trp Ser Ser Pro Lys Asp Val Cys
                85                  90                  95

Lys Arg Lys Ser Cys Lys Thr Pro Pro Asp Pro Val Asn Gly Met Val
            100                 105                 110

His Val Ile Thr Asp Ile Gln Val Gly Ser Arg Ile Gln Tyr Ser Cys
        115                 120                 125

Thr Thr Gly His Arg Leu Ile Gly His Ser Ser Ala Glu Cys Ile Leu
    130                 135                 140

Ser Gly Asn Ala Ala His Trp Ser Thr Lys Pro Pro Ile Cys Gln Arg
145                 150                 155                 160

Ile Pro Cys Gly Leu Pro Pro Thr Ile Ala Asn Gly Asp Phe Ile Ser
                165                 170                 175

Thr Asn Arg Glu Asn Phe His Tyr Gly Ser Val Val Thr Tyr Arg Cys
            180                 185                 190

Asn Pro Gly Ser Gly Gly Arg Lys Val Phe Glu Leu Val Gly Glu Pro
        195                 200                 205

Ser Ile Tyr Cys Thr Ser Asn Asp Asp Gln Val Gly Ile Trp Ser Gly
    210                 215                 220

Pro Ala Pro Gln Cys Ile Ile
225                 230

<210> SEQ ID NO 47
<211> LENGTH: 212
<212> TYPE: PRT
<213> ORGANISM: Artificial Sequence
<220> FEATURE:
<223> OTHER INFORMATION: Synthetic construct

<400> SEQUENCE: 47

Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
            20                  25                  30

Lys Thr Gln Thr Asn Ala Ser Asp Phe Pro Ile Gly Thr Ser Leu Lys
        35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile

```
                85                  90                  95
Thr Asp Ile Gln Val Gly Ser Arg Ile Asn Tyr Ser Cys Thr Thr Gly
            100                 105                 110

His Arg Leu Ile Gly His Ser Ser Ala Glu Cys Ile Leu Ser Gly Asn
            115                 120                 125

Ala Ala His Trp Ser Thr Lys Pro Pro Ile Cys Gln Arg Ile Pro Cys
        130                 135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Pro Gly
                165                 170                 175

Ser Gly Gly Arg Lys Val Phe Glu Leu Val Gly Glu Pro Ser Ile Tyr
            180                 185                 190

Cys Thr Ser Asn Asp Asp Gln Val Gly Ile Trp Ser Gly Pro Ala Pro
            195                 200                 205

Gln Cys Ile Ile
    210
```

<210> SEQ ID NO 48
<211> LENGTH: 212
<212> TYPE: PRT
<213> ORGANISM: Artificial Sequence
<220> FEATURE:
<223> OTHER INFORMATION: Synthetic construct

<400> SEQUENCE: 48

```
Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
            20                  25                  30

Lys Thr Gln Thr Gln Ala Ser Asp Phe Pro Ile Gly Thr Ser Leu Lys
        35                  40                  45

Tyr Glu Cys Arg Pro Glu Tyr Tyr Gly Arg Pro Phe Ser Ile Thr Cys
50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
                85                  90                  95

Thr Asp Ile Gln Val Gly Ser Arg Ile Gln Tyr Ser Cys Thr Thr Gly
            100                 105                 110

His Arg Leu Ile Gly His Ser Ser Ala Glu Cys Ile Leu Ser Gly Asn
            115                 120                 125

Ala Ala His Trp Ser Thr Lys Pro Pro Ile Cys Gln Arg Ile Pro Cys
        130                 135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Pro Gly
                165                 170                 175

Ser Gly Gly Arg Lys Val Phe Glu Leu Val Gly Glu Pro Ser Ile Tyr
            180                 185                 190

Cys Thr Ser Asn Asp Asp Gln Val Gly Ile Trp Ser Gly Pro Ala Pro
            195                 200                 205

Gln Cys Ile Ile
    210
```

<210> SEQ ID NO 49
<211> LENGTH: 212
<212> TYPE: PRT
<213> ORGANISM: Artificial Sequence
<220> FEATURE:
<223> OTHER INFORMATION: Synthetic construct

<400> SEQUENCE: 49

```
Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
            20                  25                  30

Lys Thr Gln Thr Asn Ala Ser Asp Phe Pro Ile Gly Thr Ser Leu Lys
        35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
                85                  90                  95

Thr Asp Ile Gln Val Gly Ser Arg Ile Asn Tyr Ser Cys Thr Thr Gly
            100                 105                 110

His Arg Leu Ile Gly His Ser Ser Ala Glu Cys Ile Leu Ser Gly Asn
        115                 120                 125

Thr Ala His Trp Ser Thr Lys Pro Pro Ile Cys Gln Arg Ile Pro Cys
    130                 135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Leu Gly
                165                 170                 175

Ser Arg Gly Arg Lys Val Phe Glu Leu Val Gly Glu Pro Ser Ile Tyr
            180                 185                 190

Cys Thr Ser Asn Asp Asp Gln Val Gly Ile Trp Ser Gly Pro Ala Pro
        195                 200                 205

Gln Cys Ile Ile
    210
```

<210> SEQ ID NO 50
<211> LENGTH: 212
<212> TYPE: PRT
<213> ORGANISM: Artificial Sequence
<220> FEATURE:
<223> OTHER INFORMATION: Synthetic construct

<400> SEQUENCE: 50

```
Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
            20                  25                  30

Lys Thr Gln Thr Gln Ala Ser Asp Phe Pro Ile Gly Thr Ser Leu Lys
        35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
                85                  90                  95
```

```
Thr Asp Ile Gln Val Gly Ser Arg Ile Gln Tyr Ser Cys Thr Thr Gly
            100                 105                 110

His Arg Leu Ile Gly His Ser Ser Ala Glu Cys Ile Leu Ser Gly Asn
            115                 120                 125

Thr Ala His Trp Ser Thr Lys Pro Pro Ile Cys Gln Arg Ile Pro Cys
        130                 135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Leu Gly
                165                 170                 175

Ser Arg Gly Arg Lys Val Phe Glu Leu Val Gly Glu Pro Ser Ile Tyr
            180                 185                 190

Cys Thr Ser Asn Asp Asp Gln Val Gly Ile Trp Ser Gly Pro Ala Pro
        195                 200                 205

Gln Cys Ile Ile
    210

<210> SEQ ID NO 51
<211> LENGTH: 406
<212> TYPE: PRT
<213> ORGANISM: Artificial Sequence
<220> FEATURE:
<223> OTHER INFORMATION: Synthetic construct

<400> SEQUENCE: 51

Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
                20                  25                  30

Lys Thr Gln Thr Asn Ala Ser Asp Phe Pro Ile Gly Thr Ser Leu Lys
            35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
                85                  90                  95

Thr Asp Ile Gln Val Gly Ser Arg Ile Asn Tyr Ser Cys Thr Thr Gly
            100                 105                 110

His Arg Leu Ile Gly His Ser Ser Ala Glu Cys Ile Leu Ser Gly Asn
            115                 120                 125

Ala Ala His Trp Ser Thr Lys Pro Pro Ile Cys Gln Arg Ile Pro Cys
        130                 135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Pro Gly
                165                 170                 175

Ser Gly Gly Arg Lys Val Phe Glu Leu Val Gly Glu Pro Ser Ile Tyr
            180                 185                 190

Cys Thr Ser Asn Asp Asp Gln Val Gly Ile Trp Ser Gly Pro Ala Pro
        195                 200                 205

Gln Cys Ile Ile Gly His Cys Gln Ala Pro Asp His Phe Leu Phe Ala
    210                 215                 220

Lys Leu Lys Thr Gln Thr Asn Ala Ser Asp Phe Pro Ile Gly Thr Ser
225                 230                 235                 240
```

```
Leu Lys Tyr Glu Cys Arg Pro Glu Tyr Tyr Gly Arg Pro Phe Ser Ile
            245                 250                 255

Thr Cys Leu Asp Asn Leu Val Trp Ser Ser Pro Lys Asp Val Cys Lys
        260                 265                 270

Arg Lys Ser Cys Lys Thr Pro Pro Asp Pro Val Asn Gly Met Val His
            275                 280                 285

Val Ile Thr Asp Ile Gln Val Gly Ser Arg Ile Asn Tyr Ser Cys Thr
        290                 295                 300

Thr Gly His Arg Leu Ile Gly His Ser Ser Ala Glu Cys Ile Leu Ser
305                 310                 315                 320

Gly Asn Thr Ala His Trp Ser Thr Lys Pro Ile Cys Gln Arg Ile
                325                 330                 335

Pro Cys Gly Leu Pro Pro Thr Ile Ala Asn Gly Asp Phe Ile Ser Thr
            340                 345                 350

Asn Arg Glu Asn Phe His Tyr Gly Ser Val Val Thr Tyr Arg Cys Asn
        355                 360                 365

Leu Gly Ser Arg Gly Arg Lys Val Phe Glu Leu Val Gly Glu Pro Ser
    370                 375                 380

Ile Tyr Cys Thr Ser Asn Asp Asp Gln Val Gly Ile Trp Ser Gly Pro
385                 390                 395                 400

Ala Pro Gln Cys Ile Ile
                405

<210> SEQ ID NO 52
<211> LENGTH: 406
<212> TYPE: PRT
<213> ORGANISM: Artificial Sequence
<220> FEATURE:
<223> OTHER INFORMATION: Synthetic construct

<400> SEQUENCE: 52

Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
            20                  25                  30

Lys Thr Gln Thr Gln Ala Ser Asp Phe Pro Ile Gly Thr Ser Leu Lys
        35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
                85                  90                  95

Thr Asp Ile Gln Val Gly Ser Arg Ile Gln Tyr Ser Cys Thr Thr Gly
            100                 105                 110

His Arg Leu Ile Gly His Ser Ser Ala Glu Cys Ile Leu Ser Gly Asn
        115                 120                 125

Ala Ala His Trp Ser Thr Lys Pro Pro Ile Cys Gln Arg Ile Pro Cys
    130                 135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Pro Gly
                165                 170                 175

Ser Gly Gly Arg Lys Val Phe Glu Leu Val Gly Glu Pro Ser Ile Tyr
            180                 185                 190
```

```
Cys Thr Ser Asn Asp Asp Gln Val Gly Ile Trp Ser Gly Pro Ala Pro
        195                 200                 205

Gln Cys Ile Ile Gly His Cys Gln Ala Pro Asp His Phe Leu Phe Ala
    210                 215                 220

Lys Leu Lys Thr Gln Thr Gln Ala Ser Asp Phe Pro Ile Gly Thr Ser
225                 230                 235                 240

Leu Lys Tyr Glu Cys Arg Pro Glu Tyr Tyr Gly Arg Pro Phe Ser Ile
                245                 250                 255

Thr Cys Leu Asp Asn Leu Val Trp Ser Ser Pro Lys Asp Val Cys Lys
            260                 265                 270

Arg Lys Ser Cys Lys Thr Pro Pro Asp Pro Val Asn Gly Met Val His
    275                 280                 285

Val Ile Thr Asp Ile Gln Val Gly Ser Arg Ile Gln Tyr Ser Cys Thr
    290                 295                 300

Thr Gly His Arg Leu Ile Gly His Ser Ser Ala Glu Cys Ile Leu Ser
305                 310                 315                 320

Gly Asn Thr Ala His Trp Ser Thr Lys Pro Pro Ile Cys Gln Arg Ile
                325                 330                 335

Pro Cys Gly Leu Pro Pro Thr Ile Ala Asn Gly Asp Phe Ile Ser Thr
            340                 345                 350

Asn Arg Glu Asn Phe His Tyr Gly Ser Val Val Thr Tyr Arg Cys Asn
    355                 360                 365

Leu Gly Ser Arg Gly Arg Lys Val Phe Glu Leu Val Gly Glu Pro Ser
    370                 375                 380

Ile Tyr Cys Thr Ser Asn Asp Asp Gln Val Gly Ile Trp Ser Gly Pro
385                 390                 395                 400

Ala Pro Gln Cys Ile Ile
                405

<210> SEQ ID NO 53
<211> LENGTH: 406
<212> TYPE: PRT
<213> ORGANISM: Artificial Sequence
<220> FEATURE:
<223> OTHER INFORMATION: Synthetic construct

<400> SEQUENCE: 53

Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
                20                  25                  30

Lys Thr Gln Thr Asn Ala Ser Asp Phe Pro Ile Gly Thr Ser Leu Lys
            35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
                85                  90                  95

Thr Asp Ile Gln Val Gly Ser Arg Ile Asn Tyr Ser Cys Thr Thr Gly
            100                 105                 110

His Arg Leu Ile Gly His Ser Ser Ala Glu Cys Ile Leu Ser Gly Asn
    115                 120                 125

Ala Ala His Trp Ser Thr Lys Pro Pro Ile Cys Gln Arg Ile Pro Cys
130                 135                 140
```

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Pro Gly
            165                 170                 175

Ser Gly Gly Arg Lys Val Phe Glu Leu Val Gly Glu Pro Ser Ile Tyr
        180                 185                 190

Cys Thr Ser Asn Asp Asp Gln Val Gly Ile Trp Ser Gly Pro Ala Pro
    195                 200                 205

Gln Cys Ile Ile Gly His Cys Gln Ala Pro Asp His Phe Leu Phe Ala
210                 215                 220

Lys Leu Lys Thr Gln Thr Gln Ala Ser Asp Phe Pro Ile Gly Thr Ser
225                 230                 235                 240

Leu Lys Tyr Glu Cys Arg Pro Glu Tyr Tyr Gly Arg Pro Phe Ser Ile
            245                 250                 255

Thr Cys Leu Asp Asn Leu Val Trp Ser Ser Pro Lys Asp Val Cys Lys
        260                 265                 270

Arg Lys Ser Cys Lys Thr Pro Pro Asp Pro Val Asn Gly Met Val His
    275                 280                 285

Val Ile Thr Asp Ile Gln Val Gly Ser Arg Ile Gln Tyr Ser Cys Thr
290                 295                 300

Thr Gly His Arg Leu Ile Gly His Ser Ser Ala Glu Cys Ile Leu Ser
305                 310                 315                 320

Gly Asn Thr Ala His Trp Ser Thr Lys Pro Pro Ile Cys Gln Arg Ile
            325                 330                 335

Pro Cys Gly Leu Pro Pro Thr Ile Ala Asn Gly Asp Phe Ile Ser Thr
        340                 345                 350

Asn Arg Glu Asn Phe His Tyr Gly Ser Val Val Thr Tyr Arg Cys Asn
    355                 360                 365

Leu Gly Ser Arg Gly Arg Lys Val Phe Glu Leu Val Gly Glu Pro Ser
370                 375                 380

Ile Tyr Cys Thr Ser Asn Asp Asp Gln Val Gly Ile Trp Ser Gly Pro
385                 390                 395                 400

Ala Pro Gln Cys Ile Ile
            405

<210> SEQ ID NO 54
<211> LENGTH: 406
<212> TYPE: PRT
<213> ORGANISM: Artificial Sequence
<220> FEATURE:
<223> OTHER INFORMATION: Synthetic construct

<400> SEQUENCE: 54

Met Arg Leu Leu Ala Lys Ile Ile Cys Leu Met Leu Trp Ala Ile Cys
1               5                   10                  15

Val Ala Gly His Cys Gln Ala Pro Asp His Phe Leu Phe Ala Lys Leu
            20                  25                  30

Lys Thr Gln Thr Gln Ala Ser Asp Phe Pro Ile Gly Thr Ser Leu Lys
        35                  40                  45

Tyr Glu Cys Arg Pro Glu Tyr Tyr Gly Arg Pro Phe Ser Ile Thr Cys
    50                  55                  60

Leu Asp Asn Leu Val Trp Ser Ser Pro Lys Asp Val Cys Lys Arg Lys
65                  70                  75                  80

Ser Cys Lys Thr Pro Pro Asp Pro Val Asn Gly Met Val His Val Ile
            85                  90                  95

-continued

```
Thr Asp Ile Gln Val Gly Ser Arg Ile Gln Tyr Ser Cys Thr Thr Gly
        100                 105                 110

His Arg Leu Ile Gly His Ser Ser Ala Glu Cys Ile Leu Ser Gly Asn
        115                 120                 125

Ala Ala His Trp Ser Thr Lys Pro Pro Ile Cys Gln Arg Ile Pro Cys
130                     135                 140

Gly Leu Pro Pro Thr Ile Ala Asn Gly Asp Phe Ile Ser Thr Asn Arg
145                 150                 155                 160

Glu Asn Phe His Tyr Gly Ser Val Val Thr Tyr Arg Cys Asn Pro Gly
                165                 170                 175

Ser Gly Gly Arg Lys Val Phe Glu Leu Val Gly Glu Pro Ser Ile Tyr
            180                 185                 190

Cys Thr Ser Asn Asp Asp Gln Val Gly Ile Trp Ser Gly Pro Ala Pro
        195                 200                 205

Gln Cys Ile Ile Gly His Cys Gln Ala Pro Asp His Phe Leu Phe Ala
        210                 215                 220

Lys Leu Lys Thr Gln Thr Asn Ala Ser Asp Phe Pro Ile Gly Thr Ser
225                 230                 235                 240

Leu Lys Tyr Glu Cys Arg Pro Glu Tyr Tyr Gly Arg Pro Phe Ser Ile
                245                 250                 255

Thr Cys Leu Asp Asn Leu Val Trp Ser Ser Pro Lys Asp Val Cys Lys
            260                 265                 270

Arg Lys Ser Cys Lys Thr Pro Pro Asp Pro Val Asn Gly Met Val His
        275                 280                 285

Val Ile Thr Asp Ile Gln Val Gly Ser Arg Ile Asn Tyr Ser Cys Thr
        290                 295                 300

Thr Gly His Arg Leu Ile Gly His Ser Ser Ala Glu Cys Ile Leu Ser
305                 310                 315                 320

Gly Asn Thr Ala His Trp Ser Thr Lys Pro Pro Ile Cys Gln Arg Ile
                325                 330                 335

Pro Cys Gly Leu Pro Pro Thr Ile Ala Asn Gly Asp Phe Ile Ser Thr
            340                 345                 350

Asn Arg Glu Asn Phe His Tyr Gly Ser Val Val Thr Tyr Arg Cys Asn
        355                 360                 365

Leu Gly Ser Arg Gly Arg Lys Val Phe Glu Leu Val Gly Glu Pro Ser
370                 375                 380

Ile Tyr Cys Thr Ser Asn Asp Asp Gln Val Gly Ile Trp Ser Gly Pro
385                 390                 395                 400

Ala Pro Gln Cys Ile Ile
                405
```